(12) United States Patent
Chen

(10) Patent No.: US 7,134,929 B2
(45) Date of Patent: Nov. 14, 2006

(54) TEAR RESISTANT GELS, COMPOSITES, AND DIVING APPAREL ARTICLES

(75) Inventor: John Y. Chen, Hillsborough, CA (US)

(73) Assignee: Applied Elastomerics, Inc., South San Francisco, CA (US)

( * ) Notice: Subject to any disclaimer, the term of this patent is extended or adjusted under 35 U.S.C. 154(b) by 431 days.

(21) Appl. No.: 10/420,488

(22) Filed: Apr. 21, 2003

(65) Prior Publication Data

US 2003/0186603 A1 Oct. 2, 2003

Related U.S. Application Data

(63) Continuation-in-part of application No. 10/334,542, filed on Dec. 31, 2002, and a continuation-in-part of application No. 10/299,073, filed on Nov. 18, 2002, and a continuation-in-part of application No. 10/273,828, filed on Oct. 17, 2002, now Pat. No. 6,909,220, and a continuation-in-part of application No. 10/199,364, filed on Jul. 20, 2002, now Pat. No. 6,794,440, and a continuation-in-part of application No. 10/199,361, filed on Jul. 20, 2002, and a continuation-in-part of application No. 10/199,362, filed on Jul. 20, 2002, and a continuation-in-part of application No. 10/199,363, filed on Jul. 20, 2002, and a continuation-in-part of application No. 09/721,213, filed on Nov. 21, 2001, now Pat. No. 6,867,253, and a continuation-in-part of application No. 09/896,047, filed on Jun. 30, 2001, and a continuation-in-part of application No. 09/517,230, filed on Mar. 2, 2000, now abandoned, and a continuation-in-part of application No. 09/412,886, filed on Oct. 5, 1999, now abandoned, and a continuation-in-part of application No. 09/285,809, filed on Apr. 1, 1999, now abandoned, and a continuation-in-part of application No. 09/274,498, filed on Mar. 23, 1999, now Pat. No. 6,420,475, and a continuation-in-part of application No. 09/130,545, filed on Aug. 8, 1998, now Pat. No. 5,467,626, and a continuation-in-part of application No. 08/984,459, filed on Dec. 3, 1997, now Pat. No. 6,324,703, and a continuation-in-part of application No. PCT/US97/17534, filed on Sep. 30, 1997, and a continuation-in-part of application No. 08/909,487, filed on Aug. 12, 1997, now Pat. No. 6,050,871, and a continuation-in-part of application No. 08/863,794, filed on May 27, 1997, now Pat. No. 6,117,176, and a continuation-in-part of application No. 08/719,817, filed on Sep. 30, 1996, now Pat. No. 6,148,830, and a continuation-in-part of application No. 08/665,343, filed on Jun. 17, 1996, which is a continuation-in-part of application No. 08/612,586, filed on Mar. 8, 1996, now Pat. No. 6,552,109, and a continuation-in-part of application No. 08/581,188, filed on Dec. 29, 1995, now abandoned, and a continuation-in-part of application No. 08/581,191, filed on Dec. 29, 1995, now Pat. No. 5,760,117, and a continuation-in-part of application No. 08/581,125, filed on Dec. 29, 1995, now Pat. No. 5,962,572, and a continuation-in-part of application No. 08/288,690, filed on Aug. 11, 1994, now Pat. No. 5,633,286, said application No. 08/581,188 is a continuation-in-part of application No. 08/288,690, filed on Aug. 11, 1994, now Pat. No. 5,633,286, and a continuation-in-part of application No. PCT/US94/07314, filed on Jun. 27, 1994, and a continuation-in-part of application No. PCT/US94/04278, filed on Apr. 19, 1994, said application No. 08/581,191 is a continuation-in-part of application No. 08/288,690, filed on Aug. 11, 1994, now Pat. No. 5,633,286, and a continuation-in-part of application No. PCT/US94/07314, filed on Jun. 27, 1994, and a continuation-in-part of application No. PCT/US94/04278, filed on Apr. 19, 1994, said application No. 08/581,125 is a continuation-in-part of application No. 08/288,690, filed on Aug. 11, 1994, now Pat. No. 5,633,286, and a continuation-in-part of application No. PCT/US94/07314, filed on Jun. 27, 1994, and a continuation-in-part of application No. PCT/US94/04278, filed on Apr. 19, 1994.

(51) Int. Cl.
*B63B 9/08* (2006.01)
*B63B 11/04* (2006.01)
*B32B 27/30* (2006.01)
*B32B 27/22* (2006.01)
*C08L 53/00* (2006.01)

(52) U.S. Cl. .................... 441/102; 2/2.15; 2/2.16; 442/62; 442/85; 524/505

(58) Field of Classification Search .............. 442/85, 442/62; 441/102; 2/458, 2.15, 2.16; 524/505
See application file for complete search history.

(56) References Cited

U.S. PATENT DOCUMENTS 6,324,703 B1 * 12/2001 Chen ......................... 2/458

* cited by examiner

Primary Examiner—Herbert J. Lilling

(57) ABSTRACT

Composite gel articles shaped in the form of a body shaped suit for diving made by injection molding, extruding, spinning, casting, or dipping.

12 Claims, 12 Drawing Sheets

| M1 | Fabric or Cloth |
| --- | --- |
| G | Gel |
| GM | Gel-Sponge or Gel-Foam |
| M2 | Foam or Sponge |
| M3 | Synthetic Resin or Plastic |
| M4 | Fibre |
| M5 | Concrete |
| M6 | Metal or Metal Sponge |
| M7 | Wood |
| M8 | Wire or Screening |
| M9 | Refractory Material |
| M10 | Other Material |

Figure 1

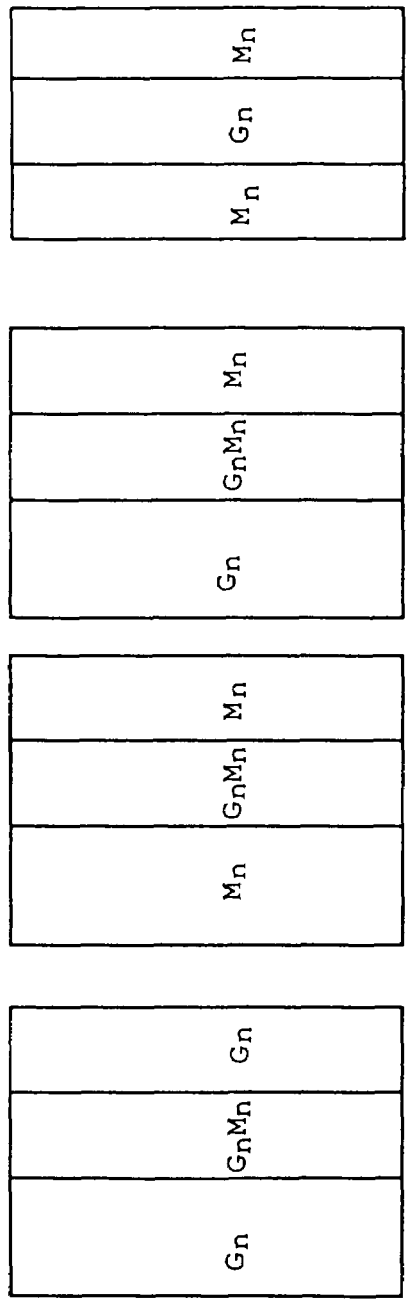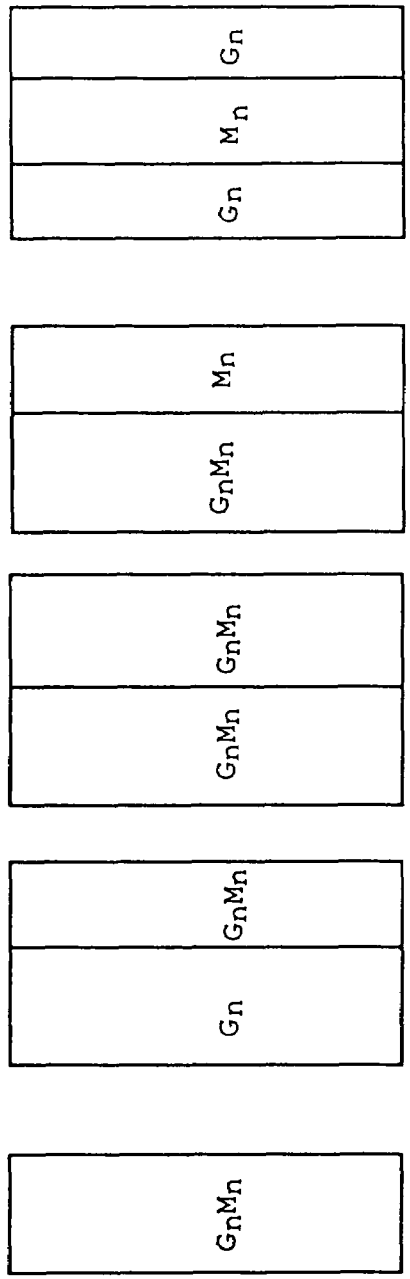

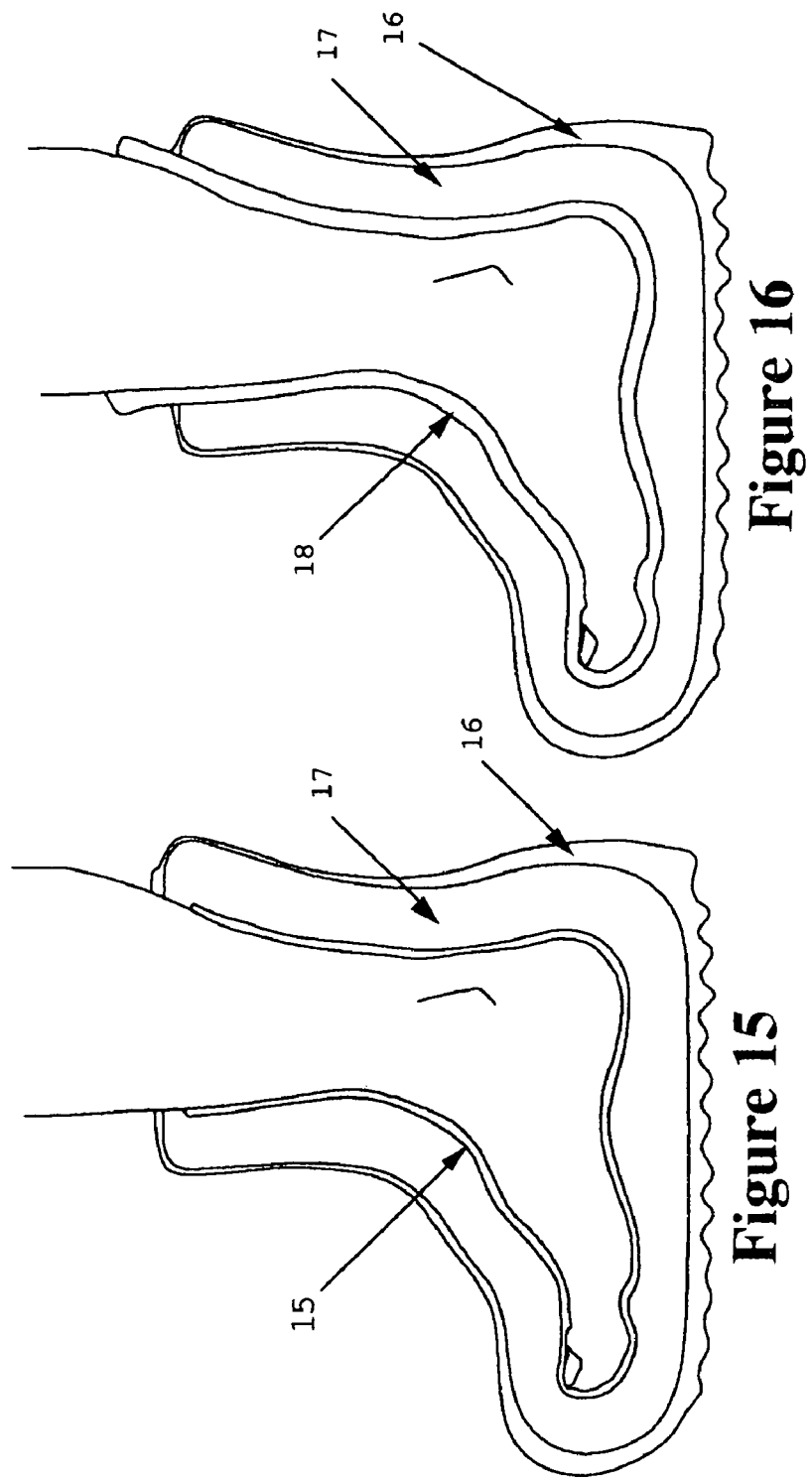

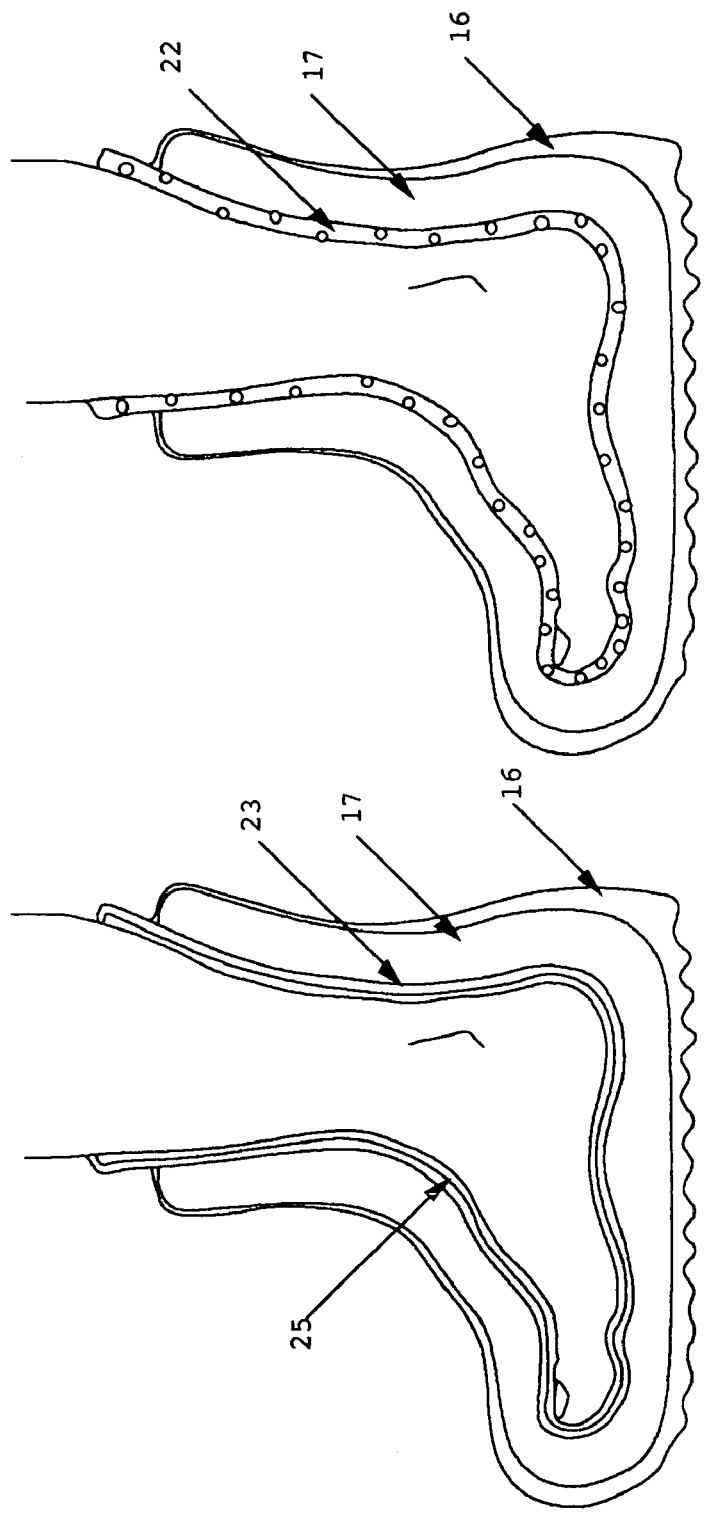

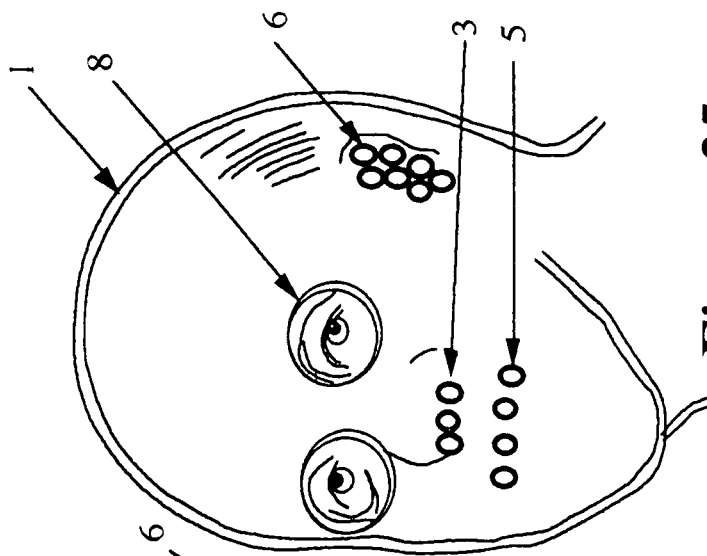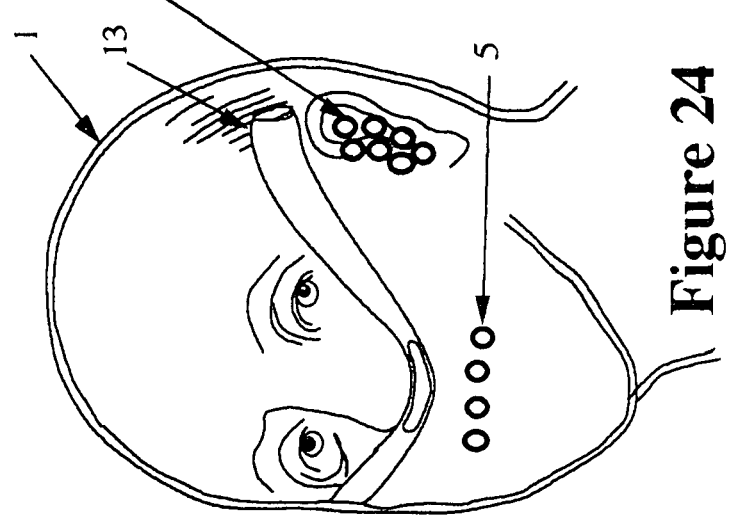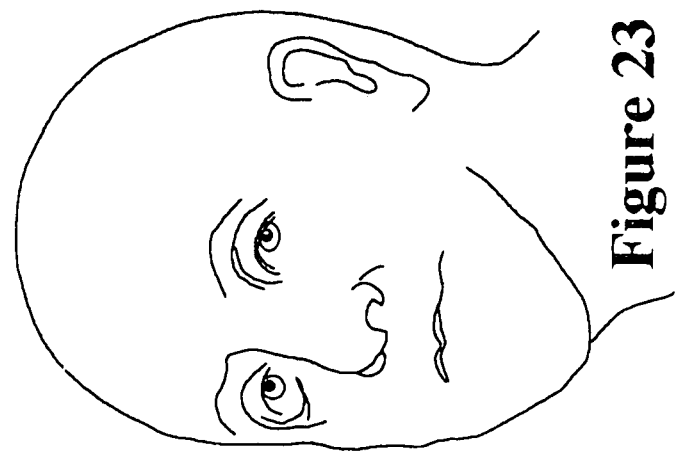

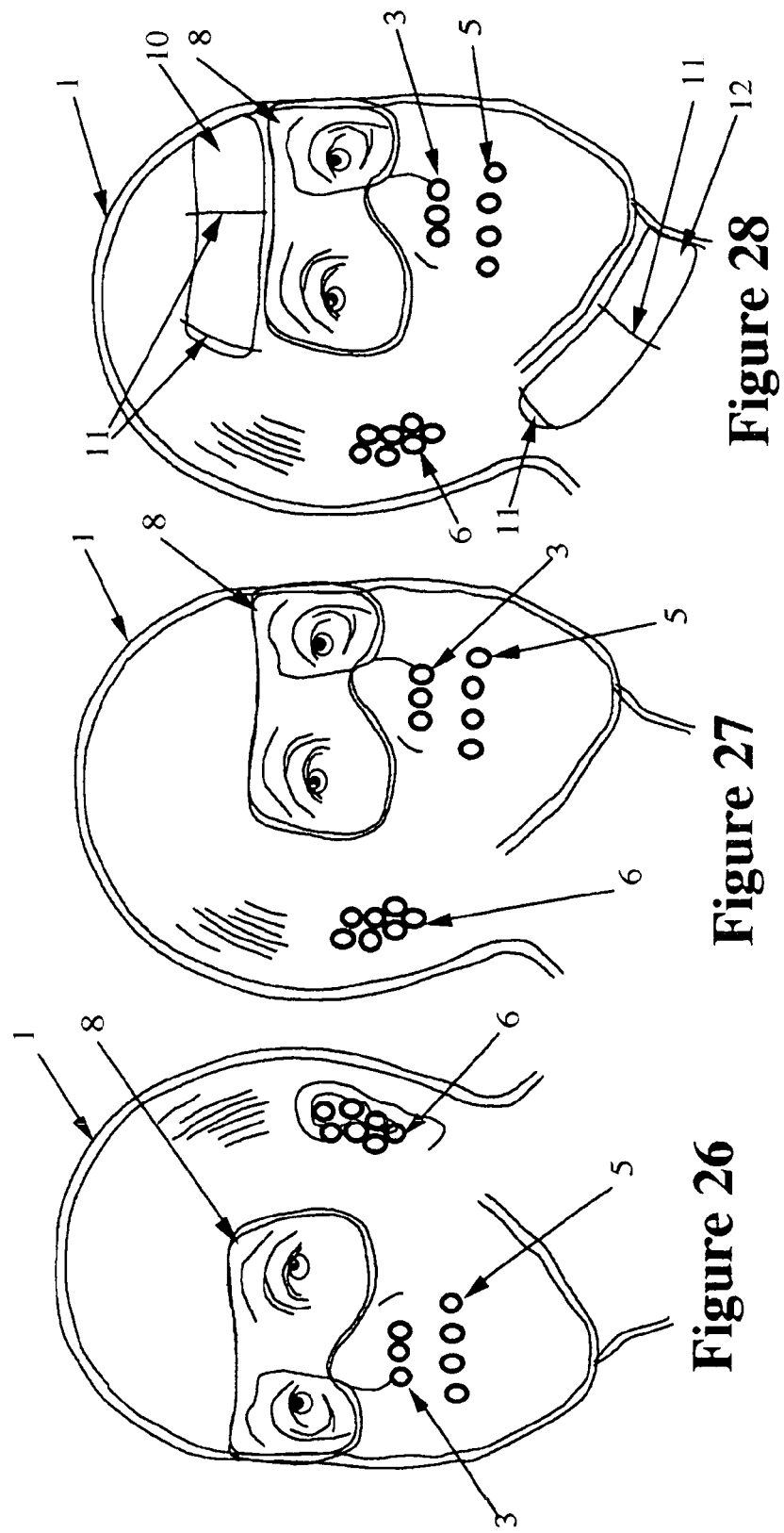

TEAR RESISTANT GELS, COMPOSITES, AND DIVING APPAREL ARTICLES

RELATED APPLICATIONS

This application is a continuation-in-part of the following applications: Ser. No. 09/896,047 filed Jun. 30, 2001; Ser. No. 10/273,828 filed Oct. 17, 2002 (now U.S. Pat. No. 6,909,220); Ser. No. 10/334,542 filed Dec. 31, 2002; Ser. No. 10/299,073 filed Nov. 18, 2002; Ser. No. 10/199,364 filed Jul. 20, 2002 (now U.S. Pat. No. 6,794,440); Ser. No. 09/721,213 filed Nov. 21, 2001 (now U.S. Pat. No. 6,867,253); Ser. No. 10/199,361 filed Jul. 20, 2002; Ser. No. 10/199,362 filed Jul. 20, 2002; Ser. No. 10/199,363 filed Jul. 20, 2002; Ser. No. 09/517,230, filed Mar. 2, 2000 (now abn.); Ser. No. 09/412,886, filed Oct. 5, 1999 (now abn.); Ser. No. 09/285,809, filed Apr. 1, 1999 (now abn.); Ser. No. 09/274,498, filed Mar. 23, 1999 (now U.S. Pat. No. 6,420,475); Ser. No 09/130,545, filed Aug. 8, 1998 (now U.S. Pat. No. 6,627,275); Ser. No. 08/984,459, filed Dec. 3, 1997 (now U.S. Pat. No. 6,324,703); Ser. No. 08/909,487, filed Jul. 12, 1997 (now U.S. Pat. No. 6,050,871); Ser. No. 08/863,794, filed May 27, 1997 (now U.S. Pat. No. 6,117,176); PCT/US97/17534, filed 30 Sep. 1997; U.S. Ser. No. 08/719,817 filed Sep. 30, 1996 (now U.S. Pat. No. 6,148,830); U.S. Ser. No. 08/665,343 filed Jun. 17, 1996 which is a Continuation-in-part of U.S. Ser. No. 08/612,586 filed Mar. 8, 1996 (now U.S. Pat. No. 6,552,109); PCT/US94/04278 filed Apr. 19, 1994 (U.S. Ser. No 08/211,781, now U.S. Pat. No. 6,033,283) (published May 26, 1995 No. WO95/13851); PCT/US94/07314 filed Jun. 27, 1994 (U.S. Ser. No. 08/256,235, now U.S. Pat. No. 5,868,597) (published Jan. 4, 1996 No. WO 96/00118); Ser. No. 08/288,690 filed Aug. 11, 1994 (now U.S. Pat. No. 5,633,286); Ser. No. 08/581,188 filed Dec. 29, 1995 (now abn.); Ser. No. 08/581,191 filed Dec. 29, 1995; Ser. No. 08/581,125 filed Dec. 29, 1995 now U.S. Pat. No. 5,962,527. In turn U.S. Ser. Nos. 08/581,188; 581,191; and 08/581,125 are continuation-in-parts of the following applications: Ser. No. 08/288,690, filed Aug. 11, 1994, PCT/US94/07314 filed Jun. 27, 1994 (CIP of PCT/US 94/04278, filed 19 Apr. 1994). The subject matter contained in the related applications and patents are specifically incorporated herein by reference.

FIELD OF THE INVENTION

The present invention is directed to novel gels and their uses.

BACKGROUND OF THE INVENTION

This application is based upon subject matters described in earlier filed and copending related applications and patents (see Related Applications above) which are specifically incorporated herein by reference.

SUMMARY OF THE INVENTION

I have now discovered novel gels with improved properties made from substantially random copolymers (pseudo-random copolymers or interpolymers) having polyethylene segments which can be crystallizable. The invention gels advantageously exhibit improved properties over gels made without such substantially random copolymers. The invention gels exhibit one or more property improvements, such as, higher tear resistances, greater fatigue resistance, increased tensile strength, improved damage tolerance, improved crack propagation resistance, improved resistance to high stress rupture, etc. Such improve gels are advantageous for end-use involving repeated applications of stress and strain resulting from large number of cycles of deformations, including compression, compression-extension (elongation), torsion, torsion-compression, torsion-elongation, tension, tension-compression, tension-torsion, and the like. Such improved properties makes the present invention gels advantageously and surprisingly exceptionally more suitable than gels of corresponding gel rigidities made from amorphous block copolymers such as poly(styrene-ethylene-butylene-styrene), poly(styrene-ethylene-propylene-styrene), high vinyl poly(styrene-ethylene-butylene-styrene), poly(styrene-ethylene-ethylene-butylene-styrene) alone.

An embodiment of the gel compositions and s of the invention comprises:

(I) 100 parts by weight of
(i) one or more poly(ethylene-styrene), interpolymers produced by metallocene catalysts, having one or more glassy components and at least one crystalizable polyethylene components, wherein said (i) copolymers being in combination with a selected amount of one or more selected second copolymers comprising:

(ii) one or more poly(ethylene-styrene), interpolymers, produced by metallocene catalysts, having one or more glassy components and one or more crystalizable polyethylene components of moderate crystallinity;

(iii) one or more poly(ethylene-styrene), interpolymers, produced by metallocene catalysts, having one or more glassy components and one or more crystalizable polyethylene components of low crystallinity;

(iv) one or more poly(ethylene-styrene), interpolymers, produced by metallocene catalysts, having one or more glassy components and one or more amorphous polyethylene components;

(v) one or more of a diblock, triblock, multi-arm block, branched block, radial block, or multiblock copolymers, wherein said (v) copolymers having one or more glassy components and one or more elastomeric components having polyethylene segments which can be crystallizable as to exhibit a crystallization exotherm by DSC curve; and (vi) one or more of a diblock, triblock, multi-arm block, branched block, radial block, or multiblock copolymers, wherein said (vi) copolymers having one or more glassy components and one or more amorphous elastomeric components;

(vii) a mixture of two or more (ii)–(vi) copolymers; wherein said (i), (ii), and (iii) copolymers having polyethylene segments which can be crystallizable as to exhibit a crystallization exotherm by DSC curve, (II) in combination with or without one or more of selected polymers or copolymers;

(III) a selected amount of one or more compatible plasticizers of sufficient amounts to achieve a stable gel having rigidities of from less than about 2 gram Bloom to about 1,800 gram Bloom; and in combination with or without.

(IV) a selected amount of at least one adhesion resins.

A further embodiment of the invention comprises: a gel composition comprising:

(i) 100 parts by weight of one or a mixture of two or more of a hydrogenated styrene isoprene/butadiene block copolymer(s), wherein said (i) block copolymers have the formula poly(styrene-ethylene-ethylene-propylene-styrene); from (ii) about 300 to about 1,600 parts by weight of a plasticizing oil; said gel composition characterized by a gel rigidity of from about 20 to about 1,800 gram Bloom; and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and in combination with or without (iv) a selected amount of one or more glassy component associating resins having softening points above about 120° C.

Another embodiment of the invention comprises: a gel composition comprising:

(i) 100 parts by weight of one or more poly(styrene-ethylene-ethylene-propylene-styrene) block copolymer(s); from (ii) about 300 to about 1,600 parts by weight of a plasticizing oil; said gel composition characterized by a gel rigidity of from about 20 to about 800 gram Bloom; and in combination with (iii) a selected amount of one or more block copolymers of poly(styrene-butadiene-styrene), poly(styrene-butadiene)$_n$, and poly(styrene-ethylene-butylene-styrene), wherein said selected copolymer is a linear, radial, star-shaped, branched or multiarm copolymer, wherein n is greater than one.

A further embodiment of the invention comprises: a gel composition comprising:

(i) 100 parts by weight of one or more poly(styrene-ethylene-ethylene-propylene-styrene) block copolymer(s);

(iii) a selected amount of one or more block copolymers of poly(styrene-butadiene-styrene), poly(styrene-butadiene)$_n$, poly(styrene-ethylene-propylene-styrene), and poly(styrene-ethylene-butylene-styrene), wherein said selected copolymer is a linear, radial, star-shaped, branched or multiarm copolymer, wherein n is greater than one;

(ii) about 300 to about 1,600 parts by weight of a plasticizing oil; said gel composition characterized by a gel rigidity of from about 20 to about 800 gram Bloom; and in combination with or without (iv) a selected amount of at least one adhesion resins.

Still another embodiment of the invention comprises: an adherent gel composition comprising:

(i) 100 parts by weight of one or a mixture of two or more of a hydrogenated styrene isoprene/butadiene block copolymer(s), wherein said (i) block copolymers have the formula poly(styrene-ethylene-butylene-styrene); from (ii) about 300 to about 1,600 parts by weight of a plasticizing oil; said gel composition characterized by a gel rigidity of from about 20 to about 800 gram Bloom; and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), low viscosity poly(styrene-ethylene-butylene-styrene), poly(styrene-ethylene-butylene), poly(styrene-ethylene propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and in combination with (iv) a minor amount of at least one or more adhesion resins.

As used herein, the term "gel rigidity" in gram Bloom is determined by the gram weight required to depress a gel a distance of 4 mm with a piston having a cross-sectional area of 1 square centimeter at 23° C.

The various aspects and advantages will become apparent to those skilled in the art upon consideration of the accompanying disclosure.

DESCRIPTION OF THE DRAWINGS

FIG. 1. Representative sectional view of gel, and gel articles.

FIGS. 8–14b. Illustrate embodiments of insulating gels and insulating gel composites.

FIGS. 15–16. Illustrate embodiments of insulating gels and insulating gel composites in cross-sectional views of foot wear.

FIGS. 18–19. Illustrate embodiments of insulating gels and insulating gel composites in cross-sectional views of foot wear.

FIG. 23. View of the human head.

FIGS. 24–28. Illustrate embodiments of the human head with insulating gel and insulating gel composite head-face-neck masks.

DESCRIPTION OF THE INVENTION

Figure 2A:
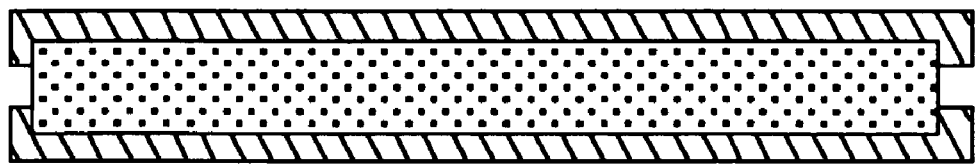
FIGS. 2a–2d. Representative sectional view of gel, and gel articles.
Figure 2B:
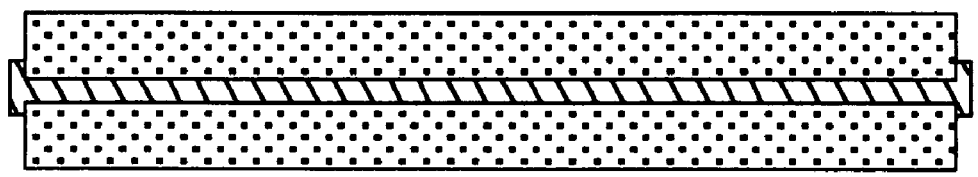
Figure 2C:
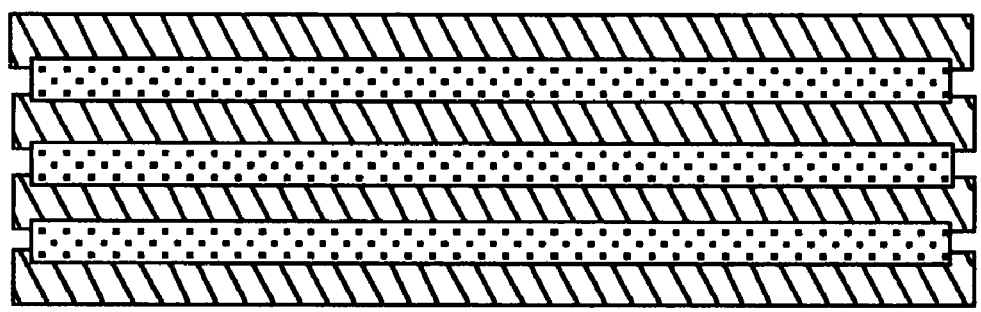
Figure 2D:
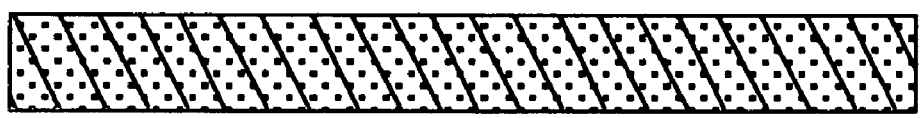
Figure 3A:
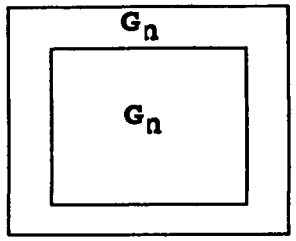
FIGS. 3a–3n. Representative sectional view of gel, and gel articles.
Figure 3B:
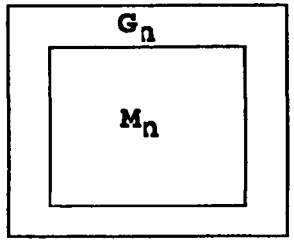
Figure 3C:
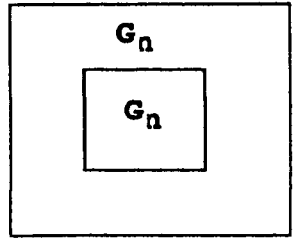
Figure 3D:
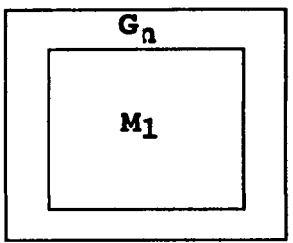
Figure 3E:
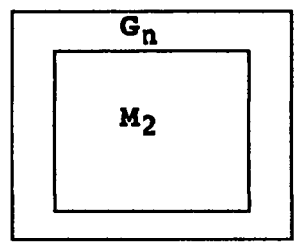
Figure 3F:
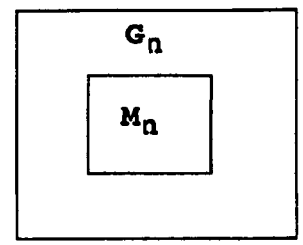
Figure 3G:
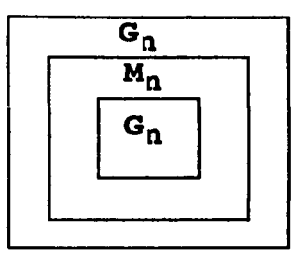
Figure 3H:
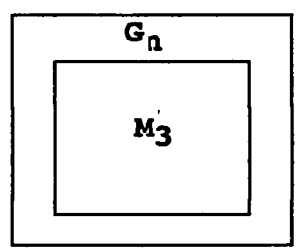
Figure 3I:
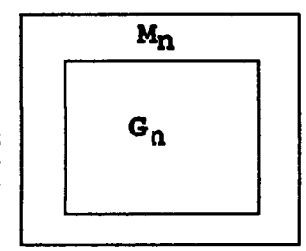
Figure 3J:
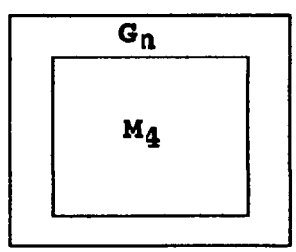
Figure 3K:
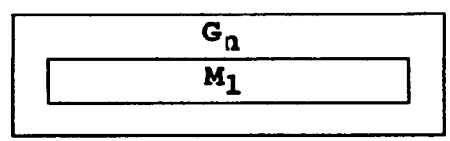
Figure 3L:
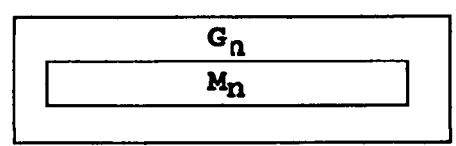
Figure 3M:
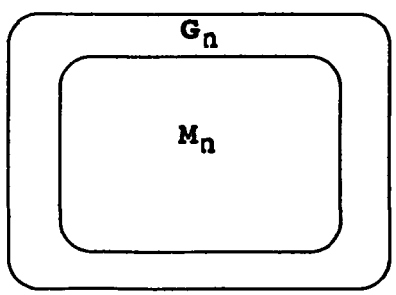
Figure 3N:
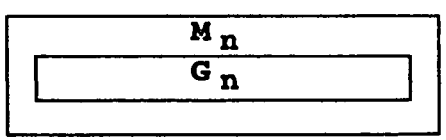
Figure 4A:
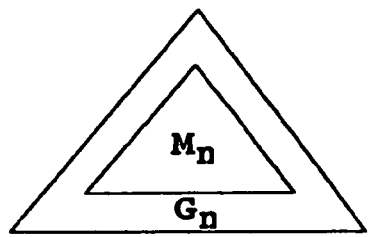
FIGS. 4a–4w. Representative sectional view of gel, and gel articles.
Figure 4B:
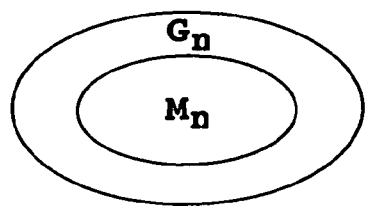
FIGS. 4x, 4y, 4z–7. Illustrate embodiments of insulating gels and insulating gel composites.
Figure 4C:
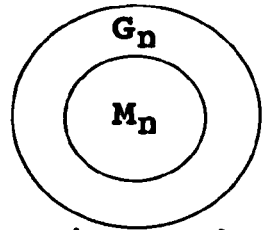
Figure 4D:
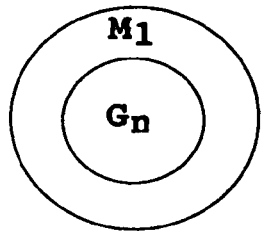
Figure 4E:
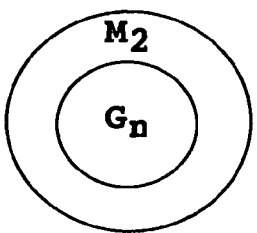
Figure 4F:
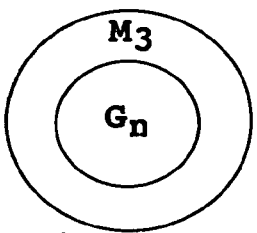
Figure 4G:
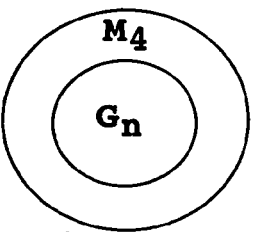
Figure 4H:
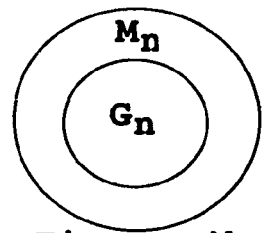
Figure 4I:
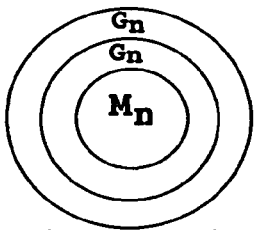
Figure 4J:
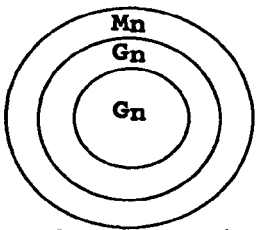
Figure 4K:
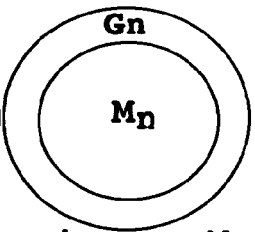
Figure 4L:
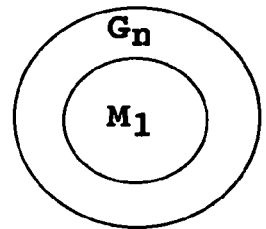
Figure 4M:
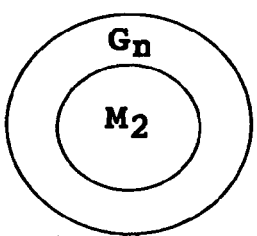
Figure 4N:
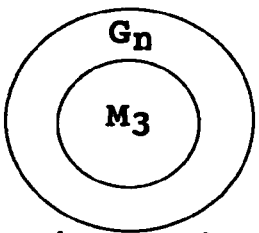
Figure 4O:
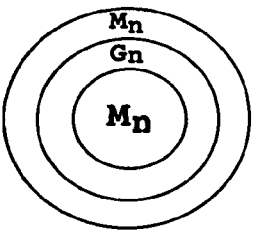
Figure 4P:
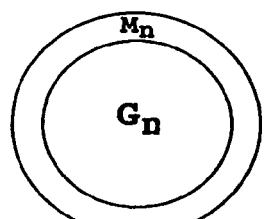
Figure 4Q:
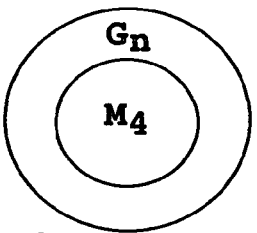
Figure 4R:
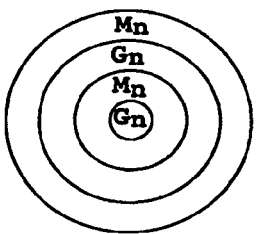
Figure 4S:
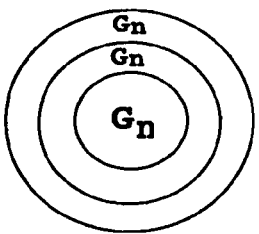
Figure 4T:
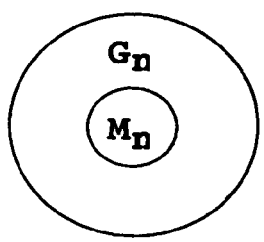
Figure 4U:
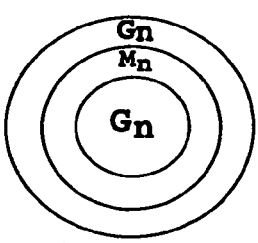
Figure 4V:
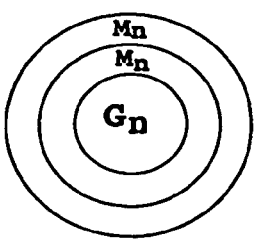
Figure 4W:
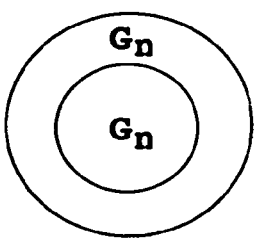
Figure 4X:
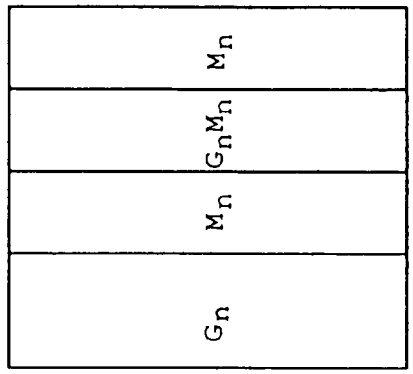
Figure 4Y:
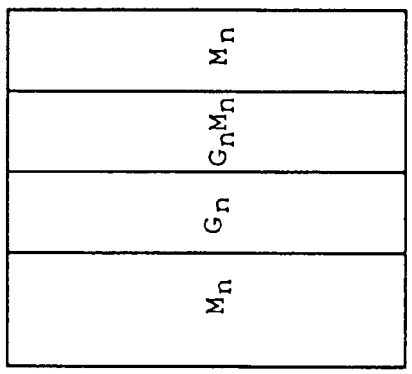
Figure 4Z:
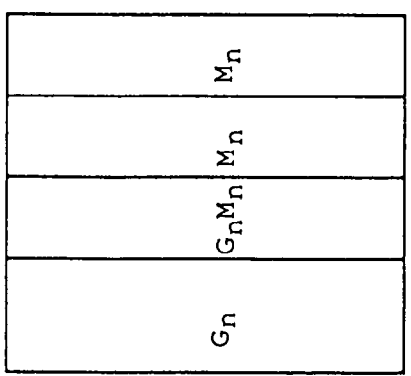

A interact search of the USPTO Patent Data Base of Applicant's published patent applications and issued patent describing gel compositions useful for fishing identified: 20020188057; U.S. Pat. Nos. 6,420,475, 6,161,555, 6,333, 374; 6,324,703; 6,148,830; 6,117,176; 6,050,871; 6,033, 283, 5,962,572, 5,938,499, 5,884,639, 8,597, 5,760,117, 5,655,947, 5,633,286, 5,508,334, 5,624,294, 5,508,334, 5,475,890, 5,336,708, 5,334,646; 5,324,222, 5,329,723, 5,262,468, 5,153,254, PCT/US97/17534, PCT/US94/04278 and PCT/US94/0731 which are incorporated herein by reference.

Block and other copolymers are described in the following publications:

(1) W. P. Gergen, "Uniqueness of Hydrogenated Block Copolymers for Elastomeric Applications," presented at the German Rubber Meeting, Wiesbaden, 1983; Kautsch, Gummi, Kunstst. 37, 284 (1984). (2) W. P. Gergen, et al., "Hydrogenated Block Copolymers," Paper No. 57, presented at a meeting of the Rubber Division ACS, Los Angeles, Apr. 25, 1985. Encyclopedia of Polymer Science and Engineering, Vol. 2, pp 324–434, "Block Copolymers". (3) L. Zotteri and et al., "Effect of hydrogenation on the elastic properties of poly(styrene-b-diene-b-styrene) copolymers", Polymer, 1978, Vol. 19, April. (4) J. Kenneth Craver, et al., Applied Polymer Science, Ch. 29, "Chemistry and Technology of Block Polymers", pp. 394–429, 1975. (5) Y. Mahajer and et al., "The influence of Molecular Geometry on the Mechanical Properties of homopolymers and Block Polymers of Hydrogenated Butadiene and Isoprene" reported under U.S. ARO Grant No. DAAG29-78-G-0201. (6) J. E. McGrath, et al ., "Linear and Star Branched Butadiene-Isoprene Block Copolymers and Their Hydrogenated Derivatives", Chem. Dept, Virginia Polytechnic Institute and State University Blacksturg, Va., reported work supported by Army Research Office. (7) Legge, Norman R. "Thermoplastic Elastomers", Charles Goodyear Medal address given at the 131st Meeting of the Rubber Division, American Chemical Society, Montreal, Quebec, Canada, Vol. 60, G79–G115, May 26–29, 1987. (8) Falk, John Carl, and et al., "Synthesis and Properties of Ethylene-Butylene-1 Block Copolymers", Macromolecules, Vol. 4, No. 2, pp. 152–154, March–April 1971. (9) Morton, Maurice, and et al., "Elastomeric Polydiene ABA Triblock Copolymers within Crystalline End Blocks", University of Arkon, work supported by Grant No. DMR78-09024 from the National Science Foundation and Shell Development Co. (10) Yee, A. F., and et al., "Modification of PS by S-EB-S Block Copolymers: Effect of Block Length", General Electric Corporate Research & Development, Schenectady, N.Y. 12301. (11) Siegfried, D. L., and et al., "Thermoplastic Interpenetrating Polymer Networks of a Triblock Copolymer elastomer and an Ionomeric Plastic Mechanical Behavior", Polymer Engineering and Science, January 1981, Vol. 21, No.1, pp 39–46. (12) Clair, D. J., "S-EB-S Copolymers Exhibit Improved Wax Compatibility", Adhesives Age, November, 1988. (13) Shell Chemical Technical Bulletin SC: 1102-89, "Kraton® Thermoplastic Rubbers in oil gels", April 1989. (14) Chung P. Park and George P. Clingerman, "Compatibilization of Polyethylene-Polystyrene Blends with Ethylene-Styrene Random Copolymers", the Dow Chemical Company, May 1996. (15) Steve Hoenig, Bob Turley and Bill Van Volkenburgh, "Material Properties and Applications of Ethylene-Styrene Interpolymers", the Dow Chemical Company, September 1996. (16) Y. Wilson Cheung and Martin J. Guest, "Structure, Thermal Transitions and Mechanical Properties of Ethylene/Styrene Copolymers", the Dow Chemical Company, May 1996. (17) Teresa Plumley Karjaia, Y. Wilson Cheung and Martin J. Guest, "Melt Rheology and Processability of Ethylene/Styrene Interpolymers", the Dow Chemical Company, May 1997. (18) D. C. Prevorsek, et al., "Origins of Damage Tolerance in Ultrastrong Polyethylene Fibers and s:, Journal of Polymer Science: Polymer Symposia No. 75,81–104 (1993). (19) Chen, H., et al, "Classification of Ethylene-Styrene Interpolymers Based on Comonomer Content", J. Appl. Polym. Sci., 1998, 70, 109. (20–24) U.S. Pat. Nos. 5,872,201; 5,460,818; 5,244,996; EP 415815A; JP07,278,230 describes substantially random, more appropriately presudo-random copolymers (interpolymers), methods of making and their uses. (25) Alizadeh, et al., "Effect of Topological Constraints on The Crystallization Behavior of Ethylene/alp[ha-Olefin Copolymers", PMSE, Vol, 81, pp. 248–249, Aug. 22–26, 1999. (26) Guest, et al., "Structure/Property Relationships of Semi-Crystalline Ethylene-Styrene Interpolymers (ESI)", PMSE, Vol, 81, pp. 371–372, Aug. 22–26, 1999. (27) A. Weill and R. Pixa, in Journal of Polymer Science Symposium, 58, 381–394 (1977), titled: "Styrene-diene Triblock Copolymers: Orientation Conditions and Mechanical Properties of the Oriented Materials" describe techniques of orientation of neat SIS and SBS block copolymers and their properties. (28) Elastomeric Thermoplastic, Vol. 5, pages 416–430; Block Copolymers, Vol. 2, pages 324; Block and Graft Copolymers; Styrene-Diene Block Copolymers, Vol. 15, pages 508–530; and Microphase Structure, can be found in ENCYCLOPEDIA OF POLYMER SCIENCE AND ENGINEERING, 1987. (29) Legge, N. R, et al., Chemistry and Technology of Block Polymers, Ch. 29, pages 394–429, ACS, Organic Coatings and Plastics Chemistry,® 1975. (30) Legge, N. R., Thermoplastic Elastomers, Rubber Chemistry and Technology, Vol. 60, pages G79–117. (31) Lindsay, G. A., et al., Morphology of Low Density Polyethylene/EPDM Blends Having Tensile Strength Synergism, source: unknown. (32) Cowie, J. M. G., et al., Effect of Casting on the Stress-Hardening and Stress-Softening Characteristics of Kraton-G 1650 Copolymer Films, J. Macromol. Sci.-Phys., B16(4), 611–632 (1979). (33) Futamura, S., et al., Effects of Center Block Structure on the Physical and Rheological Properties of ABA Block Copolymers. Part II. Rheological Properties, Polymer Engineering and Science, August, 1977, Vol. 17, No. 8, pages 563–569. (34) Kuraray Co., LTD. MSDS, Kuraray Septon 4055, Hydrogenated Styrene Isoprene/Butadiene Block Copolymer, Apr. 25, 1991. (35) Hoening, et al. U.S. Pat. No. 6,156,842, May 23, 2000, "Structures and fabricated articles having shape memory made from. Alpha.-olefin/vinyl or vinylidene aromatic and/or hindered aliphatic vinyl or vinylidene interpolymers. (36) Shell Technical bulletin SC: 1102-89 "Kraton® Thermoplastic Rubbers in oil gels", April 1989. (37) Witco products literature #19610M 700–360: "White oils Petroleum, Microcrystalline Waxes, Petroleum Distillates", 1996 Witco Corporation. (38) Witco presentation: "White Mineral Oils in Thermoplastic Elastomers", ANTEC 2002, May 5–8, 2002. (39) Lyondell literature LPC-8126 1/93, "Product Descriptions of White Mineral Oils", pp 30–33. (40) Collins, Jr., Henry Hill, 'COMPLETE FIELD GUIDE TO AMERICAN WILDLIFE", 1959, LCCN: 58-8880. (41) Romanack, Mark, Bassin' with the Pros, 2001, LCCN: 2001086512. (42) Salamone, Joseph C., Concise Polymeric Materials Encyclopedia, CRC Press, 1999. (43) Lide, David R., Handbook of Chemistry and Physics, CRC Press, 78th Edition, 1997–1998. (44) Sigma year 2002–2003 Biochemical and Reagents for life Science Research, sigma-aldrich.com. (45) Kraton Polymers and Compounds, Typical Properties Guide, K0137 Brc-00U, 2001. (46) Kraton Thermoplastic Rubber, Typical properties 1988, SC: 68–78, 5/88 5M. (47) Humko chemical Product Guide, Witco 1988. (48) Opportunities with Humko chemical Kemamide fatty amides, Witco 1987. The above applications, patents and publications are specifically incorporated herein by reference. (49) J. C. Randall, "A Review of High Resolution Liquid 13Carbon Nuclear Magnetic Resonance Characterizations of Ethylene-Based Polymers" JMS—Review Macromol. Chem. Phys., C29 (2 & 3), 201–317 (1989). (50) Silipos product catalogue Page 7 for Single Sock Gel Liner (with respect to Product sales dates: #1272 on or about Jan. 31, 1995, #1275 on or about Jan. 31, 1995, and #1276 same as #1272 but a different size on or about Dec. 31, 1994). (51) "SiloLiner" Sales literature from Knit-Rite medical (Mar. 1, 1999 3pp.). (52) ALPS South Corporation—Gel Liners: NEW! Easy Liner ELPX, ELDT and ELFR published fact sheet on the Internet on Aug. 10, 1999.

Legge's paper teaches the development of (conventional substantially amorphous elastomer mid segment) SEBS triblock copolymers. In the polymerization of butadiene by alkylithium initiators, 1,4-addition or 1,2-addition polymers, mixtures, can be obtained. In forming styrene butadiene triblock copolymers involving the addition of solvating agents such as ethers just before the final styrene charge is added, any excess of ethers can alter the polybutadiene structure from a 1,4-cis or trans structure to a 1,2- or 3,4-addition polymer. Using difunctional coupling agent would give linear block copolymers and multifuntional agents would give star-shaped or radial block copolymers. Hydrogenation of the 1,4-polybutadiene structure yields polyethylene, while that of the 1,2-polybutadiene yields polybutylene. The resulting polyethylene will be essentially identical with linear, high-density polyethylene with a melting point, Tm, of about 136° C. Hydrogenation of 1,2-polybutadiene would yield atactic poly(1-butene) (polybutylene). The Tg of polybutylene is around −18° C. Random mixtures of ethylene and butylene units in the chain would suppress crystallinity arising from polyethylene sequences. The objective for a good elastomer should be to obtain a saturated olefin elastomeric segment with the lowest possible Tg and the best elastomeric properties. Such an elastomer favored using styrene as the hard-block monomer and selecting the best monomer for hydrogenation of the elastomer mid segment. Using a mixture of 1,4-and 1,2-polybutadiene as the base polymer for the mid segment would result in an ethylene/butylene mid segment in the final product. The elements of selection of the midsegment composition is elastomer crystallinity and the elastomer Tg of an ethylene/butylene copolymer. Very low levels of crystallinity can be achieved around 40–50% butylene concentration. The minimum in dynamic hysteresis around 35% butylene concentration in the elastomeric copolymer. A value of 40% butylene concentration in the ethylene/butylene midsegment was chosen for the S-EB-S block copolymers. Clair's paper teaches that the EB midblock of conventional S-EB-S polymers is a random copolymer of ethylene and 1-butene exhibiting nearly no crystallinity in the midblock. In the preparation of ethylene-butylene (EB) copolymers, the relative proportions of ethylene and butylene in the EB copolymer chain can be controlled over a broad range from almost all ethylene to almost all butylene. When the EB copolymer is nearly all ethylene, the methylene sequences will crystallize exhibiting properties similar to low density polyethylene. In differential scanning calorimeter (DSC) curves, the melting endotherm is seen on heating and a sharp crystallization exotherm is seen on cooling. As the amount of butylene in the EB copolymer is increased, the methylene sequences are interrupted by the ethyl side chains which shorten the methylene sequences length so as to reduce the amount of crystallinity in the EB copolymer. In conventional S-EB-S polymers, the amount of 1-butene is controlled at a high enough level to make the EB copolymer midblock almost totally amorphous so as to make the copolymer rubbery and soluble in hydrocarbon solvents. Clair suggests that an S-EB-S polymer retaining at least some crystallinity in the EB copolymer midblock may be desirable. Therefore, a new family of S-EB-S polymers are developed (U.S. Pat. No. 3,772,234) in which the midblock contains a higher percentage of ethylene. The molecular weights of the new crystalline midblock segment S-EB-S polymers can vary from low molecular weight, intermediate molecular, to high molecular weight; these are designated Shell GR-3, GR-1, and GR-2 respectively. Unexpectly, the highest molecular weight polymer, GR-2 exhibits an anomalously low softening point. A broad melting endotherm is seen in the DSC curves of these polymers. The maximum in this broad endotherm occurs at about 40° C. Himes, et al., (U.S. Pat. No. 4,880,878) describes SEBS blends with improved resistance to oil absorption. Papers (14)–(17) describes poly (ethylene styrene) substantially random copolymers (Dow Interpolymers™): Dow S, M and E Series produced by metallocene catalysts, using single site, constrained geometry addition polymerization catalysts resulting in poly(ethylene-styrene) substantially random copolymers with weight average molecular weight (Mw) typically in the range of $1 \times 10^5$ to $4 \times 10^5$, and molecular weight distributions (Mw/Mn) in the range of 2 to 5. Paper (18) Prevorsek, et al., using Raman spectroscopy, WAXS, SAXD, and EM analysis interprets damage tolerance of ultrastrong PE fibers attributed to the nano scale structure that consists of needle-like-nearly perfect crystals that are covalently bonded to a rubbery matrix with a structure remarkably similar to the structure of NACRE of abalone shells which explains the damage tolerance and impact resistance of PE fibers. PE because of its unique small repeating unit, chain flexibility, ability to undergo solid state transformation of the crystalline phase without breaking primary bonds, and its low glass transition temperature which are responsible for large strain rate effects plays a key role in the damage tolerance and fatigue resistance of structures made of PE fibers. Chen (19) classifies 3 distinct categories of E (approximately 20–50 wt % styrene), M (approximately 50–70 wt % styrene), & S (greater than approximately 70 wt % styrene) substantially random or more appropriately pseudo-random ethylene-styrene copolymers or random copolymers of ethylene and ethylene-styrene dyads. The designated Ethylene-styrene copolymers are: E copolymers (ES16, ES24, ES27, ES28, ES28, ES30, and ES44 with styrene wt % of 15.7, 23.7, 27.3, 28.1, 39.6 & 43.9 respectively), M copolymers (ES53, ES58, ES62, ES63, and ES69 with styrene wt % of 52.5, 58.1, 62.7, 62.8, and 69.2 respectively and crystallinity, %, DSC, based on copolymer of 37.5, 26.6, 17.4, 22.9, 19.6 and 5.0 respectively), S copolymers (ES72, ES73, and ES74 with styrene wt % of 72.7, 72.8, and 74.3 respectively). The maximum comonomer content for crystallization of about 20% is similar in other ethylene copolymers, such as in ethylene-hexene and ethylene-vinyl acetate copolymers. If the comonomer can enter the crystal lattice, such as in ethylene-propylene, compositions in excess of 20 mol % comonomer can exhibit crystallinity. The molecular weight distribution of these copolymers is narrow, and the comonomer distribution is homogeneous. These copolymers exhibit high crystalline, lamellar morphologies to fringed micellar morphologies of low crystallinity. Crystallinity is determined by DSC measurements using a Rheometric DSC. Specimens weighing between 5 and 10 mg are heated from −80 to 180° C. at a rate of 10° C./min (first heating), held at 190° C. for 3 min, cooled to −80° C. at 10° C./min, held at −80° C. for 3 min, and reheated from +80° C. to 180° C. at 10° C./min (second heating). The crystallinity (wt %) is calculated from the second heating using a heat of fusion of 290 J/g for the polyethylene crystal. Contributing effects of the crystallinity include decrease volume fraction of the amorphous phase, restricted mobility of the amorphous chain segments by the crystalline domains, and higher styrene content of the amorphous phase due to segregation of styrene into the amorphous phase. Table I of this paper shows values of Total Styrene (wt %), aPS (wt %), Styrene (wt %), Styrene (mol %), $10^{-3}$Mw, Mw/Mn, and Talc (wt %) for Ethylene-styrene copolymers ES16–ES74 while FIGS. 1–12 of this paper shows: (1) melting thermograms of ESI 1st and 2nd heating for ES16, ES27, ES44, ES53, ES63, & ES74; (2) crystallinity from DSC as a function of conmonomer content; (3) Logarithmic plot of the DSC heat of melting vs. Mole % ethylene for ESIs; (4) measured density as a function of styrene content for semicrystalline and amorphous ESIs; (5) % crystallinity from density vs % crystallinity from DSC melting enthalpy; (6) Dynamic mechanical relaxation behavior; (7) Glass transition temperature as a function of wt % ethylene-styrene dyads for senicrystalline and amorphous ESIs; (8) Arrhenius plots of the loss tangent peak temperature for representative semicrystalline and amorphous ESIs; (9) Draw ratio vs engineering strain; (10) Engineering stress-strain curves at 3 strain rates for ES27, ES63 and ES74; (11) Engineering stress-strain curves of ESIs; (12) Classification scheme of ESIs based on composition. (20) U.S. Pat. No. 5,872,201 describes interpolymers: terpolymers of ethylene/styrene/propylene, ethylene/styrene/4-methyl-1-pentene, ethylene/styrene/hexend-1, ethylene/styrene/octene-1, and ethylene/styrene/norbornene with number average molecular weight (Mn) of from 1,000 to 500,000. (21–24) U.S. Pat. Nos. 5,460,818; 5,244,996; EP 415815A; JP07,278,230 describes substantially random, more appropriately presudo-ramdom copolymers (interpolymers), methods of making and their uses. (25) Alizadeh, et al., find the styrene interpolymers impedes the crystallization of shorter ethylene crystallizable sequences and that two distinct morphological features (lamellae and fringe micellar or clain clusters) are observed in ethylene/styrene (3.4 mol %) as lamella crystals organized in stacks coexisting with interlamellar bridge-like structures. (26) Guest, et al., describes ethylene-styrene copolymers having less than about 45 wt % copolymer styrene being sernicrystalline, as evidenced by a melting endotherm in DSC testing (Dupont DSC-901,10° C./min) data from the second heating curve. Crystallization decreases with increasing styrene content. Based on steric hindrance, styrene unit is excluded from the crystalline region of the copolymers. Transition from semi-crystalline to amorphous solid-state occurs at about 45 to 50 wt % styrene. At low styrene contents (<40%), the copolymers exhibit a relatively well-defined melting process. FIGS. 1–5 of this paper shows (a) DSC data in the T range associated with the melting transition for a range of ESI differing primarily in copolymer styrene content, (b) variation in percent crystallinity (DSC) for ESI as a function of copolymer S content, (c) elastic modulus versus T for selected ESI differing in S content, (d) loss modulus versus T for selected ESI differing in S content, (e) Tensile stress/ strain behavior of ESI differing in S content, respectively. (35) Hoening, et al, teaches preparation of interpolymers ESI #1 to #38 having number average molecular weight (Mn) greater than about 1000, from about 5,000 to about 500,000, more specifically from about 10,000 to about 300,000. The above patents and publications are specifically incorporated herein by reference.

In general, the overall physical properties of amorphous gels are better at higher gel rigidities. The amorphous gels, however, can fail catastrophically when cut or notched while under applied forces of high dynamic and static deformations, such as extreme compression, torsion, high tension, high elongation, and the like. Additionally, the development of cracks or crazes resulting from a large number of deformation cycles can induce catastrophic fatigue failure of amorphous gel s, such as tears and rips between the surfaces of the amorphous gel and substrates or at the interfaces of interlocking material(s) and gel. Consequently, such amorphous gels are inadequate for the most demanding applications involving endurance at high stress and strain levels over an extended period of time.

The various types of copolymers and block copolymers employed in forming the crystal-gels of the invention are of the general configurations $(Y-AY)_n$ copolymers, A-Z-A, and $(A-Z)_n$ block copolymers, wherein the subscript n is a number of two or greater. In the case of multiarm block copolymers where n is 2, the block copolymer denoted by $(A-Z)_n$ is A-Z-A. It is understood that the coupling agent is ignored for sake of simplicity in the description of the $(A-Z)_n$ block copolymers.

The segment (A) comprises a glassy amorphous polymer end block segment which can be polystyrene, poly(alpha-methylstyrene), poly(o-methylstyrene), poly(m-methylstryene), poly(p-methylstyrene) and the like, preferably, polystyrene.

The segment (Y) of copolymers $(Y-AY)_n$ comprises crystalizable poly(ethylene) (simply denoted by "-E-"or (E)). In the case of copolymers $(A-Y)_n$, (Y) when next to (A) may be substantially non-crystalline or amorphous ethylene segments. For example a crystalizable copolymer $(Y-AY)_n$ may be represented by: . . . -E-E-E-E-E-E-E-E-E-SE-E-E-E-E-E-E-SE-E-E-E-E-E-SE- . . . Where Y is a long run of polyethylene or a non-crystalline copolymer $(AY-AY)_n$: . . . -E-SE-SE-E-SE-E-SE-E-SE-E-E-SE-SE-E-SE- . . . , where Y is a non-crystalline run of ethylene.

Other substantially random copolymers suitable for forming invention gels of the invention include (Y-A-Y') where Y is a crystalizable run of ethylene and Y' can be propylene, 4-methyl-1-pentene, hexene-1, octene-1, and norborene. A can be styrene, vinyl toluene, alpha-methylstyrene, t-butyl-styrene, chlorostyrene, including isomers and the like. Examples are: poly(ethylene-styrene) (ES), poly(ethylene-styrene-propylene) (ESP), poly(ethylene-styrene-4-methyl-1-pentene) (ES4M1P), poly(ethylene-styrene-hexend-1) (ESH1), poly(ethylene-styrene-octene-1) (ESO1), and poly (ethylene-styrene-norborene) (ESN), poly(ethylene-alpha-methylstyrene-propylene), poly(ethylene-alpha-methylstyrene-4-methyl-1-pentene), poly(ethylene-alpha-methylstyrene-hexend-1), poly(ethylene-alpha-methylstyrene-octene-1), and poly(ethylene-alpha-methylstyrene-norborene) and the like.

The end block segment (A) comprises a glassy amorphous polymer end block segment which can be polystyrene, poly(alpha-methylstyrene), poly(o-methylstyrene), poly(m-methylstryene), poly(p-methylstyrene) and the like, preferably, polystyrene. The segment (Y) of random copolymers A-Y comprises crystalizable poly(ethylene) (simply denoted by "-E-" or (E)). In the case of random copolymers A-Y, (Y) may be substantially non-crystalline or amorphous ethylene segments. The midblocks (Z) comprises one or more midblocks of crystalizable poly(ethylene) (simply denoted by "-E- or (E)") with or without one or more amorphous midblocks of poly(butylene), poly(ethylene-butylene), poly (ethylene-propylene) or combination thereof (the amorphous midblocks are denoted by "-B- or (B)", "-EB- or (EB)", and "-EP- or (EP)" respectively or simply denoted by "-W- or (W)" when referring to one or more of the amorphous midblocks as a group) The A and Z, and A and Y portions are incompatible and form a two or more-phase system consisting of sub-micron amorphous glassy domains (A) interconnected by (Z) or (Y) chains. The glassy domains serve to crosslink and reinforce the structure. The number average molecular weight (Mn) of the random copolymers is preferably greater than 1,000, advantageously from about 5,000 to about 1,100,000, more advantageously from abut 8,000 to about 700,000. Examples are:

The method of making Y-A-Y and Y-A-Y' random copolymers by metallocene single site catalysts are described in U.S. Pat. Nos. 5,871,201, 5,470,993, 5,055,438, 5,057,475, 5,096,867, 5,064,802, 5,132,380, 5,189,192, 5,321,106, 5,347,024, 5,350,723, 5,374,696, 5,399,635, and 5,556,928, 5,244,996, application EP-A-0416815, EP-A-514828, EP-A-520732, WO 94/00500 all of which disclosure are incorporated herein by reference.

The linear block copolymers are characterized as having a Brookfield Viscosity value at 5 weight percent solids solution in toluene at 30° C. of from less than about 40 cps to about 60 cps and higher, advantageously from about 40 cps to about 160 cps and higher, more advantageously from about 50 cps to about 180 cps and higher, still more advantageously from about 70 cps to about 210 cps and higher, and even more advantageously from about 90 cps to about 380 cps and higher.

The branched, star-shaped (radial), or multiarm block copolymers are characterized as having a Brookfield Viscosity value at 5 weight percent solids solution in toluene at 30° C. of from about 80 cps to about 380 cps and higher, advantageously from about 150 cps to about 260 cps and higher, more advantageously from about 200 cps to about 580 cps and higher, and still more advantageously from about 100 cps to about 800 cps and higher.

The poly(ethylene/styrene) copolymers, type S series has more than 50 wt % styrene and is glassy at short times and rubbery at long times and exhibits ambient Tg, melt density of about higher than 0.952 to about 0.929 and less, typical Mw=about less than 150,000 to 350,000 and higher.

The type M series has more than 50 wt % styrene is amorphous rubber and exhibits very low modulus, high elasticity, low Tg of from greater than 10° C. to less than −50° C., melt Index of from higher than 5 to less than about 0.1, melt density of higher than 0.93 to 9.0 and less, typical Mw=about less than 200,000 to 300,000 and higher.

The type E series contains up to 50 wt % styrene is semi-crystalline rubber and exhibits low Tg of from greater than 0° C. to about less than −70, low modulus semi-crystalline, good compression set, Melt Index of from about higher than 2 to less than 0.03, melt density of about higher than 0.90 to 0.805 and less, Mw=about less than 250,000 to 350,000 and higher.

The E series random copolymers can be blended with the type M and type S series copolymers (having high glassy components) and one or more of the i, ii, iii, iv, v, vii and viii copolymers, plasticizers to form crystalizable polymer invention gels of the invention.

This physical elastomeric network structure is reversible, and heating the polymer above the softening point of the glassy domains temporarily disrupt the structure, which can be restored by lowering the temperature. During mixing and heating in the presence of compatible plasticizers, the glassy domains (A) unlock due to both heating and solvation and the molecules are free to move when shear is applied. The disruption and ordering of the glassy domains can be viewed as a unlocking and locking of the elastomeric network structure. At equilibrium, the domain structure or morphology as a function of the (A) and (Z) or (A) and (Y) phases (mesophases) can take the form of spheres, cylinders, lamellae, or bicontinous structures. The scale of separation of the phases are typically of the order of hundreds of angstroms, depending upon molecular weights (i.e. Radii of gyration) of the minority-component segments. The sub-micron glassy domains which provides the physical interlocking are too small to see with the human eye, too small to see using the highest power optical microscope and only adequately enough to see using the electron microscope. At such small domain scales, when the gel is in the molten state while heated and brought into contact to be formed with any substrate and allowed to cool, the glassy domains of the gel become interlocked with the surface of the substrate. At sufficiently high enough temperatures, with or without the aid of other glassy resins (such as polystyrene homopolymers and the like), the glassy domains of the copolymers forming the gels fusses and interlocks with even a visibly smooth substrate surface such as glass. The disruption of the sub-micron domains due to heating above the softening point forces the glassy domains to open up, unlocking the network structure and flow. Upon cooling below the softing point, the glassy polymers reforms together into sub-micron domains, locking into a network structure once again, resisting flow. It is this unlocking and locking of the network structure on the sub-micron scale with the surfaces of various materials which allows the gel to form interlocking s with other materials.

A useful analogy is to consider the melting and freezing of a water saturated substrate, for example, foam, cloth, fabric, paper, fibers, plastic, concrete, and the like. When the water is frozen, the ice is to a great extent interlocked with the substrate and upon heating the water is able to flow. Furthermore, the interlocking of the ice with the various substrates on close examination involves interconnecting ice in, around, and about the substrates thereby interlocking the ice with the substrates. A further analogy, but still useful is a plant or weed well established in soil, the fine roots of the plant spreads out and interconnects and forms a physical interlocking of the soil with the plant roots which in many instances is not possible to pull out the plant or weed from the ground without removing the surrounding soil also.

Likewise, because the glassy domains are typically about 200 Angstroms in diameter, the physical interlocking involve domains small enough to fit into and lock with the smallest surface irregularities, as well as, flow into and flow through the smallest size openings of a porous substrate. Once the gel comes into contacts with the surface irregularities or penetrates the substrate and solidifies, it becomes difficult or impossible to separate it from the substrate because of the physical interlocking. When pulling the gel off a substrate, most often the physically interlocked gel remains on the substrate. Even a surface which may appear perfectly smooth to the eye, it is often not the case. Examination by microscopy, especially electron microscopy, will show serious irregularities. Such irregularities can be the source of physical interlocking with the gel.

Such interlocking with many different materials produce gel s having many uses including forming useful composites. The gel compositions is denoted as "G" can be physically interlocked or formed in contact with a selected material denoted as "M" denoted for simplicity by their combinations $G_nM_n$, $G_nM_nG_n$, $M_nG_nM_n$, $M_nG_nG_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nM_nM_nG_n$, $G_nG_nM_nM_n$, $G_nG_nM_nG_nM_n$, $G_nM_nG_nG_nG_nM_n$, $G_nM_nG_nM_nM_n$, $M_nG_nM_nG_nM_nG_n$, $G_nG_nM_nM_nG_n$, $G_nG_nM_nG_nM_nG_n$, and the like or any of theirpermutations of one or more $G_n$ with $M_n$ and the like, wherein when n is a subscript of M, n is the same or dif selected from the group consisting of foam, plastic, fabric, metal, concrete, wood, glass, ceramics, synthetic resin, synthetic fibers or refractory materials and the like; wherein when n is a subscript of G, n denotes the same or a different gel rigidity of from about 20 to about 800 gram Bloom). The gel compositions and articles of the composites are formed from I, II, and III components described above.

Sandwiches of invention gel-material (i.e., invention gel-material-invention gel or material-invention gel-material, etc.) are useful as dental floss, shock absorbers, acoustical isolators, vibration dampers, vibration isolators, and wrappers. For example the vibration isolators can be use under research microscopes, office equipment, tables, and the like to remove background vibrations. The tear resistance nature of the invention gels are superior in performance to amorphous block copolymer gels which are much less resistance to crack propagation caused by long term continue dynamic loadings.

The high tear resistant soft invention gels are advantageously suitable for a safer impact deployable air bag cushions, other uses include: toys; games; novelty, or souvenir items; elastomeric lenses, light conducing articles, optical fiber connectors; athletic and sports equipment and articles; medical equipment and articles including derma use and for the examination of or use in normal or natural body orifices, health care articles; artist materials and models, special effects; articles designed for individual personal care, including occupational therapy, psychiatric, orthopedic, podiatric, prosthetic, orthodontic and dental care; apparel or other items for wear by and on individuals including insulating gels of the cold weather wear such as boots, face mask, gloves, full body wear, and the like have as an essential, direct contact with the skin of the body capable of substantially preventing, controlling or selectively facilitating the production of moisture from selected parts of the skin of the body such as the forehead, neck, foot, underarm, etc; cushions, bedding, pillows, paddings and bandages for comfort or to prevent personal injury to persons or animals; housewares and luggage; articles useful in telecommunication, utility, industrial and food processing, and the like as further described herein.

Cushion in the form of crumpets can be formed by utilizing the aeration method described in U.S. Pat. No. 4,240,905 (which is incorporated herein by reference) instead of high solids, inert gas is introduced through a multi holed mold base at positive pressure depending on the working viscosity of the molten invention gel and gel blends without repeatedly shearing the rising injected gas streams thereby forming cushions having natural structures similar to crumpets upon cooling in the mold. Also long metal netting needles of any desired diameter are projected through multi holed mold base, top and side walls in various directions creating a multi directional hollowed network when molten gel is injected, poured, or transferred into the enclosed mold under positive pressure and allowed to cool The needles are easily removed one by one or altogether at once leaving the described multi channeled gel cushion. Likewise the inert gas injected into a gel body while in the molten state can be sheared at desired time intervals so as to provide hollowed cushions with any desired void shaped volumes. A crumpet looks like a shaped volume with a smooth bottom and side containing many small holes a few millimeter in diameter which holes are extended from near the bottom to the top of the crumpet, Health care devices such as face masks for treatment of sleep disorder require non-tacky invention gels of the invention. The invention gel 3 forming a gel overlap 7 portion on the face cup 1 at its edge 12 conforming to the face and serve to provide comfort and maintain partial air or oxygen pressure when worn on the face during sleep. Other health case uses include pads in contact with the body use in wound healing and burn treatment, the gel can also be use as a needle protector sheath, tubing for medical fluid sets, as male and female connectors, sealing caps, a pad use for compression at needle injection site to prevent injury to the blood vessel.

When utilized as a needle protector sheath, a invention gel composition made from SEEPS in combination with or without other polymers, and copolymers is of advantage because of its higher rupture tear resistance properties. SEBS and SEPS in combination with low viscosity SEBS can also be use to advantage, but with a noticeable decrease in rupture resistance. The needle can be secured by forcing the sharp point into the gel volume of a desired shaped gel body. In doing so, automatically the sharped needle is secured safely within the gel body preventing the sharp needle from accidently injuring the health worker or anyone else in contact with the needle device. Moreover, the liquid be it medication or body fluids are also securely and safely contained in the gel body. The gel automatically plug the tip of the sharp needle so as to prevent any liquid from leaving the tip of the needle. Moreover the gel body containing the needle can be in safe contact when accidently placed on or near a body while work is being performed. The holding power or force holding the sharp needle can be adjusted by formulating the gel to any desired rigidity. The greater the rigidity, the greater the holding force of the gel on the needle. Such needle can be inserted into a gel body at any desired angle from less than 1° to less than 180° without loss of holding force on the needle. The gel needle protector sheath can be any desired size. A large grip size is useful so as not to readily misguide the needle into the gel body. A small size is useful so as not to be too bulky for storage. The requirement of the gel body as a needle sheath protector is that when drop from a height of 3 feet or 1 meter, the needle should not be able to penetrate through the gel body adjacent to the tip, thereby maintaining integrity of the seal and afford adequate protection to medical workers. The other requirement is that the gel body should have sufficient holding force gripping the needle while it rest within the gel body that it does not easily slip out accidently. Such force can be selected to be greater than the weight of the needle and attached instrument the needle is physically attached. A rigidity in gram Bloom of greater than 100 gram is desirable for gripping the needle and hold it in place. Higher rigidity are of advantage, such as 100, 200, 300, 400, 500, 600, 800,1000, 2000, and higher.

Connectors, such as luer lock connectors, friction fit connectors, or other types of connectors for blood tubing especially useful for dialysis including use in connecting blood sets, hemodialysis tube sets, bubble trap inlet and outlet tubing, closures, caps and the like can be contaminated easily. A not so general information is that medical works do not take the time to decontaminate or safe guard connectors. The connectors are plug in and unplugged when needed and almost no one see to the cleanliness of the connectors before plug the connectors together, there is just no time for it. The need to plug and unplug connectors in the health service environment is that the connectors come in two types: male and female use to make every connection and the male and female parts come separately because at the time of manufacture they are made separately. The invention gel of high rigidity made from gel compositions of 250 to 400 parts by weight of block copolymers are useful for making tubing and tubing connectors. Surprisingly, if a male mold is use to made the male connector part, the male connector part can be allowed to cool in the mold and the same mold holding the male connector part can than be injected with additional gel of suitable rigidity to form the opposite female part. When the mold containing the male and female connector parts are cooled sufficient, both male and female connectors are demoted at the same time and packaged without contamination. The connectors can be molded with the same gel material tubing or if molded separately, the connectors need not be taken apart until needed. The novelty is that when the invention gels are sufficiently cooled to above room temperature, a second and followed by a third and the like molten gel can be in contact with the cooled gel and when both have cooled sufficiently the two parts will come apart. They do not bond in any way. Therefore a gel article negative can receive molten gel utilizing the negative gel to form a positive. This reduces the cost of making two molds, a positive and a negative. Only one is necessary to make both parts.

Tacky gels because of its tactile feel are undesirable for such applications while other application require gel adhesion to the skin and selected substrates. Gels are inherently sticky or tacky to the touch, especially soft thermoplastic elastomer oil gels which can exhibit extreme tackiness when compounded with high viscosity oils. The tackiness can be reduced, masked or removed by powdering the gel's outside surface or by incorporating additives which will eventually migrate to the gel's outer surface. Such additives being effective only at the gel's surface. The migration of additives from within the bulk gel to the gel's surface is generally due to gradients of pressure or temperature, weak, moderate, or strong molecular dipo/dipo or dipo/non-dipo interactions within the gel. The additives, however, can cause the gels to be translucent or opaque throughout their volume as found in my U.S. Pat. No. 5,760,117 which describes surface activated non-tacky gels. Once the additives are transported from within the gel to the surface forming an "additive layer". Although the additive layer can reduced tackiness or no tack at the gel's surface, the additive layer can themselves impart their own tactical character. For example, stearic acid exhibits a low melting point and tends to be somewhat greasy at ambient or above ambient temperatures. Once the gel is damaged or cut, the tackiness of the freshly cut area is exposed.

Stearic acid and other additives such as certain organic crystals will melt upon heating and reform into crystals within the gel and may bloom to the gel surface as described in my U.S. Pat. No. 6,420,475. Selected substances blended into a gel will eventually find its way from the interior of the bulk gel to its surface by means of migration due to gradient transport (bloom to the surface with time depending on the nature of the added substances).

As use herein, the tack level in terms of "Gram Tack" is determined by the gram weight displacement force to lift a polystyrene reference surface by the tip of a 16 mm diameter hemi-spherical gel probe in contact with said reference surface as measured on a scale at 23° C. (about STP conditions).

As used herein, the term "gel rigidity" in gram Bloom is determined by the gram weight required to depress a gel a distance of 4 mm with a piston having a cross-sectional area of 1 square centimeter at 23° C.

The gelatinous elastomer compositions of the present invention can be made firm or soft, tacky, adherent or non-tacky to the touch. The "non-tacky to the touch" gelatinous elastomer compositions of the invention is not based on additives which bloom to the surface to reduce tack. For simplicity, the gelatinous elastomer compositions of the invention (which are highly tear resistant and rupture resistant and can be made tacky, adherent, non-tacky to the touch and optically transparent or clear) will be referred to herein as "invention gel(s)" which includes "tear resistant gels", "rupture resistant gels", "non-tacky gels", "no tack gels", "optical gels", "tacky gels", "adherent gels", and the like when referring to certain property attributes of the various gels or more simply refer to as "the gel(s)" or "said gel(s)". Gels of the invention are described herein below for every use.

As described herein, the conventional term "major" means greater than 50 parts by weight and higher (e.g. 5.01, 50.2, 50.3, 50.4, 50.5, . . . 51, 52, 53, 54, 55, 56, 57, 58, 59, 60, 61, 62, 63, 64, 65, 66, 67, 68, 69, . . . 580 and higher based on 100 part by weight of (I) copolymers) and the term "minor" means 49.99 parts by weight and lower (e.g. 49, 48, 47, 46, 45, 44, 43, 42, 41, 40, 39, 38, 37, 36, 35, 34, 33, 32, 21, . . . 10, 9, 8, 7, 6, 5, 4, 3, 2, 1, 0.9, 0.8, 0.7 . . . 0.09 and the like) based on 100 parts by weight of the base (I) block copolymer(s).

It should be understood that although the conventional term "parts by weight" is used, the term "parts by weight" is ordinarily used in rubber tire and rubber goods and other formulations. This terms or method of formulation is especially useful and easy to keep track of changes made in formulation work as changes are often needed to arrive at an optimum formulation to improve one property or another. Each of the components which go into a formulation are weight out, except for the "rubber" or base "polymer" which is kept at a constant "100 parts by weight". A simple notation is "hpr" or "hundred parts of rubber" or "pphr" which spells out to read "parts per hundred of rubber".

Any units of weight measure can be use, depending on the available scale used (grams, pounds, oz, etc.). Parts by weight is useful, because not every one on uses the same units of measure. One can convert from "100 parts by weight of rubber" to weight %. For example, "parts by weight of (b)" and "parts by weight of (c)" are based with respect to 100 parts by weight of component "(a)".

A formulation based on parts by weight can be calculated as follows: Add to 100 parts by weight of elastomer "A", 300 parts by weight oil "B", 49 parts by weight resin "C". This formulation has a total weight of "449" which can be in grams, pounds, tons, whatever unit of weight measurement used. In order to convert this formulation into %, we simply divide each of the components by 449" resulting: %A=(100/449)×100=(0.2227271)×100=22.27271%=elastomer, %B=(300/449)×100=(0.6681514)×100=66.81514%=oil, %C=(49/449)×100=10.91314%=resin, and a Total %=99.99999% or 100%

If we performed the measurements in grams, than 100 grams of formulation "ABC" would simply contain 22.27271 grams elastomer, 66.81514 grams of oil, and 10.91314 grams of resin. Consistent with this hundred year old methodology are the terms minor and major with respect to "100 parts by weight of rubber". An amount less than about 50 parts by weight with respect to "100 parts by weight of rubber" would be considered "minor amount." An amount greater than 50 parts by weight with respect to "100 parts by weight of rubber" would be considered "major amount." Gels are inherently sticky or tacky to the touch, especially soft thermoplastic elastomer oil gels which can exhibit extreme tackiness when compounded with high viscosity oils. The tackiness can be reduced, masked or removed by powdering the gel's outside surface or by incorporating additives which will eventually migrate to the gel's outer surface. Such additives being effective only at the gel's surface. The migration of additives from within the bulk gel to the gel's surface is generally due to gradients of pressure or temperature, weak, moderate, or strong molecular dipo/dipo or dipo/non-dipo interactions within the gel. The additives, however, can cause the gels to be translucent or opaque throughout their volume as found in my U.S. Pat. No. 5,760,117 which describes surface activated non-tacky gels. Once the additives are transported from within the gel to the surface forming an "additive layer". Although the additive layer can reduced tackiness or no tack at the gel's surface, the additive layer can themselves impart their own tactical character. For example, stearic acid exhibits a low melting point and tends to be somewhat greasy at ambient or above ambient temperatures. Once the gel is damaged or cut, the tackiness of the freshly cut area is exposed.

Not only can the invention gels be made tacky and adherent to any degree desired or non-tacky to the touch, the gels are naturally transparent, and optically clear suitable for optical use. The gels are strong, elastic, highly tear resistant, and rupture resistant. The invention gels can be formed into any shape for the intended use such as solid shapes for use as articles of manufacture, thin and thick sheets, strands, strings, ropes, fibers, fine silk like filaments can be applied in its molten state onto various substrates as s.

The invention gels of the invention can be formed into gel strands, gel bands, gel tapes, gel sheets, and other articles of manufacture in combination with or without other substrates or materials such as natural or synthetic fibers, multifibers, fabrics, films and the like. Moreover, because of their improved tear resistance and resistance to fatigue, the invention gels exhibit versatility as balloons for medical uses, such as balloon for valvuloplasty of the mitral valve, gastrointestinal balloon dilator, esophageal balloon dilator, dilating balloon catheter use in coronary angiogram and the like. Since the invention gels are more tear resistant, they are especially useful for making condoms, toy balloons, and surgical and examination gloves. As toy balloons, the invention gels are safer because it will not rupture or explode when punctured as would latex balloons which often times cause injures or death to children by choking from pieces of latex rubber. The invention gels are advantageously useful for making gloves, thin gloves for surgery and examination and thicker gloves for vibration damping which prevents damage to blood capillaries in the fingers and hand caused by handling strong shock and vibrating equipment. Various other gel articles can be made from the advantageously tear resistant gels and gel s of the inventions include gel suction sockets, suspension belts.

The invention gels are also useful for forming orthotics and prosthetic articles such as for lower extremity prosthesis described below.

Advantageously, the invention gels of the invention are non-tacky requires no additive. Its non-tackiness are an inherent property of the crystallinity, glassy A components, and selected low viscosity plasticizers forming the invention gels of the invention. Such invention gels, however, must met the following criteria:

(a) the invention gels are made from A-Z-A, (A-Z)$_n$, (A-Y)$_n$, (Y-AY)$_n$ and (Y-AY')$_n$ copolymers: crystalizable block copolymers and crystalizable poly(ethylene-styrene) substantially random copolymers of the type S, M, and E series (for example SEEPS, S-E-EB-S, S-EB45-EP-S, S-E-EB25-S, S-E-EP-E-S, S-EP-E-S, S-EP-E-EP-S, E-S-E, (E-S)$_n$, (E-S-E)$_n$, (ESP), (ES4M1P), (ESH1), (ESO1), (ESN) and (S-E-EP)$_n$, crystalizable S-EB-S with elastomeric crystalizable block:glassy block ratios of 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, and 70:30) and the like;

(b) the invention gels are made from copolymers having crystalizable poly(ethylene) segments exhibit melting exdotherm values and in between of about 10° C., 20° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C. 77° C., 78° C., 79° C., 80° C., and higher; and (c) the invention gels are made from copolymers having glassy A to Y or glassy A to Z ratios of at least 37:63, higher ratios are also of advantage, such as: 38:62, 39:61, 40:60, 41:59, 42:58, 43:57, 44:65, 45:55, 46:54, 47:53, 48:52, 49:51, 50:50, 51:49, 52:48, 53:47, 54:46, 55:45, 56:44, 57:43, 58:42, 59:41, 60:40, 61:39, 62:38, 63:37, 64:36, 65:35, 66:34; or by the addition of (d) sufficient amounts of glassy homopolymers or glass associated phase resins so that condition (c) is met.

It is believed that the combination of sufficient amounts of crystallinity and sufficient amounts glassy A components of the copolymers in combination with low viscosity plasticizers imparts non-tackiness to the invention gels of the invention. It is therefore contemplated that the same effect can be achieved by blending highly crystalizable and highly glassy copolymers (Dow S, M, & E Series E-S-E), with less crystalizable and less glassy copolymers such as amorphous SEPS, SEBS, and amorphous S-EB-EP-S and other amorphous copolymers provided the amorphous copolymers are in minor amounts and there is substantial crystallinity and sufficient over all glassy A components to meet conditions (c).

The glassy homopolymers of (d) are advantageously selected from one or more homopolymers of: polystyrene, poly(alpha-methylstyrene), poly(o-methylstyrene), poly(m-methylstryene), poly(p-methylstyrene), and poly(dimethylphenylene oxide). The average molecular weight of the glassy homopolymers advantageously can range from and in between about 2,500 to about 90,000, typical about 3,000; 4,000; 5,000; 6,000; 7,000; 8,000; 9,000; 10,000; 11,000; 12,000, 13,000; 14,000; 15,000; 16,000; 17,000; 18,000; 19,000; 20,000; 30,000; 40,000; 50,000; 60,000; 70,000; 80,000; 90,000 and the like. Example of various molecular weights of commercially available polystyrene: Aldrich Nos. 32,771-9 (2,500M$_w$), 32,772-7 (4,000 Mw), 37,951-4 (13,000 Mw), 32-774-3 (20,000 Mw) 32,775-1 (35,000 Mw), 33,034-5 (50,000 Mw), 32,777-8 (90,000 Mw); poly (alpha-methylstyrene) #41,794-7 (1,300 Mw), 19,184-1 (4,000 Mw); poly(4methylstyrene) #18,227-3 (72,000 Mw), Endex 155, 160, Kristalex 120, 140 from Hercules Chemical, GE: Blendex HPP820, HPP822, HPP823, and the like. Various glassy phase associating resins having softening points above about 120° C. can also serve to increase the glassy phase of the Invention gels of the invention and met the non-tackiness criteria, these include: Hydrogenated aromatic resins (Regalrez 1126, 1128, 1139, 3102, 5095, and 6108), hydrogenated mixed aromatic resins (Regalite R125), and other aromatic resin (Picco 5130, 5140, 9140, Cumar LX509, Cumar 130, Lx-1035) and the like.

On the other hand, the molten gelatinous elastomer composition will adhere sufficiently to certain, plastics (e.g. acrylic, ethylene copolymers, nylon, polybutylene, polycarbonate, polystyrene, polyester, polyethylene, polypropylene, styrene copolymers, and the like) provided the temperature of the molten gelatinous elastomer composition is sufficient high to fuse or nearly fuse with the plastic. In order to obtain sufficient adhesion to glass, ceramics, or certain metals, sufficient temperature is also required (e.g. above 250° F.). Commercial resins which can aid in adhesion to materials (plastics, glass, and metals) may be added in minor amounts to the gelatinous elastomer composition, these resins include: Super Sta-tac, Nevtac, Piccotac, Escorez, Wingtack, Hercotac, Betaprene, Zonarez, Nirez, Piccolyte, Sylvatac, Foral, Pentalyn, Arkon P, Regalrez, Cumar LX, Picco 6000, Nevchem, Piccotex, Kristalex, Piccolastic, LX-1035, and the like.

The commercial resins which can aid in adhesion to materials (plastics, glass, and metals) may be added in minor amounts to the gelatinous elastomer composition, these resins include: polymerized mixed olefins (Super Sta-tac, Betaprene Nevtac, Escorez, Hercotac, Wingtack, Piccotac), polyterpene (Zonarez, Nirez, Piccolyte, Sylvatac), glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035), and the like. More earlier, I had also disclosed the use of liquid tackifiers in high viscosity SEBS gels.

The incorporation of such adhesion resins is to provide strong and dimensional stable adherent invention gels, gel s, and gel articles. Typically such adherent invention gels can be characterized as adhesive gels, soft adhesives or adhesive sealants. Strong and tear resistant adherent invention gels may be formed with various combinations of substrates or adhere (attach, cling, fasten, hold, stick) to substrates to form adherent invention gel/substrate articles and s.

Various substrate and adherent invention gel combinations which can be utilized to form adherent invention gel articles include: $G_nM_n$, $G_nG_n$, $G_nM_nG_n$, $M_nG_nM_n$, $M_nG_nG_n$, $G_nG_nM_n$, $G_nG_nM_n$, $G_nM_nM_nG_n$, $M_nG_nG_nM_n$, $M_nM_nG_nG_n$, $M_nM_nM_nG_nG_n$, $G_nM_nG_nG_n$, $G_nM_nG_nM_nM_n$, $M_nG_nM_nG_n$-$M_nG_nM_n$, or any permutations of said combination, where G=gel and M=material. The subscript 1, 2, 3, 4, etc., are different and is represented by n which is a positive number, when n is a subscript of M, n may be the same or different material and when n is a subscript of G, n can be the same or different rigidity adherent invention gel or the same or different adherent invention gel material composition. The material (M) suitable for forming articles with the gelatinous elastomer compositions can include foam, plastic, fabric, metal, concrete, wood, wire screen, refractory material, glass, synthetic resin, synthetic fibers, and the like. Sandwiches of adherent invention gel/material (i.e. adherent invention gel-material-adherent invention gel or material-adherent invention gel-material, etc.) are ideal for use as shock absorbers, acoustical isolators, vibration dampers, vibration isolators, and wrappers. For example the vibration isolators can be use under research microscopes, office equipment, tables, and the like to remove background vibrations.

Various useful adhesion resins of one or more types can be incorporated in minor amounts into the adherent invention gel. These include: polymerized mixed olefins, polyterpene, glycerol ester of rosin, pentaerythritol ester of rosin, saturated alicyclic hydrocarbon, coumarone indene, hydrocarbon, mixed olefin, alkylated aromatic hydrocarbon, Polyalphamethylstyrene/vinyl toluene copolymer, polystyrene, special resin, and the like.

The adherent invention gel compositions of the invention can be casted unto various substrates, such as foam, plastic, fabric, metal, concrete, wood, wire screen, refractory material, glass, synthetic resin, synthetic fibers, and the like, or the adherent invention gels formed and then can be adhere (attach, cling, fasten, hold, stick) to the desired substrates to form various $G_nM_n$, $G_nG_n$, $G_nM_nG_n$, $M_nG_nM_n$, $M_nG_nG_n$, $G_nG_nM_n$, $G_nG_nM_n$, $G_nM_nM_nG_n$, $M_nG_nG_nM_n$, $M_nM_nG_nG_n$, $M_nM_nM_nG_nG_n$, $G_nM_nG_nG_n$, $G_nM_nG_nM_nM_n$, $M_nG_nM_nG_n$-$M_nG_nM_n$, or any permutations of said combination s for uses requiring temporary peel and re-use as well as permanent long-life use as needed. Adhesion to substrates is most desirable when it is necessary to apply the adherent invention gels to substrates in the absence of heat or on to a low temperature melting point substrate for later peel off after use, such as for sound damping of a adherent invention gel applied to a first surface and later removed for use on a second surface. The low melting substrate materials which can not be exposed to the high heat of the molten adherent invention gels, such as low melting metals, low melting plastics (polyethylene, PVC, PVE, PVA, and the like) can only be formed by applying the adherent invention gels to the temperature sensitive substrates. Other low melting plastics include: polyolefins such as polyethylene, polyethylene copolymers, ethylene alpha-olefin resin, ultra low density ethylene-octene-1 copolymers, copolymers of ethylene and hexene, polypropylene, and etc. Other cold applied adherent invention gels to teflon type polymers: TEE, PTFE, PEA, FEP, etc., polysiloxane as substrates are achieved using the adherent invention gels of the invention.

Likewise, adherent invention gel substrate s can be both formed by casting hot onto a substrate and then after cooling adhering the opposite side of the adherent invention gel to a substrate having a low melting point. The adherent invention gel is most essential when it is not possible to introduce heat in an heat sensitive or explosive environment or in outer space. The use of solid or liquid resins promotes adherent invention gel adhesion to various substrates both while the adherent invention gel is applied hot or at room temperature or below or even under water. The adherent invention gels can be applied without heating to paper, foam, plastic, fabric, metal, concrete, wood, wire screen, refractory material, glass, synthetic resin, synthetic fibers, and the like.

The adhesion properties of the gels are determined by measuring comparable rolling ball tack distance "D" in cm using a standard diameter "d" in mm stainless steel ball rolling off an inclined of height "H" in cm and determining the average force required to perform 180° peel of a heat formed $G_1M_1$ one inch width sample applied at room temperature to a substrate $M_2$ to form the $M_1G_1M_2$ The peel at a selected standard rate cross-head separation speed of 25 cm/minute at room temperature is initiated at the $G_1M_2$ interface of the $M_1G_1M_2$, where the substrate $M_2$ can be any of the substrates mentioned and $M_1$ preferably a flexible fabric.

Advantageously, glassy phase associating homopolymers such as polystyrene and aromatic resins having low molecular weights of from about 2,500 to about 90,000 can be blended with the triblock copolymers of the invention in large amounts with or without the addition of plasticizer to provide a copolymer-resin alloy of high impact strengths. More advantageously, when blended with multiblock copolymers and substantially random copolymers the impact strengths can be even higher. The impact strength of blends of from about 150 to about 1,500 parts by weight glass phase associating polymer and resins to 100 parts by weight of one or more multiblock copolymers can provide impact strength approaching those of soft metals. At the higher loadings, the impact strength approaches that of polycarbonates of about 12 ft-lb/in notch and higher.

The improvements of the invention gels of the invention is exceptional, the invention gels are invention to the touch and can be quantified using a simple test by taking a freshly cut Invention gel probe of a selected gel rigidity made from the invention gels of the invention. The invention gel probe is a substantially uniform cylindrical shape of length "L" of about 3.0 cm formed components (1)–(3) of the invention gels of the invention in a 16×150 mm test tube. The invention gel probe so formed has a 16 mm diameter hemi-spherical tip which (not unlike the shape of a human finger tip) is brought into perpendicular contact about substantially the center of the top cover of a new, un-touched polystyrene reference surface (for example the top cover surface of a sterile polystyrene petri dish) having a diameter of 100 mm and a weight of 7.6 gram resting on its thin circular edge (which minimizes the vacuum or partial pressure effects of one flat surface in contact with another flat surface) on the flat surface of a scale which scale is tared to zero. The probe's hemi-spherical tip is place in contact with the center of the top of the petri dish cover surface and allowed to remain in contact by the weight of the gel probe while held in the upright position and then lifted up. Observation is made regarding the probe's tackiness with respect to the clean reference polystyrene surface. For purpose of the foregoing reference tack test, tackiness level 0 means the polystyrene dish cover is not lifted from the scale by the probe and the scale shows substantially an equal positive weight and negative weight swings before settling again back to zero with the swing indicated in (negative) grams being less than 1.0 gram. A tackiness level of one 1, means a negative swing of greater than 1.0 gram but less than 2.0 gram, tackiness level 2, means a negative swing of greater than 2 gram but less than 3 gram, tackiness level 3, means a negative swing of greater than 3 gram but less than 4 gram, before settling back to the zero tared position or reading. Likewise, when the negative weight swing of the scale is greater than the weight of the dish (i.e., for the example referred above, greater than 7.6 gram), then the scale should correctly read −7.6 gram which indicates the dish has completely been lifted off the surface of the scale. Such an event would demonstrate the tackiness of a gel probe having sufficient tack on the probe surface. The invention gels of the invention fails to lift off the polystyrene reference from the surface of the scale when subject to the foregoing reference tack test. Advantageously, the invention gels of the invention can register a tackiness level of less than 5, more advantageously, less than 3, still more advantageously, less than 2, and still more advantageously less than 1. The non-tackiness of the invention gels of the invention can advantageously range from less than 6 to less than 0.5 grams, typical tack levels are less than or in between about 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5, 2.8, 3.0, 3.5, 4.0, 4.5, 5.0 grams and the like. Whereas probes of gels made from amorphous gels such as SEPS, SEBS, S-EP-EB-S, and the like with copolymer styrene to rubber ratio of less than 37:63 and plasticizer of higher than 30 cSt 40° C. are found to lift the polystyrene reference from the surface of the scale. For purposes of indicating tack, the method above can provide gel tack level readings of 1, 2, 3, 4, 5, 6, and 7 grams. More accurate and sensitive readings can be made using electronic scales of tack levels of less than 1 gram. By this simple method tack levels (of a gel probe on a polystyrene reference surface) can be measure in terms of gram weight displacement of a scale initially tared to zero. For purpose of the present invention the method of using a polystyrene reference surface having a weight of 7.6 grams in contact and being lifted by the tackiness of a cylindrical gel probe having a 16 mm diameter hemi-spherical tip is used to determine the tackiness of the invention gels of the invention. The level of tack being measured in gram Tack at 23° C.

The improvements of other properties of the invention gels over amorphous gels are many, these include: improved damage tolerance, improved crack propagation resistance, improved tear resistance, improved resistance to fatigue, etc. Such invention gels are advantageous for end-use involving repeated applications of stress and strain resulting from large number of cycles of deformations, including compression, compression-extension (elongation), torsion, torsion-compression, torsion-elongation, tension, tension-compression, tension-torsion, etc. The invention gels also exhibit improved damage tolerance, crack propagation resistance and especially improved resistance to high stress rupture which combination of properties makes the gels advantageously and surprisingly exceptionally more suitable than amorphous gels made from non-crystalline poly(ethylene) component copolymers at corresponding gel rigidities.

Block copolymers with polyethylene midblocks alone do not form suitable Invention gels for purpose of the invention. Crystalizable midblock regions needs to be balanced with amorphous midblock regions in order to obtain soft, flexible and elastic gels with the desired crystalizable properties that are not found in totally amorphous gels.

The various representative glassy domain/amorphous structures of S-E-EB-S, S-E-EB$_{25}$-S, S-E-EP-E-S, S-EP-E-S and S-EP-E-EP-S. Although the structure are spheroid representation, cylinders and plates are also within the scope of the present invention. Cylinder and plate structure are obtained with increasing glassy A end blocks. From about 15–30% by weight of A blocks, the block copolymer structure is spheroid. From about 33 about 40% by weight of A blocks, the block copolymer structure becomes cylindrical; and above about 45% A blocks, the structure becomes less cylindrical and more plate like.

In order to obtain elastic invention gels of the invention, it is necessary that the selective synthesis of butadiene produce sufficient amounts of 1,4 poly(butadiene) that on hydrogenation can exhibit "crystallinity" in the midblocks. In order for the block copolymers forming the invention gels of the invention to exhibit crystallinity, the crystalizable midblock segments must contain long runs of —CH$_2$— groups. There should be approximately 16 units of —(CH$_2$)— in sequence for crystallinity. Only the (—CH$_2$—)$_4$ units can crystallize, and then only if there are 4 units of (—CH$_2$—)$_4$ in sequence; alternatively, the polyethylene units are denoted by [—(CH$_2$—CH$_2$—CH$_2$—CH$_2$)—]$_4$, [(—CH$_2$—)$_4$]$_4$ or (—CH$_2$)16. The amount of (—CH$_2$—)16 units forming the (E) midblocks of the block copolymers comprising the invention gels of the invention should be about 20% which amount is capable of exhibiting a melting endotherm in differential scanning calorimeter (DCS) curves.

Advantageously, the elastomer midblock segment should have a crystallinity of about 20% of (—CH$_2$—)16 units of the total mole % forming the midblocks of the block copolymer, more advantageously about 25%, still more advantageously about 30%, especially advantageously about 40% and especially more advantageously about 50% and higher. Broadly, the crystallinity of the midblocks should range from about 20% to about 60%, less broadly from about 18% to about 65%, and still less broadly from 22% to about 70%.

The melting exdotherm in DSC curves of the crystalizable block copolymers comprising about 20% crystallinity of the polyethylene portion of the midblock are much higher than conventional amorphous block copolymers. The poly(ethylene) crystalizable segments or midblocks of copolymers forming the invention gels of the invention are characterized by sufficient crystallinity as to exhibit a exotherm as determined by DSC curve. The maximum in the endotherm curves of the crystalizable copolymers curs at about 40° C., but can range from greater than about 25° C. to about 60° C. and higher. The crystalizable copolymers forming the invention gels of the invention can exhibit melting endotherms (as shown by DSC) of about 25° C. to about 75° C. and higher. More specific melting exotherm values of the crystalizable block copolymers include: about 8° C., 10° C., 20° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., 80° C., 90° C., 100° C. 110° C., 120° C., and higher whereas, the melting endotherm (DSC) for conventional amorphous midblock segment block copolymers are about 10° C. and lower.

The melting endotherm is seen on heating and a sharp crystallization exotherm is seen on cooling. Such midblock crystallization endothermic and exothermic characteristics are missing from DSC curves of amorphous gels. The crystallization exotherm and fusion endortherm of the crystalizable block copolymer gels of the invention are determined by ASTM D 3417 method.

Generally, the method of obtaining long runs of crystalizable —($CH_2$)— is by sequential block copolymer synthesis followed by hydrogenation. The attaimnent of invention gels of the instant invention is solely due to the selective polymerization of the butadiene monomer (forming the midblocks) resulting in one or more predetermined amount of 1,4 poly(butadiene) blocks followed by sequential polymerization of additional midblocks and hydrogenation to produce one or more crystalizable midblocks of the final block copolymers.

Hydrogenated polyisoprene midblocks remain amorphous, while hydrogenated polybutadiene midblocks can be either amorphous or crystallizable depending upon their structure. Polybutadiene can contain either a 1,2 configuration, which hydrogenates to give the equivalent of a 1-butene repeat unit, or a 1,4-configuration, which hydrogenates to give the equivalent of an ethylene repeat unit. Polybutadiene midblocks having approximately 40 weight percent 1,2-butadiene content, based on the weight of the polybutadiene midblock, provides substantially amorphous blocks with low glass transition temperatures upon hydrogenation. Polybutadiene midblocks having less than approximately 40 weight percent 1,2-butadiene content, based on the weight of the polybutadiene midblock, provide crystalizable midblocks upon hydrogenation. The conjugated diene polymer midblock may also be a copolymer of more than one conjugated diene, such as a copolymer of butadiene and isoprene. Where the midblock of the block copolymer contains more than one conjugated diene polymer block, such as a polybutadiene block and a polyisoprene block, hence hydrogenated midblock can be EB/EP or E/EP depending on the presence and amount of polybutadiene 1,2 and 1,4 microstructure.

The crystalizable block copolymers are made by sequential block copolymer synthesis, the percentage of crystallinity or —($CH_2$)$_{16}$ units should be about $(0.67)_4$ or about 20% and actual crystallinity of about 12%. For example, a selectivity synthesized S-EBn-S copolymer having a ratio of 33:67 of 1,2 and 1,4 poly(butadiene) on hydrogenation will result in a midblock with a crystallinity of $(0.67)_4$ or 20%. For sake of simplicity, when n is a subscript of -EB-, n denotes the percentage of (—$CH_2$—)$_4$ units, eg, n=33 or 20% crystallinity which is the percentage of $(0.67)_4$ or "(—$CH_2$—)$_{16}$" units. Thus, when n=28 or 72% of (—$CH_2$—)$_4$ units, the % crystallinity is $(0.72)_4$ or 26.87% crystallinity attributed to (—$CH_2$—)$_{16}$ units, denoted by -EB$_{28}$-. As a matter of convention, and for purposes of this specification involving hydrogenated polybutadiene: the notation -E- denotes about 85% of (—$CH_2$—)$_4$ units. The notation -B- denotes about 70% of [—$CH_2$—$CH(C_2H_5)$—] units. The notation -EB- denotes between about 15 and 70% [—$CH_2$—$CH(C_2H_5)$—] units. The notation -EBn- denotes n% [—$CH_2$—$CH(C_2H_5)$—] units. For hydrogenated polyisoprene: The notation -EP- denotes about 90% [—$CH_2$—$CH(CH_3)$—$CH_2$—$CH_2$—] units.

Generally, one or more (E) midblocks can be incorporated at various positions along the midblocks of the block copolymers. Using the sequential process for block copolymer synthesis, The (E) midblocks can be positioned as follows:

a) A-E-W-A
b) A-E-W-E-A
c) A-W-E-W-A
d) A-E-W-E-W-E-W-E-A
e) A-W-E-W-A-E-A-E-W-E-A
f) and etc.

The lower flexibility of block copolymer invention gels due to (E) midblocks can be balanced by the addition of sequentially (W) midblocks. For example, the sequentially synthesized block copolymer S-E-EB-S can maintain a high degree of flexibility due to the presence of amorphous -EB- block. The sequential block copolymer S-E-EB-B-S can maintain a high degree of flexibility due to the presence of amorphous -EB- and -B- midblocks. The sequential block copolymer S-E-EP-E-S can maintain a high degree of flexibility due to the presence of -EP- midblock. The sequential block copolymer S-E-B-S can maintain a high degree of flexibility due to the presence of the -B- midblock. For S-E-S, where the midblock is crystalizable and flexibility low, physical blending with amorphous block copolymers such as S-EB-S, S-B-S, S-EP-S, S-EB-EP-S$_n$, (S-EP), and the like can produce more softer, less rigid, and more flexible invention gel.

Because of the (E) midblocks, the invention gels of the invention exhibit different physical characteristics and improvements over substantially amorphous gels including damage tolerance, improved crack propagation resistance, improved tear resistance producing knotty tears as opposed to smooth tears, crystalizable melting point of 28° C., improved resistance to fatigue, higher hysteresis, etc. Moreover, the invention gels when stretched exhibit additional yielding as shown by necking caused by stress induced crystallinity. Additionally, the crystallization rates of the crystalizable midblocks can be controlled and slowed depending on thermal history producing time delay recovery upon deformation.

Regarding resistance to fatigue, fatigue (as used herein) is the decay of mechanical properties after repeated application of stress and strain. Fatigue tests give information about the ability of a material to resist the development of cracks or crazes resulting from a large number of deformation cycles. Fatigue test can be conducted by subjecting samples of amorphous and invention gels to deformation cycles to failure (appearance of cracks, crazes, rips or tears in the gels).

Tensile strength can be determined by extending a selected gel sample to break as measured at 180° U bend around a 5.0 mm mandrel attached to a spring scale. Likewise, tear strength of a notched sample can be determined by propagating a tear as measured at 180° U bend around a 5.0 mm diameter mandrel attached to a spring scale.

Various block copolymers can be obtained which are amorphous, highly rubbery, and exhibiting minimum dynamic hysteresis:

Block Copolymer S-EB-S

The monomer butadiene can be polymerized in a ether/hydrocarbon solvent to give a 50/50 ratio of 1,2 poly(butadiene)/1,4 poly(butadiene) and on hydrogenation no long runs of —CH2— groups and negligible crystallinity, ie, about $(0.5)^4$ or 0.06 or 6% and actual crystallinity of about 3%. Due to the constraints of Tg and minimum hysteresis, conventional S-EB-S have ethylene-butylene ratios of about 60:40 with a crystallinity of about $(0.6)^4$ or 0.129 or 12% and actual crystallinity of about 7.7%.

Block Copolymer S-EP-S

The monomer isoprene when polymerized will produce 95% 1,4 poly(isoprene)/5% 3,4 poly(isoprene) and upon hydrogenation will form amorphous, rubbery poly(ethylene-propylene) midblock and no long runs of —$CH_2$— and no crystallinity.

Mixed Block Copolymer S-EB/EP-S

The polymerization of a 50/50 mixture of isoprene/butadiene monomers in suitable ether/hydrocarbon solvents to give equal amounts of 1,2 and 1,4 poly(butadiene) on hydrogenation will produce a maximum crystallinity of $(0.25)^4$ or 0.4%. The actual crystallinity would be approximately about 0.2%, which is negligible and results in a good rubbery midblock.

The polymerization of a 80/20 mixture of isoprene/butadiene monomers in suitable ether/hydrocarbon solvents to give equal amounts of 1,2 and 1,4 poly(butadiene) will upon hydrogenation produce a low crystallinity of $(0.10)^4$ or 0.01% The actual crystallinity would be approximately about 0.006%, which is negligible and results in a good rubbery midblock.

The polymerization of a 20/80 mixture of isoprene/butadiene monomers in suitable ether/hydrocarbon solvents to give equal amounts of 1,2 and 1,4 poly(butadiene) will upon hydrogenation produce a low crystallinity of $(0.4)^4$ or 2.56%. The actual crystallinity would be approximately about 1.53%, which is negligible and results in a good rubbery midblock.

The polymerization of a 20/80 mixture of isoprene/butadiene monomers in suitable ether/hydrocarbon solvents to give a 40:60 ratio of 1,2 and 1,4 poly(butadiene) will upon hydrogenation produce a low crystallinity of $(0.48)_4$ or 5.3% The actual crystallinity would be approximately about 3.2%, which is negligible and results in a good rubbery midblock.

For purpose of convince and simplicity, the hydrogenated polybutadiene are denoted as follows: -E- denotes 85% R-1 units, -B- denotes 70% R-2 units, -EB- denotes between 15 and 70% R-2 units, -EBn- denotes n% R-2 units, and -EP- denotes 90% R-3 units.

| n=   | R-1  | R-2 | R-3 | R-4 |
|------|------|-----|-----|-----|
| 0%   | 0%   | 0%  | 95% | 5%  |
| 20%  | 18%  | 2%  | 76% | 4%  |
| 40%  | 36%  | 4%  | 57% | 3%  |
| 60%  | 54%  | 6%  | 38% | 2%  |
| 80%  | 72%  | 8%  | 19% | 1%  |
| 100% | 90%  | 10% | 0%  | 0%  |

Therefore, the percentage that can crystallize is $[(-CH_2-)_4]_4$ since this is the chance of getting four $(-CH_2-)_4$ units in sequence. The percentage that will crystallize is about 60% of this.

| n=   | $(-CH_2-)_4$ | $[(-CH_2-)_4]_4$ | $0.6 \times [(-CH_2-)_4]_n$ |
|------|--------------|------------------|----------------------------|
| 0%   | 0%           | 0%               | 0%                         |
| 20%  | 18%          | 0.1%             | 0.06%                      |
| 40%  | 36%          | 1.7%             | 1.0%                       |
| 60%  | 54%          | 8.5%             | 5.1%                       |
| 80%  | 72%          | 26.9%            | 16.1%                      |
| 100% | 90%          | 65.6%            | 39.4%                      |

This applies to polymerization in a hydrocarbon solvent. In an ether (eg, diethylether), the percentage $(-CH_2-)_4$ units will be reduced so that crystallinity will be negligible.

| n=   | $(-CH_2-)_4$ | $[(-CH_2-)_4]_4$ | $0.6 \times [(-CH-)_4]_n$ |
|------|--------------|------------------|---------------------------|
| 0%   | 0%           | 0%               | 0%                        |
| 20%  | 5%           | 0.0006%          | 0.0004%                   |
| 40%  | 10%          | 0.01%            | 0.006%                    |
| 60%  | 15%          | 0.05%            | 0.03%                     |
| 80%  | 20%          | 0.16%            | 0.10%                     |
| 100% | 25%          | 0.39%            | 0.23%                     |

These values are all negligible. There will be no detectable crystallinity in any of these polymer midblocks. In a mixed ether/hydrocarbon solvent, values will be intermediate, depending on the ratio of ether to hydrocarbon.

The midblocks (Z) of one or more -E-, -B-, -EB-, or -EP- can comprise various combinations of midblocks between the selected end blocks (A); these include: -E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-E-EB-, -E-EP-E,EP-EB-, -E-EP-E-EP-E-, -E-EP-EB-EP-EB-B- and the like.

The (i) and (v) block copolymers of (A-Z-A) can be obtained by sequential or random synthesis methods followed by hydrogenation of the midblocks. As denoted above, abbreviations are interchangeably used, for example, (S-E-EP-S) denotes poly(styrene-ethylene-ethylene-co-propylene-styrene). Other linear block copolymers (denoted in abbreviations) include the following: (S-E-EB-S), (S-E-EP-S), (S-B-EP-S), (S-B-EB-S), (S-E-EP-E-S), (S-E-EB-B-S), (S-B-EP-B-S), (S-B-EB-B-S), (S-E-B-EB-S), (S-E-B-EP-S), (S-EB-EP-S), (S-E-EB-EP-S), (S-E-EP-EB-S), (S-B-EB-EP-S), (S-B-EP-EB-S), (S-E-EP-E-EP-S), (S-E-EP-E-EB-S), (S-EP-B-EP-S), (S-B-EB-B-EB-S), (S-B-EB-B-EP-S), (S-E-EP-B-EP-S), (S-B-EP-B-EP-S), (S-E-EP-E-EB-S), (S-E-EP-EB-S), (S-B-EP-B-EP-B-S), (S-E-EP-E-EB-S), (S-E-EP-EB-S), (S-E-EP-E-EP-E-S), (S-E-EP-EB-EP-EB-B-S), (S-E-EP-EB-EP-EB . . . -S) and the like.

The (ii) and (iv) multiblock star-shaped (or radial) copolymers $(A-Z)_nX$ can be obtained by sequential synthesis methods including hydrogenation of selected block copolymers made by polymerizing half of the block copolymers such as SBS or SIS and couple the halves with a coupling agent such as an organic dihalide; or couple with an agent such as $SnCl_4$, which results in star-shaped block copolymers (four branches). Coupling with divinyl benzene give block copolymers which are very highly branched. Radial block copolymers suitable for use in forming the invention gels of the present invention include: $(S-E-EB-S)_n$, $(S-E-EP)_n$, $(S-B-EP)_n$, $(S-B-EB)_n$, $(S-E-EP-E)_n$, $(S-E-EB-B)_n$, $(S-B-EP-B)_n$, $(S-B-EB-B)_n$, $(S-E-B-EB)_n$, $(S-E-B-EP)_n$, $(S-EB-EP)_n$, $(S-E-EB-EP)_n$, $(S-E-EP-EP)_n$, $(S-B-EB-EP)_n$, $(S-B-EP-EB)_n$, $(S-E-EP-E-EP)_n$, $(S-E-EP-E-EB)_n$, $(S-EP-B-EP)_n$, $(S-B-EB-B-EB)_n$, $(S-B-EB-B-EP)_n$, $(S-E-EB-B-EP)_n$, $(S-E-EP-B-EB)_n$, $(S-E-EP-E-EP-E)_n$, $(S-B-EP-B-EP-B)_n$, $(S-E-EP-E-EB)_n$, $(S-E-EP-E-EP-EB)_n$, $(S-E-EP-E-EP-E)_n$, $(S-E-EP-EB-EP-EB-B)_n$ The selected amount of crystallinity in the midblock should be sufficient to achieve improvements in one or more physical properties including improved damage tolerance, improved crack propagation resistance, improved tear resistance, improved resistance to fatigue of the bulk gel and resistance to catastrophic fatigue failure of invention gel s, such as between the surfaces of the invention gel and substrate or at the interfaces of the interlocking material(s) and invention gel, which improvements are not found in amorphous gels at corresponding gel rigidities.

As an example, when fabric interlocked or saturated with amorphous S-EB-S gels (gel s) are used as gel liners for lower limb or above the knee prosthesis to reduce pain over pressure areas and give relief to the amputee, the commonly used amorphous gels forming the liners can tear or rip apart during marathon racewalk after 50–70 miles. In extended use, the amorphous gels can rip on the bottom of the liner in normal racewalk training of 40–60 miles over a six weeks period. In such demanding applications, the invention gels are especially advantageous and is found to have greater tear resistance and resistance to fatigue resulting from a large number of deformation cycles than amorphous gels. The invention gels are also useful for forming various orthotics and prosthetic articles such as for lower extremity prosthesis of the L5664 (lower extremity socket insert, above knee), L5665 (socket insert, multi-durometer, below knee), L5666 (below knee, cuff suspension interface), L5667 (below knee, above knee, socket insert, suction suspension with locking mechanism) type devices as described by the American Orthotic & Prosthetic Association (AOPA) codes. The invention gels are useful for making AOPA code devices for upper extremity prosthetics. The devices can be cast molded or injection molded in combination with or without fiber or fabric backing or fiber or fabric reinforcement. When such liners are made without fabric backing, various gels can be used to form gel-gel and gel-gel-gel s and the like with varying gel rigidities for the different gel layer(s). Such liners can be made from high viscosity SEBS (such as Kraton 1651 and Septon 8006) and moderate viscosity SEBS (Kraton 1654 and Septon 8007) block copolymers gels. The add advantage of liners made from SEEPS gels is that such gels exhibit tear and fatigue resistance not achievable using SEBS and SEPS alone.

Silipos product catalogue (referenced above) which shows a Single Sock Gel Liner product #1272, This and other same but different sized products (#1275 and #1276) were on Public sale. Products #1272 was offered for public sale and sold to the public on or about Jan. 31, 1995, #1275 was on public sale on or about Jan. 31, 1995 and #1276 was on public sale on or about Dec. 31, 1994. The Single Sock Gel Liner is a tube sock-shaped covering for enclosing an amputation stump with a open end for introduction of the stump and a closed end opposite the open end. The liner is a fabric in the shape of a tube sock coated on only one side with a gel made from a block copolymer and oil. The gel liners products #1272, #1275, and #1276 were on public sale as of the above mentioned dates which products were coated with a block copolymer gel described in U.S. Pat. Nos: 4,369,284 and 4,618,213.

Selected linear block and radial copolymers utilized in forming the invention gels of the invention are characterized as having an ethylene to butylene midblock ratio (E:B) of about 85:15 to about 65:35. Advantageously, the butylene concentration of the midblock is about 35% or less, more advantageously, about 30% or less, still more advantageously, about 25% or less, especially advantageously, about 20% or less. Advantageously, the ethylene to britylene midblock ratios can range from and in between about 89:11, 88:12, 87:13, 86:14, 85:15, 84:16, 83:17, 82:18, 81:19, 80:20, 79:21, 78:22, 77:23, 76:24, 75:25, 74:26, 73:27, 72:28, 71:29, 70:30, 69:31, 68:32, 67:33, 66:34 to about 65:35.

The A to Z midblock ratio of the block copolymers suitable for forming invention gels of the invention can range from about 20:80 to 40:60 and higher. More specifically, the values can be and in between: 15:85, 19:81, 20:80, 21:79, 22:78, 23:77, 24:76, 25:75, 26:74, 27:73, 28:72, 29:71, 30:70, 31:69, 32:68, 33:67, 34:66, 35:65, 36:64, 37:63, 38:62, 39:61, 40:60, 41:59, 42:58, 43:57, 44:65, 45:55, 46:54, 47:53, 48:52, 49:51, 50:50, 51:49, 52:48, 53:47, 54:46, 55:45, 56:44, 57:43, 58:42, 59:41, 60:40, 61:39, 62:38, 63:37, 64:36, 65:35, 66:34, 6:33, 68:32, 69:31, 70:30 and higher.

The invention gels can be made in combination with or without a selected amount of one or more selected polymers and copolymers in amounts without substantially decreasing the desired properties. Such polymers includes: thermoplastic crystalizable polyurethane elastomers with hydrocarbon blocks, homopolymers, copolymers, block copolymers, polyethylene, polypropylene, polystyrene, polyethylene copolymers, polypropylene copolymers, and the like. Other (vii) polymers and copolymers can be linear, star-shaped (radial), branched, or multiarm; these including: (SBS) styrene-butadiene-styrene block copolymers, (SIS) styrene-isoprene-styrene block copolymers, low and medium viscosity (S-EB-S) styrene-ethylene-butylene-styrene block copolymers, (S-EP) styrene-ethylene-propylene block copolymers, (S-EP-S) styrene-ethylene/propylene-styrene block copolymers, (S-E-EPS) styrene-ethylene-ethylene/propylene-styrene block copolymers, $(SB)_n$ styrene-butadiene and $(S-EB)_n$, $(S-EB-S)_n$, $(S-E-EP)_n$, $(SEP)_n$, $(SI)_n$ multi-arm, branched or star-shaped copolymers, polyethyleneoxide (EO), poly(dimethylphenylene oxide), teflon (TFE, PTFE, PEA, FEP, etc), optical clear amorphous copolymers based on 2,2-bisfluoromethyl-4,5-difluoro-1,3-dioxole (PDD) and tetrafluoroethylene (TFE), maleated S-EB-S block copolymer, polycarbonate, ethylene vinyl alcohol copolymer, ethylene/styrene interpolymers, and the like. Still, other polymers include homopolymers which can be utilized in minor amounts; these include: polystyrene, polydimethylsiloxane, polyolefins such as polybutylene, polyethylene, Hoechst Celanese/PEG 20000 UHMW polyethylene (Mw=1,000,000–6,000,000), polyethylene copolymers, polypropylene, silicone (Trospearl 120A, 145A etc) and the like. Polyurethane thermoplastic crystalizable copolymers with hydrocarbon midblocks based on saturated hydrocarbon diols (Handlin, D., Chin. S., and Masse. M., et al. "POLYURETHANE ELASTOMERS BASED ON NEW SATURATED HYDROCARBON DIOLS" Published Society of Plastics Industry, Polyurethane Division, Las Vegas, Oct. 23, 1996) are also suitable for use in blending with the block copolymers (i–vi) used in forming the invention gels of the invention. Such saturated hydrocarbon diols include hydroxyl terminated oligomers of poly(ethylene-butylene) (EB), poly(ethylene-propylene) (EP), -E-EB-, -E-EP-, -B-EP-, -B-EB-, -E-EP-E-, -E-EB-B-, -B-EP-B-, -B-EB-B-, -E-B-EB-, -E-B-EP-, -EB-EP-, -E-EB-EP-, -E-EP-EB-, -B-EB-EP-, -B-EP-EB-, -E-EP-E-EP-, -E-EP-E-EB-, -B-EP-B-EP-, -B-EB-B-EB-, -B-EB-B-EP-, -E-EB-B-EP-, -E-EP-B-EB-, -E-EP-E-EP-E-, -B-EP-B-EP-B-, -E-EP-EB-, -E-EP-E-EP-EB-, -E-EP-E-EP-E-, -E-EP-EB-EP-EB-B- and the like. As an example, thermoplastic polyurethane made with isocyanates and chain extenders such as TMPD and BEPD from saturated hydrocarbon diol KLP L-2203 having a hard segment contents of 22% exhibits clean phase separation of the hard and soft segments with glass a transition of −50° C. KLP L-2203 based TPU's can be mixed with the crystalizable block copolymers to form soft invention gels within the gel rigidity ranges of the invention.

As described in U.S. patent application Ser. No. 20020061982 and incorporated herein by reference, ethylene/styrene interpolymers are prepared by polymerizing i) ethylene or one or more alpha-olefin monomers and ii) one or more vinyl or vinylidene aromatic monomers and/or one or more sterically hindered aliphatic or cycloaliphatic vinyl or vinylidene monomers, and optionally iii) other polymerizable ethylenically unsaturated monomer(s).

Ethylene/styrene interpolymers can be substantially random, pseudo-random, random, alternately, diadic, triadic, tetradic or any combination thereof. That is, the interpolymer product can be variably incorporated and optionally variably sequenced. Preferred ethylene/styrene interpolymers are substantially random ethylene/styrene interpolymers.

The high glassy component (viii) copolymers suitable for use in forming the invention gels of the invention include high styrene component BASF's Styroflex series copolymers including BX 6105 with a statistical SB sequence for the low elastomeric segments (styrene to butadiene ratio of 1:1) and an overall styrene content of almost 70%, high styrene content Shell Kraton G, Kraton D-1122X $(SB)_n$, D-4122 SBS, D4240 $(SB)_n$, D4230 $(SB)_n$, DX-1150 SBS, D-4140 SBS, D-1115 SBS, D-4222 SBS, Kraton D-1401P, SEBS, Dexco's Vector 6241-D, 4411-D, Fina's Finaclear high styrene content SBS series copolymers, Phillips Petroleum's XK40 K-Resin styrene/butadiene copolymers, Kuraray's S2104 SEPS. The (viii) copolymers include amorphous polymers with high styrene content: SBS, SIS, SEPS, SEB/EPS, and the like. The (i–viii) copolymers with glassy to elastomeric ratios can range from and in between 37:63, 37.6:62.4, 38:62, 39:61, 40:60, 41:59, 42:58, 43:57, 44:65, 45:55, 46:54, 47:53, 48:52, 49:51, 50:50, 51:49 52:48, 53:47, 54:46, 55:45, 56:44, 57:43, 58:42, 59:41, 60:40, 6:39, 62:38, 63:37, 64:36, 65:35, 66:34, 67:33, 68:32, 69:31, 70:30, 7:29, 72:28, 73:27, 74:26, 75:25, 76:24, 77:23, 78:22, 79:21, to 80:20 and higher.

Suitable polyolefins include polyethylene and polyethylene copolymers such as Dow Chemical Company's Dowlex 3010, 2021D, 2038, 2042A, 2049, 2049A, 2071, 2077, 2244A, 2267A; Dow Affinity ethylene alpha-olefin resin PL-1840, SE-1400, SM-1300; more suitably: Dow Elite 5100, 5110, 5200, 5400, Primacor 141-XT, 1430, 1420, 1320, 3330, 3150, 2912, 3340, 3460; Dow Attane (ultra low density ethylene-octene-1 copolymers) 4803, 4801, 4602, Eastman Mxsten CV copolymers of ethylene and hexene (0.905–0.910 g/cm3).

The conventional term "major" means about 51 weight percent and higher (e.g. 55%, 60%, 65%, 70%, 75%, 80% and the like) and the term "minor" means 49 weight percent and lower (e.g. 2%, 5%, 10%, 15%, 20%, 25% and the like).

Representative plasticizer oil gels (polymer+oil) of the invention include: (a) Kraton G 1651, G 1654X gels; (b) Kraton G 4600 gels; (c) Kraton G 4609 gels; other suitable high viscosity polymer and oil gels include: (d) Tuftec H 1051 gels; (e) Tuftec H 1041 gels; (f) Tuftec H 1052 gels; (g) Kuraray SEEPS 4055 gel; (h) Kuraray SEBS 8006 gel; (i) Kuraray SEPS 2005 gel; (j) Kuraray SEPS 2006 gel, and (k) Gels made from blends (polyblends) of (a)–(h) with other polymers and copolymers include: (1) SEBS-SBS gels; (2) SEBS-SIS gels; (3) SEBS-(SEP) gels; (4) SEBS-$(SEB)_n$ gels; (5) SEBS-$(SEB)_n$ gels; (6) SEBS-$(SEP)_n$ gels; (7) SEBS-$(SI)_n$ gels; (8) SEBS-(SI) multiarm gels; (9) SEBS-$(SEB)_n$ gels; (10) $(SEB)_n$ star-shaped copolymer gels; (11) gels made from blends of (a)–(k) with other homopolymers include: (12) SEBS/polystyrene gels; (13) SEBS/polybutylene gels; (14) SEBS/polyethylene gels; (14) SEBS/polypropylene gels; (16) SEP/SEBS oil gels (17), SEP/SEPS oil gels (18), SEP/SEPS/SEB oil gels (19), SEPS/SEBS/SEP oil gels (20), SEB/SEBS (21), EB-EP/SEBS (22), SEBS/EB (23), SEBS/EP (24), (25) $(SEB)_n$ gels, (26) $(SEP)_n$ gels, (27) SEEPS gels, and the like.

Representative examples of commercial elastomers that can be formed with plasticizing oils in combination with the high viscosity triblock and branched copolymers described above into suitable gels for use in making the gel compositions and articles of the invention: Shell Kratons D1101, D1102, D1107, D1111, D1112, D1113X, D1114X, D1116, D1117, D1118X, D1122X, D1125X, D1133X, D1135X, D1184, D1188X, D1300X, D1320X, D4122, D4141, D4158 D4240, G1650, G1652, G1657, G1701X, G1702X, G1726X, G1750X, G1765X, FG1901X, FG1921X, D2103, D2109, D2122X, D3202, D3204, D3226, D5298, D5999X, D7340, G1654X, G2701, G2703, G2705, G1706, G2721X, G7155, G7430, G7450, G7523X, G7528X, G7680, G7705, G7702X, G7720, G7722X, G7820, G7821X, G7827, G7890X, G7940, Kuraray's SEEPS, SEP/SEPS or SEP/SEB/SEPS Nos. 1001, 1050, 2002, 2003, 3023, 2007, 2043, 2063, 2050, 2103, 2104 (SEPS with a high styrene content of 65), 2105, 4033 (SEEPS), 4044 (SEEPS), 4045 (SEEPS), 4077 (SEEPS), 4099 (SEEPS), 8004 (SEBS), 8007, H-VS-3 (S-V-EP)n, Dexco polymers (Vector): 4411, 4461, 6241, DPX555, tuftec-P series SBBS (styrene-butadiene-butylene-styrene) and the like.

The Kuraray SEPTON 4000 (SEEPS) series block polymers: 4033, 4044, 4055, 4045,4077, 4099, and the like useful in making the gels of the instant invention are made from hydrogenated styrene isoprene/butadiene styrene block copolymer or more specifically made from hydrogenated styrene block polymer with 2-methyl-1,3-butadiene and 1,3-butadiene. Such poly(styrene-isoprene/butadiene-styrene) polymers, depending on the butadiene structure, when hydrogenated will result in "(SEB/EPS)". In cases where the butadiene structures are controlled, it is appropriate to denote (SEB/EPS) as (SE/EPS) where E/EP is ethylene-ethylene-propylene or more simply as (SEEPS) to indicate that the ethylene (E) of the ethylene-butylene (EB) segment of the midblock (EB/EP) of the (SEB/EPS) block polymer is substantially greater than butylene (B) and the amount of (E) can be sufficient so as to exhibit ethylene crystallinity. As indicated below, it is the presence or absence of the butylene methyl group which can be use to distinguish the SEBS polymer from the SEPS and SEEPS types of polymer. The SEEPS polymer of the invention gel, within the experimental uncertainty, lacks sufficient butylene. The invention gels can comprise (I) SEEPS polymers and other (II) polymers, such as: SEPS, SEBS, SIS, SBS, SEB/EPS and the like.

As taught in my co-pending U.S. application Ser. Nos. 10/273828 and 10/1999364, and specifically incorporated herein, the unusual properties of the invention SEEPS gels can be attributed to altering different phase or interfacial arrangements of the domains of the multiblock copolymers. The presence of polyethylene and crystallinity in block copolymers can be determined by NMR and DSC.

Physical measurements (NMR and DSC) of typical commercial Kraton G 1651, Septon 2006, Septon 4033 and Septon 4055 block were performed. Two types of $^{13}C$ NMR spectra data were collected. The gated decoupled experiment provided quantitative data for each type of carbon atom. The DEPT experiment identified each type of carbon atom having attached protons. The DEPT data allowed assignment of the resonances in the gated decoupled experiment, which was then integrated for quantitation of the different types of midblock and end groups in each polymer tested.

The relative quantities of each type of carbon group in the various polymers were found. The uncertainty associated with these measurements is estimated as ±3 percentage units. Only the Kraton 1651 spectrum had resonances below about 20 ppm. These resonances, at 10.7–10.9 ppm, were assigned to the butylene methyl group and distinguish the SEBS polymer from the SEPS and SEEPS types of polymer (36). Only the Septon 2006 spectrum lacked the resonance at about 20 ppm that is characteristic of polyethylene units (defined here as three contiguous $CH_2$ groups), and this feature distinguishes the SEPS polymer from the SEBS and SEEPS polymers (49). There were additional differences between the spectra. The Septon 2006 and the Septon 4033 and 4055 spectra all showed resonances at 20 ppm; whereas the spectrum of Kraton 1651 was missing this resonance. The 20 ppm peak is characteristic of the methyl group of a propylene subunit, which is present in SEPS and SEEPS polymers but absent in the SEBS polymer. There were also a methylene peak, at 24.6 ppm, and a methine peak at 32.8 ppm, in all of the Septon spectra but not in the Kraton 1651 spectra. These resonances also arise from the propylene subunit.

The chemical shifts, relative intensities, and relative integrations were the same for the spectra of the Septon 4033 and Septon 4055, indicating that these two polymeric compositions are identical based on NMR spectroscopy.

DSC of ASTM D3417-99 was modified to provide conditions for the samples to have the best possible chance to exhibit any crystallinity. The protocol was as follows: (1) heat to 140° C. @ 10° C./min., (2) cool to 0° C. @ 2° C./min., (3) place in freezer for 1 week, (4) heat to 140° C. @ 1° C./min, and (5) cool to 0° C. @ 1° C./min.

This protocol was used with the exception that the samples were left in the freezer for approximately 2 months, instead of 1 week, because the DSC equipment broke during the week after the first run and required some time for repair. This delay is not expected to have negatively impacted the results of the experiment.

Two HDPE reference samples gave clearly defined crystallization exotherms and fusion endotherms, allowing calculation of heats of crystallization and fusion. These results showed that the equipment and methodology were fully functional, and this check was performed daily during DSC operation. Of the samples, only Kraton 1651 showed discernable transitions for both crystallization and fusion. The Septon 2006 showed no discernable transitions, which is consistent with its SEPS structure being entirely amorphous. The Septons 4033 and 4055 showed crystallization exotherms.

The heats of crystallization for the Kraton 1651 and Septons 4033 and 4055 were small, below about 3 J/g, indicating that small amounts of crystallinity are present in these polymers. The DSC data show:

Kraton 1651: crystallization exotherm peak at 18.09° C., crystallization exotherm—mass normalized enthalphy (J/g) of 1.43, fusion endotherm peak at 34.13° C., and Fusion Endotherm—mass normalized enthalphy J/g of 15.17.

Septon 2006: crystallization exotherm peak (not detected), crystallization exotherm—mass normalized enthalphy (not detected), fusion endotherm peak NONE, and Fusion Endotherm—mass normalized enthalphy (not detected).

Septon 4033: crystallization exotherm peak at 2.86° C., crystallization exotherm—mass normalized enthalphy (J/g) of 3.00, fusion endotherm peak (not detected), and Fusion Endotherm—mass normalized enthalphy (not detected).

Septon 4055: crystallization exotherm peak at 14.4° C., crystallization exotherm—mass normalized enthalphy (J/g) of 1.32, fusion endotherm peak (not detected), and Fusion Endotherm—mass normalized enthalphy (not detected).

Aldrich 13813JU polyethylene reference: crystallization exotherm peak at 119.72° C., crystallization exotherm—mass normalized enthalphy (J/g) of 174.60, fusion endotherm peak at 130.70° C., and Fusion Endotherm—mass normalized enthalphy J/g of 189.90.

The invention gels made from higher viscosity SEEPS copolymers (I) are resistant to breaking when sheared than SEPS triblock copolymer gels. This can be demonstrated by forming a very soft gel, for example 100 parts copolymer to 800 parts plasticizing oil. The soft gel is cut into a strip of 2.5 cm×2.5 cm cross-section, the gel strip is gripped lengthwise tightly in the left hand about its cross-section and an exposed part of the gel strip being gripped lengthwise around its cross-section tightly by the right hand as close to the left hand as possible without stretching. With the two hands gripping the gel strip's cross-section, the hands are moved in opposite directions to shear apart the gel strip at its cross-section. The shearing action by the gripping hands is done at the fastest speed possible as can be performed by human hands. The shearing action is performed at a fraction of a second, possible at about 0.5 seconds. Using this demonstration, the SEEPS copolymer (1) invention gels will not easily break completely apart as would gels formed from SEPS triblock copolymers. In some cases, it will take two, three, or more attempts to shear a high viscosity copolymer (I) gel strip this way. Whereas, a lower viscosity triblock copolymer gel strip can be sheared apart on the first try. For gels made from copolymers with viscosities of 5 wt % solution in Toluene of from less than 2 mPa-S to 500 mPa-S and higher, their shear resistance will decrease with decreasing viscosity.

Hence, it is the selected SEEPS which provides the improved tear and fatigue resistance of the invention gel compositions and articles. SEEPS gels of corresponding rigidity exhibit improved greater tear and greater fatigue resistance over SEPS gels and SEBS gels.

As taught in my co-pending U.S. application: Ser. Nos. 09/721213; 09/130,545; 10/273828; 09/517230; 09/412886; 10/1999364 and specifically incorporated herein, tear strength and resistance to fatigue of the high viscosity SEEPS gels of the invention at corresponding rigidities are found to be greater than that of SEPS gels. Greater tear and fatigue resistance is also found when SEEPS gels are made in combination with other (II) polymers, such as SEPS, SEBS, SBS, SIS, low viscosity SEBS, lower viscosity SEEPS, PS, PE, PP, $(SI)_n$, $(SB)_n$, $(SEB)_n$, Ashai SB/EBS poly(styrene-butadiene-ethylene-butylene-styrene), and the like.

The amorphous S-EB-S and $(S-EB)_n$ copolymers can have a broad range of styrene to ethylene-butylene ratios (S:EB) of about 20:80 or less to about 40:60 or higher. The S:EB weight ratios can range from lower than about 20:80 to above about 40:60 and higher. More specifically, the values can be from and in between: 15:85, 19:81, 20:80, 21:79, 22:78. 23:77, 24:76, 25:75, 26:74, 27:73, 28:72, 29:71, 30:70, 31:69, 32:68, 33:67, 34:66, 35:65, 36:64, (and higher ratios for viii copolymers) 37:63, 37.6:62.4, 38:62, 39:61, 40:60, 41:59, 42:58, 43:57, 44:65, 45:55, 46:54, 47:53, 48:52, 49:51, 50:50, 51:49 52:48 and etc. Other ratio values of less than 19:81 or higher than 51:49 are also possible. Broadly, the styrene block to elastomeric block ratio of the high viscosity liner and star copolymers is about 20:80 to about 40:60 or higher, less broadly about 31:69 to about 40:60, preferably about 32:68 to about 38:62, more preferably about 32:68 to about 36:64, particularly more preferably about 32:68 to about 34:66, especially more preferably about 33:67 to about 36:64, and still more preferably about 30:70.

The Brookfield Viscosity of a 5 weight percent solids solution in toluene at 30° C. of 2006, 4033, 4045, 4055, and 4077 typically range about 20–35, about 25–150, about 60–150, about 200–400 respectively. Typical Brookfield Viscosities of a 10 weight percent solids solution in toluene at 30° C. of 1001, 1050, 2007, 2063, 2043, 4033, 2005, 2006, are about 70, 70, 17, 29, 32, 50, 1200, and 1220 respectively. Typical Brookfield Viscosity of a 25 weight percent solids solution in toluene at 25° C. of Kraton D1101, D1116, D1184, D1300X, G1701X, G1702X are about 4000, 9000, 20000, 6000, 50000 and 50000 cps respectively. Typical Brookfield Viscosity of a 10 weight percent solids solution in toluene at 25° C. of G1654X is about 370 cps. The Brookfield Viscosities of a 20 and 30 weight percent solids solution in toluene at 30° C. of H-VS-3 are about 133 cps and 350 cps respectively.

Suitable block copolymers and their typical viscosities are further described. Shell Technical Bulletin SC: 1393-92 gives solution viscosity as measured with a Brookfield model RVT viscometer at 25° C. for Kraton G 1654X at 10% weight in toluene of approximately 400 cps and at 15% weight in toluene of approximately 5,600 cps. Shell publication SC:68–79 gives solution viscosity at 25° C. for Kraton G 1651 at 20 weight percent in toluene of approximately 2,000 cps. When measured at 5 weight percent solution in toluene at 30° C., the solution viscosity of Kraton G 1651 is about 40. Examples of high viscosity S-EB-S triblock copolymers includes Kuraray's S-EB-S 8006 which exhibits a solution viscosity at 5 weight percent at 30° C. of about 51 cps. Kuraray's 2006 SEPS polymer exhibits a viscosity at 20 weight percent solution in toluene at 30° C. of about 78,000 cps, at 5 weight percent of about 27 cps, at 10 weight percent of about 1220 cps, and at 20 weight percent 78,000 cps. Kuraray SEPS 2005 polymer exhibits a viscosity at 5 weight percent solution in toluene at 30° C. of about 28 cps, at 10 weight percent of about 1200 cps, and at 20 weight percent 76,000 cps. Other grades of S-EB-S, SEPS, $(SEB)_n$, $(SEP)_n$ polymers can also be utilized in the present invention provided such polymers exhibits the required high viscosity. Such S-EB-S polymers include (high viscosity) Kraton G 1855X which has a Specific Gravity of 0.92, Brookfield Viscosity of a 25 weight percent solids solution in toluene at 25° C. of about 40,000 cps or about 8,000 to about 20,000 cps at a 20 weight percent solids solution in toluene at 25° C.

The styrene to ethylene and butylene (S:EB) weight ratios for the Shell designated polymers can have a low range of 20:80 or less. Although the typical ratio values for Kraton G 1651, 4600, and 4609 are approximately about 33:67 and for Kraton G 1855X approximately about 27:73, Kraton G 1654X (a lower molecular weight version of Kraton G 1651 with somewhat lower physical properties such as lower solution and melt viscosity) is approximately about 31:69, these ratios can vary broadly from the typical product specification values. In the case of Kuraray's S-EB-S polymer 8006 the S:EB weight ratio is about 35:65. In the case of Kuraray's 2005 (SEPS), and 2006 (SEPS), the S:EP weight ratios are 20:80 and 35:65 respectively. The styrene to ethylene-ethylene/propylene (S:EB-EP) ratios of Kuraray's SEPTON 4033, 4045, 4055, and 4077 are typically about 30, 37.6, 30, 30 respectively. More typically the (S:EB-EP) and (S:EP) ratios can vary broadly much like S:EB ratios of S-EB-S and $(SEB)_n$ from less than 19:81 to higher than 51:49 (as recited above) are possible. It should be noted that multiblock copolymers including SEPTON 4033, 4044, 4045, 4055, 4077, 4099 and the like are described in my cited copending parent applications and are the subject matter of related inventions.

The block copolymers such as Kraton G 1654X having ratios of 31:69 or higher can be used and do exhibit about the same physical properties in many respects to Kraton G 1651 while Kraton G 1654X with ratios below 31:69 can also be use, but they are less advantageous due to their decrease in the desirable properties of the final gel.

Plasticizers particularly advantageous for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight.

Selected amounts of any compatible plasticizers can be utilized in forming the invention gels of the invention, but because of the non-tack property of the invention gels of the invention, the major amount of plasticizers used should be low viscosity plasticizers having viscosities advantageously of not greater than about 30 cSt @ 40° C.

Examples of representative commercially available plasticizing oils include Amoco® polybutenes, hydrogenated polybutenes, polybutenes with epoxide functionality at one end of the polybutene polymer, liquid poly(ethylene/butylene), liquid hetero-telechelic polymers of poly(ethylene/butylene/styrene) with epoxidized polyisoprene and poly (ethylene/butylene) with epoxidized polyisoprene: Example of such polybutenes include: L-14 (320 Mn), L-50 (420 Mn), L-100 (460 Mn), H-15 (560 Mn), H-25 (610 Mn), H-35 (660 Mn), H-50 (750 Mn), H-100 (920 Mn), H-300 (1290 Mn), L-14E (27–37 cst @ 100° F. Viscosity), H-300E (635–690 cst @ 210° F. Viscosity), Actipol E6 (365 Mn), E16 (973 Mn), E23 (1433 Mn), Kraton L-1203, EKP-206, EKP-207, HPVM-2203 and the like. Example of various commercially oils include: ARCO Prime (55, 70, 90, 200, 350, 400 and the like), Duroprime and Tufflo oils (6006, 6016, 6016M, 6026, 6036, 6056, 6206, etc), other white mineral oils include: Bayol, Bernol, American, Drakeol, Ervol, Gloria, Kaydol, Litetek, Lyondell (Duroprime 55, 70, 90, 200, 350, 400, Ideal FG 32, 46, 68, 100, 220, 460), Marcol, Parol, Peneteck, Primol, Protol, Sontex, and the like. Oils useful in the invention gel include: Witco 40 oil, Ervol, Benol, Blandol, Semtol-100, Semtol 85, Semtol 70, Semtol 40, Orzol, Britol, Protol, Rudol, Carnation, Klearol; 350, 100, 85, 70, 40, Pd-23, Pd 25, Pd28, FG 32, 46, 68, 100, 220, 460, Duroprime Ds-L, Ds-M, Duropac 70, 90, Crystex 22, Af-L, Af M 6006, 6016, 6026, Tufflo 6056, Ste Oil Co, Inc: Invention Plus 70, 200, 350, Lyondell: Duroprime DS L & M, Duropac 70, 90, Crystex 22, Crystex AF L & M, Tufflo 6006, 6016; Chevron Texaco Corp: Superta White Oil 5, Superta 7, 9, 10, 13, 18, 21, 31, 35, 38, 50, Penreco: Conosol 340, Conosol C-200, Drakeol 15, 13, 10, 10B, 9, 7, 5, 50, Peneteck, Ultra Chemical Inc, Ultraol White 60Nf, Ultraol White 50Nf, Witco Hydrobrite 100, 550, 1000, and the like.

Selected amounts of one or more compatible plasticizers can be used to achieve gel rigidities of from less than about 2 gram Bloom to about 1,800 gram Bloom and higher. Tack may not completely be dependent upon the amount of the glassy phase, by using selected amount of certain low viscosity oil plasticizers, block copolymers of SEBS, SEEPS, SEPS, SEP$_n$, SEB$_n$, and the like, gel tack can be reduced or the gel can be made non-tacky.

Major or minor amounts (based on 100 parts by weight of base elastomer) of any compatible second plasticizers can be utilized in forming the invention gel, but because of the non-tack property of the invention gel, the major amount of first plasticizers used should be low viscosity plasticizers having viscosities advantageously of not greater than about 30 cSt @ 40° C., for example values and in between: 30, 29, 28, 27, 26, 25, 24, 23, 22, 21, 20, 19, 18, 17, 16, 15, 14, 13, 12, 11, 10, 9, 8, 7, 6, 5, 4, 3 and the like. Such low viscosity plasticizers are commercially available as, for example, from Witco: Rudol, Ervol, Benol, Blandol, Carnation, Klearol, Semtol 100, Semtol 85, Semtol 70, Semtol 40; from Lyondell: Duroprime 55, 70, 90, Durprime DS L & M, Duropac 70, 90, Crystex 22, Crystex AF L & M, Tufflo 6006, 6016 and the like. The invention gel tack decreases with decreasing oil viscosities of from about 30 to 3. Invention gels which are non-tacky to the touch can be achieved using oils with viscosities of about 10 cSt @ 40° C. and less. Best result can be achieved using oils with viscosities of about 6 and less. Oils of higher viscosities of from about 500 cSt @ 40° C. to about 30 produce higher and higher tack with increase in viscosities. Heat temperature set resistance improves with increase in oil viscosity. Oils with viscosities less than about 15 exhibit heat set at about 50° C. Therefore a combination of low viscosity oils to improve low tack and high viscosity oils to improve set can be achieved by blending various oils having the desired viscosities for the desired end use. The disassociation of polystyrene is about 100° C. to about 135° C., the invention gels do not melt below the disassociation temperature of polystyrene. It is important that fishing bait when stored in a fishing box in the hot Sun at about 50° C. to about 58° C. do not suffer substantial heat set as tested at these temperatures in a 108° U bend for one hour.

It has been found that the lower the oil viscosity, the lower the heat set of the resulting gel composition and the higher the oil viscosity use in the gel compositions of the invention, the higher the heat set of the resulting gel composition. For example, if the first plasticizer is less than about 50 SUS @ 100° F., the heat set of the resulting gel composition comprising 100 parts of (I) copolymers of equal parts of SEEPS 4055 and Kraton G 1651 with about 600 parts by weight of the first plasticizer, the resulting is found to have a heat set less than that of a conventional PVC plastisol fishing bait at about 50° C. However, as the 50 Vis SUS @ 100° F. oil of the formulation is gradually replaced with a higher viscosity oil of about 80–90 SUS @ 100° C., the heat set deformation improves with increasing amounts of the higher viscosity oil. In order to obtain equal heat set performance as conventional PVC plastisol fishing bait, the first and second plasticizers would have to be of equal amounts in the gel composition. Replacing the first plasticizer with a greater amount would increase the gel tack. If tack is not of great concern, then a higher amount of the second plasticizers would be beneficial for improving heat set at higher and higher temperatures to the point that the second plasticizers can reach greater than 2525 SUS @ 100° C. (Ideal FG 100, 220, or 460 oil) the resulting gel composition would not exhibit set at even temperatures greater than 400° F.

The cited first plasticizers with or without one or more second plasticizers can be used in sufficient amounts to achieve a gel rigidity of from about 20 gram Bloom to about 1,800 gram Bloom. The second plasticizers in effective amounts in combination with the first plasticizers can provide a greater temperature compression set than a gelatinous composition having the same rigidity formed from the first plasticizers alone. The second plasticizers when used can provide a greater temperature compression set than a gelatinous composition having the same rigidity formed from the first plasticizers alone or formed from a combination of the first plasticizers and the second plasticizers. The first plasticizers being in effective amounts with said second plasticizers can provide a Gram Tack lower than a gelatinous composition having the same rigidity formed from the second plasticizers alone.

Generally, plasticizing oils with average molecular weights less than about 200 and greater than about 700 may also be used (e.g. H-300 (1290 Mn)). It is well know that minor and sufficient amounts of Vitamin E is added to the described commercially available oils during bulk processing which is useful as a oil stabilizer, antioxidant, and preservative.

Of all the factors, the amount of plasticizing oils can be controlled and adjusted advantageously to obtain substantially higher tear and tensile strength gels. The improvements in tensile strength of the invention gels are accompanied by corresponding increase in gel rigidity as the amount of plasticizing oils are lowered until the rigidity of the invention gels becomes much higher than that of the gums which surround the teeth. Although higher tensile strengths can be obtained as the amount of plasticizing oils in the gel approaches zero, the tensile strength of the floss, however, must be maintained at an acceptable gel rigidity (at sufficient high plasticizing oil levels) in order to be as soft as the gums required for flossing. For example, the rigidities of a gel containing 100, 200, or 300 parts by weight of oil is much higher than a gel containing 300, 400, 500, 600, 800, or 900 parts of oil.

These gels can exhibit a larger unit lateral contraction at the same elongation per unit of length as their counterpart parent gels from which the invention gels are derived or formed. This property would allow a same unit volume of gel when elongated as its parent to easily wedge between the teeth when flossing. It would seem that a gel having the 1.0 cm$^3$ volume made from a ratio of 100 parts by weight of copolymer and 400 parts plasticizer would have a unique macro volume configurations that is at equilibrium with the plasticizer which is much like a 3-D fingerprint which is uniquely different from any other gel of a different copolymer to plasticizer ratio. Reducing the plasticizer content of a ratio 100:400 gel to a 100:300 ratio of copolymer to plasticizer will decrease the amount of plasticizer, but the original macro volume configurations will remain the same.

Speculative theories not withstanding, configurations may take the form of (1) swiss cheese, (2) sponge, (3) the insides of a loaf of bread, (4) structures liken to ocean brain corals, (5) large structures and small structures forming the 3-D gel volume landscape, (6) the outer heated surface which cools faster than the inner volumes of the gel during its cooling histories may have a patterned crust (rich in A micro-phases) like that of a loaf of bread and the inner volume may have much like 1–5, and (7) the many different possible structures are unlimited and volume landscapes may be interconnected at the macro-level by threads or micro-strands of Z microphases.

The amount of plasticizer extracted can advantageously range from less than about 10% by weight to about 90% and higher of the total weight of the plasticizer. More advantageously, the extracted amounts of plasticizer can range from less than about 20% by weight to about 80% by weight of the total plasticizer, and still more advantageously, from about 25% to about 75%. Plasticizing oils contained in the invention gels can be extracted by any conventional methods, such as solvent extraction, physical extraction, pressure, pressure-heat, heat-solvent, pressure-solvent-heat, vacuum extraction, vacuum-heat extraction, vacuum-pressure extraction, vacuum-heat-pressure extraction, vacuum-solvent extraction, vacuum-heat-solvent-pressure extraction, etc. The solvents selected, should be solvents which do not substantially disrupt the A and Z phases of the (I) copolymers forming the invention gels. Any solvent which will extract plasticizer from the gel and do not disrupt the A and Z phases can be utilized. Suitable solvents include alcohols, primary, secondary and tertiary alcohols, glycols, etc., examples include methanol, ethanol, tetradecanol, etc. Likewise, the pressures and heat applied to remove the desired amounts of oils should not be sufficient to disrupt the A and Z domains of the (I) copolymers. To form a lower rigidity gel, the simplest method is to subject the gel to heat in a partial vacuum or under higher vacuum for a selected period of time, depending on the amount of plasticizer to be extracted.

Surprisingly, as disclosed in my U.S Ser. No. 09/896,047 filed Jun. 30, 2001, oil extraction from the invention gels can be achieved with little or no energy in the presence of one or more silicone fluids to almost any degree. A theory can be made to explain the physics involved in the extraction process which reasoning is as follows: (1) When water is placed in contact with an oil extended gel, the gel will not over time exhibit weight loss. (2) When oil is add to a column of water in a test tube, the oil will separate out and find its level above the column of water. (3) The surface tension of water at 25° C. is about 72.0 mN/m. (4) The surface tension of oil (mineral oil) at 25° C. is about 29.7 mN/m. (5) The surface tension of silicone fluid at 25° C. range from abut 16 to abut 22 mN/m (for example: the surface tension of 100 cSt silicone fluid at STP is 20.9 mN/m). (6) The density of oil is less than the density of silicone fluid, silicone grease, silicone gel, and silicone elastomer. (7) Oil is not a polar liquid and is highly compatible with the rubber phase of the oil gel forming polymer. (8) Silicone is polar and not compatible with the polymer's rubber phase.

The molecules of a liquid oil drop attract each other. The interactions of an oil molecule in the liquid oil drop are balanced by an equal attractive force in all directions. Oil molecules on the surface of the liquid oil drop experience an imbalance of forces at the interface with air. The effect is the presence of free energy at the surface. This excess energy is called surface free energy and is quantified as a measurement of energy/area. This can be described as tension or surface tension which is quantified as a force/length measurement or m/Nm.

Clearly gravity is the only force pulling on the extracted oil from the gel in the presence of silicone fluid at the gel-petri dish interface in the examples below. In the case of gel samples in the petri dishes in contact with silicone fluids, the extracted oil are collected on the top surface layer of the silicone fluid while the silicone fluid maintain constant contact and surrounds the gel sample. In the case of gel placed in a test tube of silicone fluid of different viscosity, the oil is extracted and migrates and collect at the top of the silicone fluid surface while the gel reduces in volume with time. The oil extraction process in silicone is accompanied by buoyant forces removing the extracted oil from the surroundings of the gel constantly surrounding the gel with fresh silicone fluid while in the example of alcohol, since the oil is heavier, the oil is maintained and surrounds the gel sample forming a equilibrium condition of oil surround the gel sample while keeping the alcohol from being in contact with the gel sample. Therefore in order to use alcohol to extract oil from a gel sample, the extracted oil must be constantly removed from the oil alcohol mixture as is the case during soxhlet extraction which process requires additional energy to pump the oil-alcohol mixture away from the sample and removing the oil before forcing the alcohol back to the gel sample surface to perform further extraction.

Silicone fluid is efficient and useful for extracting oil form oil gel compositions with the assistance of gravity and buoyancy of oil in the silicone fluids.

It is very difficult to extract, separate, or remove oil from an oil gel composition by positive or vacuum pressure or heat while using little or no energy and because of the affinity of the rubber midblock for oil, not even the weight of a two ton truck resting on a four square foot area (placing a layer of gel between four pairs of one foot square parallel steel plates one set under each of the truck tire resting on the gels) can separate the oil from the gel composition.

The use of silicone fluids of various viscosity acts as a liquid semi porous membrane when placed in constant contact with an oil gel composition will induce oil to migrate out of the gel composition. By the use of gravity or oil buoyancy, no energy is required run the oil extraction process.

In the case of the invention gels of this application made in the shape of a fishing bait in contact with silicone fluid, the elastomer or rubber being highly compatible with the oil, holds the oil in place within the boundary of the rubber molecular phase. It is this affinity of the (i) rubber and oil molecules and (ii) the attraction of oil molecules for each other that prevents the oil from bleeding out of the surface of the gel body. There exist then, at the surface of the gel several types of surface tensions of: (iii) oil-air surface tension, (iv) oil-rubber surface tension, (v) rubber-air surface tension, (vi) rubber/oil-air surface tension, and (vii) rubber-rubber surface tension. Other forces acting on the gel are: the elastic force of the polymer network pulling inwards, similar to stretched out rubber bands, which is in equilibrium with the oil molecules' attraction to the rubber molecules of the polymer network. In the case of SBS, the lower compatibility of the midblock butadiene with oil, once a gel is made, the SBS network immediately contracts due to elastic forces to produce oil bleeding which is evidence of the poor compatibility of the rubber block for the oil molecules.

The intermolecular forces that bind similar molecules together are called cohesive forces. Intermolecular forces that bind a substance to a surface are called adhesive forces.

When two liquids are in contact such as oil and silicone fluid, there is interfacial tension. The more dense fluid is referred to herein as the "heavy phase" and the less dense fluid is referred to as the "light phase". The action at the surface of the oil extended polymer gel surface when brought into contact with silicone fluid is as follows: a drop of silicone fluid when placed on the flat surface of a oil extended polymer gel will wet the gel surface and spread over a larger area as compared to a drop of oil placed on the same gel surface. Because the surface free energy of the silicone fluid in contact with the gel surface is lower than the surface free energy of the oil, the silicone fluid has the ability to displaces the oil from the surface of the gel.

The invention gels can optionally comprise selected major or minor amounts of one or more polymers or copolymers (III) provided the amounts and combinations are selected without substantially decreasing the desired properties. The polymers and copolymers can be linear, star-shaped, branched, or multiarm; these including: (SBS) styrene-butadiene-styrene block copolymers, (SIS) styrene-isoprene-styrene block copolymers, (low styrene content SEBS such as Kraton 1650 and 1652) styrene-ethylene-butylene-styrene block copolymers, (SEP) styrene-ethylene-propylene block copolymers, (SEPS Kraton RP-1618) styrene-ethylene-propylene-styrene block copolymers, $(SB)_n$ styrene-butadiene and $(SEB)_n$, $(SEBS)_n$, $(SEP)_n$, $(SI)_n$ styrene-isoprene multi-arm, branched or star-shaped copolymers, polyethyleneoxide (EO), poly(dimethylphenylene oxide) and the like. Still, other (III) polymers include homopolymers which can be utilized in minor amounts; these include: polystyrene, polybutylene, polyethylene, polypropylene and the like.

In the case of high molecular weight and combination of high styrene content of the block copolymer which may be the reason for improve tear and fatigue resistance, these properties may be achieved and maintained by blending (I) copolymers of SEEPS with (III) copolymers of SBS (Kraton D 1101, 1144, 1116, 1118, 4141, 4150, 1133, 1184, 4158, 1401P, 4240, and KX219), SEBS (G1651, 1654).

Other (III) polymers useful in the invention gels include: of trifluoromethyl-4,5-difuoro-1,3-dioxole and tetrafluoroethylene, polytetrafluoroethylene, maleated poly(styrene-ethylene-butylene), maleated poly(styrene-ethylene-butylene)n, maleated poly(styrene-ethylene-butylene-styrene), maleated poly(styrene-ethylene-propylene)n, maleated poly(styrene-ethylene-propylene-styrene), poly(dimethylphenylene oxide), poly(ethylene-butylene), poly(ethylene-propylene), poly(ethylene-styrene) interpolymer made by metallocene catalysts, using single site, constrained geometry addition polymerization catalysts, poly(styrene-butadiene), poly(styrene-butadiene)n, poly(styrene-butadiene-styrene), poly(styrene-ethylene-butylene), poly(styrene-ethylene-butylene)n, poly(styrene-ethylene-butylene-styrene), poly(styrene-ethylene-butylene-styrene), poly(styrene-ethylene-propylene), poly(styrene-ethylene-propylene)n, poly(styrene-ethylene-propylene-styrene), poly(styrene-isoprene), poly(styrene-isoprene)n, poly(styrene-isoprene-styrene), poly(styrene-isoprene-styrene)n, polyamide, polybutylene, polybutylene, polycarbonate, polydimethylsiloxane; polyethylene vinyl alcohol copolymer, polyethylene, polyethyleneoxide, polypropylene, polystyrene, polyvinyl alcohol, wherein said selected copolymer is a linear, radial, star-shaped, branched or multiarm copolymer, wherein n is greater than one When the selected (III) polymers and copolymers contain greater glassy block of styrene content of 33 and higher, such may be effective to provide a Gram Tack lower than a gelatinous composition having the same rigidity formed from the (I) block copolymers and corresponding first plasticizers alone or the first plasticizers with a second plasticizers. The selected component (III) polymers of polystyrene forming a styrene content of 33 and higher when used in effective amounts may provide a greater temperature compression set than a gelatinous composition having the same rigidity formed from the (I) block copolymers and corresponding first plasticizers alone or the first plasticizers with a second plasticizer.

On the other hand, the lower viscosity first plasticizer can impart lower Grain Tack to the invention gels than an increase of styrene content of the (I) copolymers or (III) polymers and copolymers. The low tack and non tacky invention gels can be made from one or more linear, branched, star-shaped (radial), or multiarm block copolymers or mixtures of two or more such block copolymers having one or more midblock polymer chains which invention gels have use as articles with high tear propagation resistance. The invention gels also possess high tensile strength and rapid return from high extension and can exist in an altered state of delay elastomeric recovery as it regains its original shape following high extensions or dynamic deformations. The invention gels also exhibit low set, high dimensional stability, crack, tear, craze, and creep resistance, excellent tensile strength and high elongation, long service life under shear, stress and strain and capable of withstanding repeated dynamic shear, tear and stress forces, excellent processing ability for cast molding, extruding, fiber forming film forming and spinning, non-toxic, nearly tasteless and odorless, soft and strong, optically clear, highly flexible, possessing elastic memory, substantially with little or no plasticizer bleedout, and having low or no tack in contact with human hand which reduction in tackiness can be measured. The non tacky and optical properties of the invention gels do not rely on powders or surface activation by additives to establish their non-tackiness. The invention gels' non-tackiness pervasive the gels' entire bulk or volume. No matter how deep or in which direction a cut is made, the invention gels are non tacky throughout (at all points internally as well as on the gels' surface). Once the gel is cut, the invention gel immediately exhibits non-tackiness at its newly cut surface. Hence, the homogeneity of the non-tackiness and optical properties of the invention gels are not known.

Because of their improved tear resistance and resistance to fatigue, the gel compositions and s of the invention including the fluffy invention gels disclosed in U.S. Ser. No. 08/984,459 (incorporated above by reference) exhibit versatility as materials formed into hollowed thick wall body shapes for use in deep sea ice water diving or insulating the body from extreme cold. The fluffy invention gels are advantageously useful for making one layer gloves for vibration damping which prevents damage to blood capillaries in the fingers and hand caused by handling strong shock and vibrating equipment.

As described in my U.S. Pat. No. 6,324,703, because of invention gel improved tear resistance and resistance to fatigue, the invention gels including fluffy gels exhibit versatility as materials formed into hollowed thick wall body shapes for use in deep sea ice water diving or insulating the body from extreme cold. With respect to the Drawings: FIGS. 1–14B, we adopt the following convention: For example, the composite of FIG. 1 is denoted by $G_n(G_nM_m)M_mM_n$, a composite. The composite "$G_n(G_nM_m)M_mM_n$" comprises a $G_n$ layer laminated to a "$(G_nM_m)$" layer. The $(G_nM_m)$ layer with the "( . . . )" denotes a gel composition of Mm that is dispersed in $G_n$. Next, the $(G_nM_m)$ layer is laminated to a $M_n$ layer which is laminated to another $M_n$ layer. When the subscript m is the subscript of M, m denotes the same or a different dispersion material. When n is a subscript of M, n is the same or different selected from the group consisting of paper, foam, plastic, concrete, fabric, metal, concrete, wood, glass, ceramics, synthetic resin, synthetic fibers or refractory materials. Where n is the subscript of $G_n$, n denotes the same or a different gel G with the same or a different rigidity.

Figure 7:
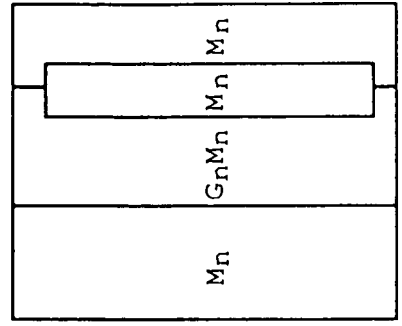
Figure 17:
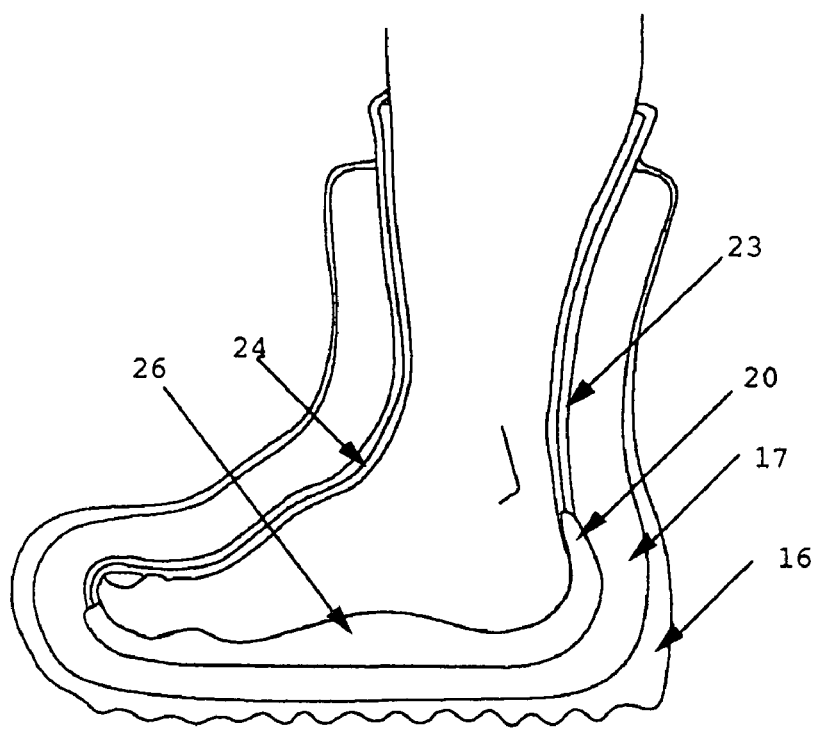
FIG. 17. Illustrate embodiments of insulating gels and insulating gel composites in cross-sectional views of foot wear.
Figure 22:
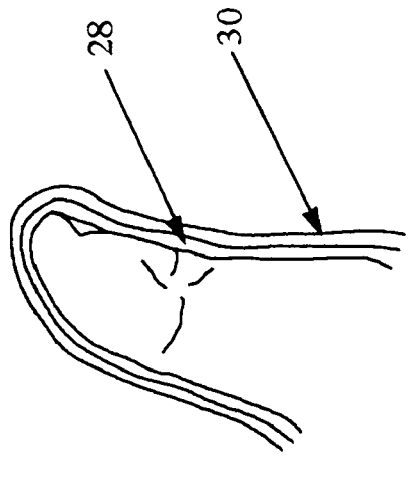
FIGS. 21–22. View of thumb finger representing the hand with cross-sectional of insulating gel and insulating gel composite gloves.
Figure 21:
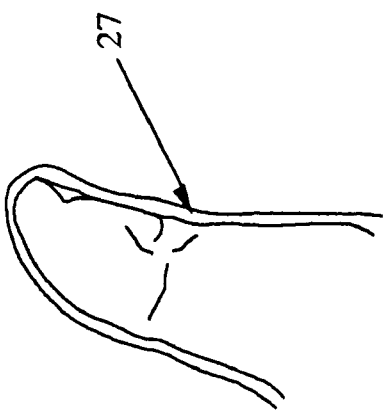
Figure 20:
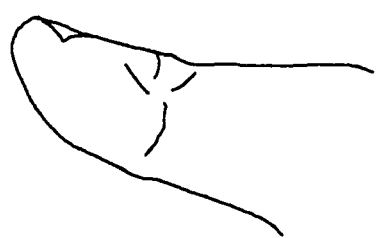
FIG. 20. View of thumb finger representing the hand.

Thus by convention, $(G_nM_m)$, denotes a gel $G_n$ with a homogenous or non-homogenous dispersion of a material $M_m$. As another example, FIG. 7 is denoted by $M_n(G_nM_m)M_nM_n$, FIG. 9 is denoted by $M_n(G_nM_m)M_n$, FIG. 10B is denoted by $M_nG_nM_n$, FIG. 11 is denoted by $G_nM_n$, FIG. 13 is denoted by $G_nM_nG_nM_n$, FIG. 14B is denoted by $G_nM_nG_n$, and the like.

Of great advantage are the unexpanded particulate materials which can be dispersed and within a controlled temperature heating range can produce a predetermined volume of closed cell particulate dispersions forming the fluffy gels. The particulate materials useful are unexpanded microspheres of poly(acrylonitrile-methacrylonitrile) copolymers encapsulated liquid isopentane which are available from Akzo Nobel by the tradename Expancel. The thermoplastic microspheres comprises about 80% weight of copolymer and about 6 to about 16% isopentane and are further characterized as having a unexpanded relative density of about 1.2 ($H_2O$=1.0), particle size of about 3 to about 50 microns, a $T_{start}$ or softing temperature of about 106° C. to about 135° C. and a decomposition or rupturing temperature $T_{max}$ of about 138° C. to about 195° C. The unexpanded thermoplastic microspheres are activated by heat and expand to approximately about 50 times its unexpanded size to provide an average particle density of about less than 0.020 specific gravity. Their lowest calculated density reached at $T_{max}$ during TMA test is between about 0.25 to about 0.017 g/cm³. More specifically, unexpanded grades of microspheres include grades followed by (range of temperatures $T^{start\ °C.}/T_{max}^{°C.}$) #051 (106–111/138–147), #053 (95–102/137–145), #054 (125–135/140/150), #091 (118–126/161–171), #091–80 (118–126/171–181), and #092–120 (118–126/185–195).

The invention gels can be casted molded, pressured molded, injection molded and various methods of forming gel articles and with or without interlocking with various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten invention gel is deformed as it is being cooled. Useful open-cell plastics include: polyamides, polyimides, polyesters, polyisocyanurates, polyisocyanates, polyurethanes, poly(vinyl alcohol), etc. Suitable open-celled Plastic (sponges) are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The instant gel compositions and s including fluffy gels are excellent for cast, injection, or spinning molding and the molded products have high tear resistance characteristics which cannot be anticipated form the properties of the raw components. Other conventional methods of forming the composition can be utilized. The invention gel compositions and s including fluffy gel articles can be formed by blending, injection molding, extruding, spinning, casting, dipping and other conventional methods. For example, Shapes having various cross-section can be extruded. The fluffy invention gels can also be formed directly into articles or remelted in any suitable hot melt applicator and extruded into shaped articles and films or spun into threads, strips, bands, yarns, or other shapes.

Comparisons of oil extended S-EB-S triblock copolymers have been described in Shell Chemical Company Technical Bulletin SC: 1102-89 (April 1989) "KRATON® THEMOPLASTC RUBBERS IN OIL GELS" which is incorporated herein by reference.

The stearic acid and microcrystalline wax components of the gels described in my earlier U.S. Pat. No. 5,760,117 are non-sticky, invention and non-adhering. The non-adhering gels containing additives such as stearic acid and the like, however, feels greasy due the additive's high solubility in oil and low melting points forming a greasy coating on the surface of the gel. The inherently invention gels which are an improvement over the greasy feeling gels of U.S. Pat. No. 5,760,117 described above, although feels non-adhering and completely non-tacky and non-greasy, can exhibit a high coefficient of friction or high COF.

Figure 5A:
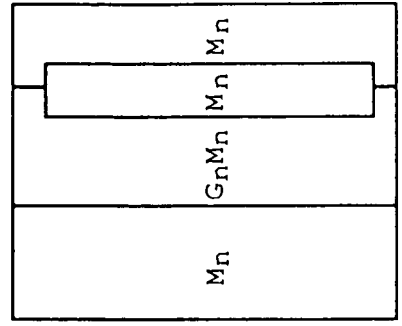
Figure 5B:
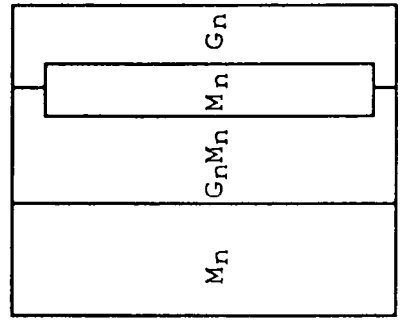

I have also found that by incorporating sufficient amounts of one or more of a selected (high melting, low oil soluble, and polar) low COF agents (such as polyphenolics with one or more sterically hindered phenolic hydroxyl groups) in the gels will result in the appearance of large crystals in the interior as well as on the surface of the gels. Such crystals are shown in FIG. 5 (top view) photo of the top of a invention gel article with phenolic crystals. These crystals have no effect on the high COF of the resulting gels. Contrary to the combined effects of stearic acid and microcrystalline wax, the presence of microcrystalline wax with polyphenolic in gels does not lessen the gel's COF and have little effect on reducing the size of the large polyphenolic crystals. Likewise the crystallinity and glassy components by themselves can not by themselves reduce the inherent high COF of these gels. Consequently, gels containing microcrystalline wax and polyphenolics exhibit high COF.

Surprisingly, when selected amounts of internal nucleating agents are incorporated in the gels in combination with selected amounts of one or more of a low COF agents, the large crystals no longer forms within the gels; and the surface of the gels exhibit lower and lower COF with time. Bringing the gels in contact with selected external nucleating agents decreases the time or totally eliminates the time needed for the gel's outer surface to exhibit a low COF.

The gels and soft elastomers incorporating low COF agents and internal and/or external nucleating agents exhibit a much lower coefficient of friction when measured in contact with a reference surface than gels and soft elastomers made without such components.

School book physics teaches COF can be determined experimentally, for two given surfaces that are dry and not lubricated, the ratio of the tangential force needed to overcome the friction to the normal force which holds the two surfaces in contact (e.g., the weight of a block of gel or elastomer material on a surface) is a constant, independent of the area or of the velocity with which the surfaces (surface of a side of the block in contact with another surface) move over wide limits. This ratio is μ, the coefficient of friction. The coefficient of sliding friction for a block of material being $$\mu = (f/F_n)$$

where f is the force of friction, and $F_n$ the normal force. For the case of the block on the horizontal table, if m is the mass of the block, then mg is the normal force and the above equation can be written as $$\mu = f/mg.$$

In the case the block of a block rests on a board, originally horizontal, and that the board then is tilted until a limiting angle ø is reached, beyond which the block will begin to slide down the board. At this angle the component of the weight of the object along the board is just equal in amount to that necessary to overcome the force of friction. The force down the plane is mg sin ø, while the normal force is mg cos ø. Therefore we have $$\mu = (mg\ \sin\ \text{ø})/(mg\ \cos\ \text{ø})\ \text{or}\ \mu = \tan\ \text{ø}.$$

The limiting value of ø for which p=tan ø is true is call the angle of repose. Measurement of the tangent of this angle will give the coefficient of friction of the contacting surfaces of the block and the board that slide one upon the other.

As an example of low COF agents advantageously useful in soft thermoplastic elastomers and gels, excellent results is achieved with 50 grams of a polyphenolic with sterically hindered phenolic hydroxyl groups (Irganox 1010), about 100 grams of one or more nucleating agents (such as very fine particle size sodium benzoate, dibenzylidene sorbitol, its alkylated derivatives, talc, zinc sterate, amorphous silica, aluminum sterate, etc.) and 5,000 grams of S-EB-S and 25,000 gram of oil. The same excellent result is achieved when S-EB-S is adjusted to 3,000 grams, 4,000 grams, etc. The same result is achieved with copolymers as well as in combination with other polymers. Moreover, when about 50 grams of tetrakis[methylene 3,-(3'5'-di-tertbutyl-4"-hydroxyphenyl) propionate] methane is use (per about 22.68 Kilograms or 50 lbs of gel) as a low COF agent, tack is completely removed from the surface of the gel after two to three weeks of blooming.

Figure 6:
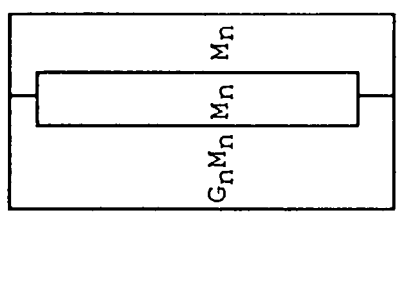

When this is repeated with an external nucleating agent, such as with various fine particles for coating the outside surface of the elastomer or gel, such as with talc, calcium stearate, zinc sterate, amorphous silica, aluminum sterate, fine flour, corn starch, fine soil, fine sand, fine metallic powder, vacuum dust, fine wood dusts and the like, lower COF is achieved within a few days to less than several hours. After coating the gel for the desired period of time, the fine polar and water soluble particles can be washed off with water and soap, while non-polar and non-water soluble fine powders can be removed by wearing it off or by lifting it off with the use of adhesive tapes if so desired. FIG. 6. (top view) photo of the top of a invention gel article made with phenolics and external nucleating agents.

What is the surface properties of low CFO agents at the air/plasticizer-copolymer interface? Theory notwithstanding, the resulting gel surface will comprise of very fine molecular segments or even very fine invention grains of low COF agents confined at the air/plasticizer and polymer interface. Depending on concentration, the non-polar segments of the low COF agents will have a tendency of being adsorped by the predominate plasticizer and copolymer midblock phase at the gel surface. The slightly polar or more polar segments of the low COF agents are adsorbed to a lesser extent by the plasticizer-copolymer surface. This is supported by observing the water wetting characteristics at the gel surface with and with out low COF agents at the air gel surface interface. A drop of water will bead up and not readily wet the gel surface free of any low COF agents (hydrophobic). The presence of even slightly polar low COF agents exposed on the surface of the gel will make a drop of water flatten out and not bead up when place on the gel surface (hydrophilic).

Commercial high melting point, low oil solubility, and polar low COF agents such as polyphenolics which are advantageously useful in the present invention include: Ethanox 330 (Ethyl), Irganox 1010 (Ciba-Geigy), Santechhem A/O 15-1 (Santech), Ultra 210 (GE), Hostanox 03 (Hoechst Celanese), Irganox 3114 (Ciba-Geigy), Mixxim AO-3 (Fairmont), and the like. Other high melting point, low oil solubility, polar low COF agents contemplated are common amino acids: Such As Alamine, Arginine, Asparagine, Aspartic Acid, Cysteine, Glutamine, Glutamic Acid, Glycine, Histidine, Isoleucine, Leucine, Lysine, Methionine, Phenylalanine, Proline, Serine, Threonine, Tryptophan, Tyrosine and Valine. The melting points of these amino acids range from about 178° C. to about 344° C. The amino acids having greater advantage serving as low COF agents are Asparagine, Aspartic acid. Glutamine, Glutamic acid, Tryptophan, and Tyrosine.

Copolymer for forming the low COF compositions include block copolymers, random copolymers, metallocene catalyzed ethylene styrene copolymers, Low COF invention gels made from thermoplastic elastomer copolymers and block copolymers having one or more crystalizable polyethylene segments or midblocks. The low COF invention gels advantageously exhibit high, higher, and higher, and ever higher tear resistance than realized before as well as improved high tensile strength. The low COF invention gels also exhibit improved damage tolerance, crack propagation resistance and especially improved resistance to high stress rupture which combination of properties makes the gels advantageously and surprisingly suitable for use as toys, inflatable air cushions in automobiles, and the like.

The invention gels of this invention are advantageously useful for making low COF gel compositions. Moreover, various polymer gels made from linear triblock copolymers, multi-arm block copolymers, branched block copolymers, radial block copolymers, multiblock copolymers, random/non-random copolymers, thermoplastic crystalline polyurethane copolymers with hydrocarbon midblocks or mixtures of two or more of such copolymers can also be made with low COF. The COF values of the invention gels formed form the low COF and nucleating agents are found to be about less than 1, more advantageously less than 0.7, more advantageously less than 0.577, still more advantageously less than 0.466 and still more advantageously less tan 0.40. The low COF invention gels of the invention can range from less than 1.0 to about less than 0.40.

As taught in my application Ser. No. 08/288,690 filed Aug. 11, 1994, now U.S. Pat. No. 5,633,286 and specifically incorporated herein, additives useful in the gel of the present invention include: tetrakis[methylene 3,-(3'5'-tertbutyl-4"-hydroxyphenyl)propionate]methane, octadecyl 3-(3",5"-di-tert-butyl-4"-hydroxyphenyl)propionate, distearyl-pentaerythritol-diproprionate, thiodiethylene bis-(3,5ter-butyl-4-hydroxy)hydrocinnamate, (1,3,5-trimethyl-2,4,6-tris[3,5-di-tert-butyl-4-hydroxybenzyl]benzene), 4,4"-methylenebis (2,6-di-tert-butylphenol), stearic acid, oleic acid, stearamide, behenamide, oleamide, erucamide, N,N"-ethylenebisstearamide, N,N"-ethylenebisoleamide, sterryl erucamide, erucyl erucamide, oleyl palmitamide, stearyl stearamide, erucyl stearamide, calcium sterate, other metal sterates, waxes (e.g. polyethylene, polypropylene, microcrystalline, carnauba, paraffin, montan, candelilla, beeswax, ozokerite, ceresine, and the like). The gel can also contain metallic pigments (aluminum and brass flakes), TiO2, mica, fluorescent dyes and pigments, phosphorescent pigments, aluminatrihydrate, antimony oxide, iron oxides (Fe3O4, — Fe2O3, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite and the like. The report of the committee on Magnetic Materials, Publication NMAB-426, National Academy Press (1985) is incorporated herein by reference.

The invention gels can also be made into s. The invention gels can be casted unto various substrates, such as open cell materials, metals, ceramics, glasses, and plastics, elastomers, fluropolymers, expanded fluropolymers, Teflon (TFE, PTFE, PEA, FEP, etc), expanded Teflon, spongy expanded nylon, etc.; the molten invention gel is deformed as it is being cooled. Useful open-cell plastics include: polyamides, polyimides, polyesters, polyisocyanurates, polyisocyanates, polyurethanes, poly(vinyl alcohol), etc. Suitable open-celled Plastic (sponges) are described in "Expanded Plastics and Related Products", Chemical Technology Review No. 221, Noyes Data Corp., 1983, and "Applied Polymer Science", Organic Coatings and Plastic Chemistry, 1975. These publications are incorporated herein by reference.

The invention gels are prepared by blending together the components including other additatives as desired at about 23° C. to about 100° C. forming a paste like mixture and further heating said mixture uniformly to about 150° C. to about 200° C. until a homogeneous molten blend is obtained. Lower and higher temperatures can also be utilized depending on the viscosity of the oils and amounts of multiblock copolymers and polymer used. These components blend easily in the melt and a heated vessel equipped with a stirrer is all that is required. Small batches can be easily blended in a test tube using a glass stirring rod for mixing. While conventional large vessels with pressure and/or vacuum means can be utilized in forming large batches of the invention gels in amounts of about 40 lbs or less to 10,000 lbs or more. For example, in a large vessel, inert gases can be employed for removing the composition from a dosed vessel at the end of mixing and a partial vacuum can be applied to remove any entrapped bubbles. Stirring rates utilized for large batches can range from about less than 10 rpm to about 40 rpm or higher.

The gel compositions can also be formed directly into articles or remelted in any suitable hot melt applicator and extruded or spun into threads, bands, or other shapes. The instant compositions is excellent for cast molding and the molded products have various excellent characteristics which cannot be anticipated form the properties of the raw components. Other conventional methods of forming the composition can be utilized.

As taught in my application Ser. No. 08/288,690 filed Aug. 11, 1994, now U.S. Pat. No. 5,633,286 and specifically incorporated herein, the gelatinous clastomer composition of the invention is excellent for forming the gelatinous elastomer articles of the invention. The gelatinous elastomer articles can be formed by blending, melting, dipping, casting, injection molding, extruding and other conventional methods. For example, a foam of a preselected pore size can be placed in a mold cavity and a preselected amount of a preselected rigidity of gelatinous elastomer composition is then injected into the mold. The mold is allow to cool to room temperature and the article removed. A preselected rigidity of molten gelatinous elastomer composition can be cast directly onto a section of open cell foam to form the article. Likewise, an article of foam can be dipped into a preselected rigidity of molten gelatinous elastomer composition and re-dipped into the same or different composition of a different rigidity. The shaped article of the invention can be conventionally covered with protective skins of elastomeric film, fabric or both as needed.

The composition can also be remelted in any suitable hot melt applicator for hot dipping, extrusion, sputtering, or spraying on to the foams or sponges so as to form the gelatinous elastomer articles of the invention.

As taught in my application Ser. No. 08/288,690 filed Aug. 11, 1994, now U.S. Pat. No. 5,633,286 and specifically incorporated herein, generally the molten gelatinous elastomer composition will adhere sufficiently to certain plastics (e.g. acrylic, ethylene copolymers, nylon, polybutylene, polycarbonate, polystyrene, polyester, polyethylene, polypropylene, styrene copolymers, and the like) provided the temperature of the molten gelatinous elastomer composition is sufficient high to fuse or nearly fuse with the plastic. In order to obtain sufficient adhesion to glass, ceramics, or certain metals, sufficient temperature is also required (e.g. above 250° F.). Commercial resins which can aid in adhesion to materials (plastics, glass, and metals) may be added in minor amounts to the gelatinous elastomer composition, these resins include: Super Sta-tac, Nevtac, Piccotac, Escorez, Wingtack, Hercotac, Betaprene, Zonarez, Nirez, Piccolyte, Sylvatac, Foral, Pentalyn, Arkon P, Regalrez, Cumar LX, Picco 6000, Nevchem, Piccotex, Kristalex, Piccolastic, LX-1035, and the like. The conventional term "major" means about 51 weight percent and higher (e.g. 55%, 60%, 65%,70%, 75%, 80% and the like) and the term "minor" means 49 weight percent and lower (e.g. 2%, 5%, 10%, 15%, 20%, 25% and the like to less than 50%)(based on 100 parts of (I)).

For example, Shapes having various cross-section can be extruded. The invention gels can also be formed directly into articles or remelted in any suitable hot melt applicator and extruded into shaped articles and films or spun into threads, strips, bands, yarns, or other shapes. With respect to various shapes and yarn, its size are conventionally measured in denier (grams/9000 meter), tex (grams/1000 meter), and gage (1/2.54 cm). Gage, tex, denier can be converted as follows: tex=denier/9=specific gravity (2135/gage), for rectangular cross section, tex =specific gravity (5806×103)(th)(w)/9, where th is the thickness and w the width of the strip, both in centimeters. General descriptions of (1) block copolymers, (2) elastomeric fibers and conventional (3) gels are found in volume 2, starting at pp. 324–415, volume 6, pp 733–755, and volume 7, pp. 515 of ENCYCLOPEDIA OF POLYMER SCIENCE AND ENGINEERING, 1987 which volumes are incorporated herein by reference.

The invention gels are excellent for cast molding and the molded products have various excellent characteristics which cannot be anticipated form the properties of the raw components. Other conventional methods of forming the composition can be utilized.

Not only do the invention gels have all the desirable combination of physical and mechanical properties substantially similar to high viscosity amorphous S-EB-S gels such as high elongation at break of 1,600%, ultimate tensile strength of about 8×10⁵ dyne/cm² and higher, low elongation set at break of substantially not greater than about 2%, substantially about 100% snap back when extended to 1,200% elongation, and a gel rigidity of substantially from about 2 gram to about 1,800 gram Bloom and higher, the invention gels of the present invention exhibit improved tear resistance and resistance to fatigue not obtainable from amorphous S-EB-S gels at corresponding gel rigidities.

The invention gels of the present invention exhibit one or more of the following properties. These are: (1) tensile strength of about 8×10⁵ dyne/cm² to about 10⁷ dyne/cm² and greater; (2) elongation of less than about 1,600% to about 3,000% and higher; (3) elasticity modules of about 10⁴ dyne/cm² to about 10⁶ dyne/cm² and greater; (4) shear modules of about 10⁴ dyne/cm² to about 106 dyne/cm² and greater as measured with a 1, 2, and 3 kilogram load at 23° C.; (5) gel rigidity of about less than about 2 gram Bloom to about 1,800 gram Bloom and higher as measured by the gram weight required to depress a gel a distance of 4 mm with a piston having a cross-sectional area of I square cm at 23° C.; (6) tear propagation resistance greater than the tear resistance of amorphous S-EB-S gels at corresponding gel rigidities; (7) resistance to fatigue greater than the fatigue resistance of amorphous S-EB-S gels at corresponding gel rigidities; (8) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The invention gel articles molded from the invention gels have additional important advantages in that they end-use performance properties are greater than amorphous S-EB-S gels in that they are more resistant to cracking, tearing, crazing or rupture in flexural, tension, compression, or other deforming conditions of use. Like amorphous gels, the molded articles made from the instant composition possess the intrinsic properties of elastic memory enabling the articles to recover and retain its original molded shape after many extreme deformation cycles.

Because of their improved tear resistance and improved resistance to fatigue, the invention gels of the present invention achieve greater performance than amorphous gels in low frequency vibration applications, such as viscoelastic layers in constrained-layer damping of mechanical structures and goods, as viscoelastic layers used in laminates for isolation of acoustical and mechanical noise, as anti-vibration elastic support for transporting shock sensitive loads, as vibration isolators for an optical table, as viscoelastic layers used in wrappings, enclosures and linings to control sound, as compositions for use in shock and dielectric encapsulation of optical, electrical, and electronic components.

Because of their improved tear resistance and improved resistance to fatigue, the invention gels are more useful as molded shape articles for use in medical and sport health care, such use include therapeutic hand exercising grips, dental floss, crutch cushions, cervical pillows, bed wedge pillows, leg rest, neck cushion, mattress, bed pads, elbow padding, dermal pads, wheelchair cushions, helmet liner, cold and hot packs, exercise weight belts, traction pads and belts, cushions for splints, slings, and braces (for the hand, wrist, finger, forearm, knee, leg, clavicle, shoulder, foot, ankle, neck, back, rib, etc.), and also soles for orthopedic shoes. Other uses include various shaped articles, optical uses (e.g., cladding for cushioning optical fibers from bending stresses) and various optical devices, as lint removers, dental floss, as tips for swabs, as fishing bait, as a high vacuum seal (against atmosphere pressure) which contains a useful amount of a mineral oil-based magnetic fluid particles, safety airbags, medical bags, e.g. IV solution bags, blood bags and dialysis bags, etc.

The invention gels of the invention find use as airbags designed for rapid deployment by expanding pressurized or ignitable gas as described in my pending application U.S. Ser. No. 09/130545 which is incorporated herein above by reference.

The various components of the airbag are denoted by: 1 Shape of gel expansion envelop. 2 Gel, 3 External retainer, 5 internal retainer, 6 reinforcing retainer, 7 mechanical retainer, 8 semi integral retainer, 9 integral pin retainer, 10 partial external integral retainer, 12 body, 13 gas inlet from filter, 14 outer sheet, 15 inner sheet, 16 eye retainer ring cavity, 18, back partial integral retainer, 19 T retainer (integral reinforcing), 20 thin gel diaphram, 21 thick gel diaphragm, 22 multiple progressive thinner gel diaphragm, 23 multiple progressive thicker gel diaphragm, 24 multiple single layer expansion control elements, 25 single layer expansion control elements, 26 dual single layer expansion control elements, 27 multiple layer expansion control elements, 28 multiple layer diverted elements, 29 patterned MDE, 31 full retained gel cup, 32 partial retained gel cup, 33 gel cavity, 34S gel shaped, 35 bulged gel, 36 compact assembly, 37 double layered, 38 multiple window, 39 double gel, 40 baffle, 41 gel dia., 42 expanded 7a–7d, 43 non-uniform gel dia., 44 gel retainer, 45 restrained envelope, 46 non-uniform gel expanded mass, 47 expansion retainer assembly, 48 expansion control elements, 50 dual expansion dia., 52 single, 54 internal and external, 56 triple, 57 multiple layered, 58 triple internal, 59 triple small and dural large, 60 equal triple, 61 dural internal with single external surround dia., 10c driver gel dia. 10d enveloping driver dummy, 10e enveloping passenger dummy, 11 conventional air bag deployment, 12 ge and break-out pressures, 13 gel diameter expansion final pressures.

The expansion of the gel air bag is substantially pure volume expansion or dilation as related to K, bulk modulus, y, young's modulus: K=y/3(1−2t), t=3k−2n/6k−2n, where t=poisson's ratio, b=1/k compressibility=−change in V/(V·change in pressure P).

Surface expansion measure of air bag from initial to expanded state is from 630 to 833% depending on thickness of original air bag. The initial air bag thickness can vary from 0.5 cm to 10 cms. (0.5, 1, 2, 3, 4, 5, 6, 7, 8, 9, 10 cm and higher).

As disclosed in my pending patent application U.S. Ser. No. 10/273828, very thin films of the gels of the invention are suitable for use as artificial muscles in the form of thin films wrapped into a cylinder. The gel film stretch when one side of a film is given a positive charge and the other a negative. The charges cause each wrapped film to contract toward the center of the cylinder which forces the cylinder to expand lengthwise. When the power supply is off, the cylindrical muscles relaxes. Thus, the roll up gel can push, pull, and lift loads.

A thin films or membrane of the gels having a thickness of about 5 mm to less than 0.1 mm are useful as artificial muscles. Film thickness of from and in between: 0.005 mm, 0.01 mm, 0.02 mm, 0.03 mm, 0.04 mm, 0.05 mm, 0.06 mm 0.07 mm, 0.08 mm, 0.09 mm, 0.10 mm, 0.2 mm, 0.3 mm, 0.4 mm, 0.5 mm, 0.6 mm, 0.7 mm, 0.8 mm, 0.9 mm, 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3.0 mm, 3.1 mm, 3.2 mm, 3.3 mm, 3.4 mm, 3.5 mm, 3.6 mm, 3.7 mm, 3.8 mm, 3.9 mm 4.0 mm can be utilized for forming artificial muscles of the invention.

Fine powder of the common transition metals can be utilized as a coating electrodes on the top and bottom flat sides of the gel film to serve as conductor, such as aluminum, alpha aluminum, copper, silver, gold, tin, nickel, iron, cobalt, zinc, lead, and the like.

We denote "l" as a gel film layer, G, and "ll" as two gel film layers, GG, side by side, "lll" as three gel film layers, GGG, side by side. We denote E as a metal electrode or conductor electrode on both sides of the G film layer, such as EGE, EGEGEE, EGEGEGE, EGEGEGEGE and the like. We denote (+) as a positive charge, (−) as a negative charge. We then denote the single charged membrane or film layer as "(+)ElE(−)" showing a single gel layer with electrodes on both sides and a positive charge on its left side and a negative charge on its right side. Hence "(+)ElE(−)(−)ElE(+)", denotes a double gel thin film layers with electrodes on each side of the film layers and charged from left to right as positive, negative, negative, and positive. This arrangement allows for the rolling up of the double layers into a cylindrical cylinder without discharging the double layers by rolling unto itself. Another way of rolling up a thin gel film "(+)ElE(−)" require folding the (−) side with the (−) sides as a continuous S curve layers upon layers and then rolling the S curve so that the same charged sides roll unto itself into a cylinder. Other combination can be made for use as charged thin film layers for artificial muscle use, such as a) (+)ElE(−),
b) (+)ElE(−)(−)ElF(+),
c) (+)ElE(−)(−)ElE(+)(+)ElE(−),
d) (+)ElE(−)(−)ElE(+)(+)ElE(−)(−)ElE(+), and
e) (+)ElF(−)(−)ElE(+)(+)ElE(−)(−)ElE(+)(+)ElE(−).

Moreover, the gels films can be formed as multiple layers of films with separating electrical conducting layer with encapsulated connectors for easy folding.

The diameter of the rolled up gel cylinder can be from about 1 mm to abut 8 mm, suitably, about 0.5 mm to about 5 mm, more suitably about 1 mm to about 3 mm. Generally the rolled up diameter can be from less than 0.5 mm to about 12 mm or larger. The length of the cylinder can be almost any suitable length, from about 5 mm to about 50 mm, suitably, 8 mm to 20 mm, more suitably from less than 8 mm to 12 mm and longer.

Conductive connectors (of foil, polymer, or conductive gel) can be attached to the inner and outer electrodes respectively. The direct current voltage from a regulated power supply or predetermined voltage positive or negative potential source can be applied which voltage can range from less than 100 volts to greater than 10,000 volts. Voltages of 1,000 v, 2,000 v, 3,000 v, 4,000 v, 5,000 v, 6,000 v, 7,000 v, 8,000 v, 9,000 v, 10,000 v, 12,000 v, 15,000 v, 18,000 v can also be used. The voltages can be regulated selectively by hand or an electronic timer from less than one thousands of a second to minutes, hours, and days duration. Electrical timing of the applied voltages can range from a few micro seconds and longer.

The gel film can be made by conventional extrusion, hot melt spin coating, casting, dipping and the like. The artificial muscle made in this manner are useful as contractible muscle elements for small robots which gel film, contracts in thickness and extends in length and width due to the electrostatic forces when a voltage is applied. The gel cylinder increases and decreases in volume thickness so as to expand and contract lengthwise due to the electrostatic forces of the charges on the opposite dielectric surfaces of the gel film. This effect is a function of the dielectric constant of the gel. In order to provide for a muscle with a large strain and therefore a large actuation pressure (greater than 5 MPa). The performance, efficiency and faster response of the cylindrical muscle depends on the amount of strain obtained under elongation. The higher strain under elongation, the better the performance, the better the efficiency, and the faster the response.

Gel muscles actuators made from thin films having greater polyethylene crystallinity are found to produces greater performance, greater efficiency, and faster response than amorphous gels. This result is due to the greater strain performance under elongation. The elongation of the gels of the invention can range from about 100% to greater than 3,000%. The actuation pressure of the actuators made from the gels of the invention can range from about 5 MPa to greater than about 12 MPa. As an example, a 15 layer rolled/folded gel film actuator having a active muscle length of 10 mm and a diameter of 3 mm (made from 0.5 mm thick SEEPS 500 gram Bloom gel) can achieve a stroke of about 3 mm and a force of about 5 grams.

The strain under elongation of the copolymers forming the gels can range from less than 8 MPa to about 18 Mpa and higher as measure at a strain rate of 1000%/min., from less than 5 MPa to about 25 MPa and higher as measure at a strain rate of 100%/min., and from less than 5 MPa to about 30 MPa and higher as measure at a strain rate of 10%/min. Reference (19) reports the fracture strain % and corresponding modulus (Mpa) for Ethylene-styrene copolymers ES16, ES24, ES27, ES28, ES28, and ES30 are 666/52.5, 517/26.4, 453/25, 564/19.5 and 468/25.4 respectively.

The ability to reduce the number of layers, increase strain with elongation, reduce the size of the active muscle actuator and increase the stroke distance at a greater force can be achieved with gels (exhibiting high strain under elongation) made from copolymers having one or more polyethylene components.

Moreover, the casted, extruded, or spun threads, strips, yarns, tapes can be weaved into cloths, fine or coarse fabrics. The forms of the invention gel yarn can be bare, double-covered, single-covered or coreplied, and core-spun. The invention gels can also be made into fibers such as side-side fibers, sheath-core fibers, multiple-segment fibers, island-in-the-sea fibers, and matrix-fibril.

The weaved invention gels are of great advantage for forming orthotics and prosthetic articles described above because such devices made from weaved invention gels of fine to coarse fabrics will allow for the human skin to breathe. The openings between weaved strands allows for air and oxygen transport between the skin and outer portions of the gel device body. Moreover, fine oriented or non-oriented invention gels (made from SEEBS, SEEPS, E-S-E, SEEPES, SEPEEPS and the like) in the form of threads or yarns can be produced by extruding, spinning or forced through a collection of jet nozzles to form a invention gel spray to produce porous gel non-woven matting or webs which are skin oxygen/air breathe-able fabrics and articles. Unlike the elastomeric nonwoven webs made at 290° C. of U.S. Pat. No. 4,692,371, the invention gels must be formed advantageously below 180° C, more advantageously at about 175° C. or lower because of the extremely high amount of plasticizer components. If the invention gels are heated to above 200° C. and higher, the result is a puddle of hot liquid gel mass and not the porous individual form strands forming the desired fabrics. Furthermore, the invention gels are superior in properties than any gels made from amorphous SEBS gels of substantially corresponding rigidities.

Porous, webbing or matting that are skin breathe-able comprising invention gel strands can be formed into a webs or matting by cold forming sandwiched invention gels strand-s using alkyl cyanoacrylates such as ethyl, butyl, methyl, propyl cyanoacrylates and the like. The alkyl cyanoacrylates (AC) will interlock with the gels of the invention, thereby resulting in gel-(AC)-gel webbing or matting articles. Alkyl cyanoacrylates are useful for interlocking invention gels of the invention with other substrates such as pottery, porcelain, wood, metal, plastics, such as acrylics, ABS, EPDM, nylon Fiberglass, phenoics, plexiglass, polycarbonate, polyesters, polystyrene, PVC, urethanes and the like. Other cyanoacrylates such as cyanoacrylate ester are inhibited interlocking with the invention gels of the invention.

The invention gels can be formed in any shape; the original shape can be deformed into another shape (to contact a regular or irregular surface) by pressure and upon removal of the applied pressure, the composition in the deformed shape will recover back to its original shape.

As an example of the versatility of use of the invention gels, a hand exerciser can be made in any shape so long as it is suitable for use as a hand exerciser: a sphere shape, a cube shape, a rectangular shape, etc. Likewise, a wheelchair cushion can be made from the composition in any shape, so long as it meets the needs of the user of the cushion. For example, a cushion can be made by forming the composition into a selected shape matching the contours of the specific body part or body region. The composition can be formed into any desired shaped, size and thickness suitable as a cushion; the shaped composition can be additionally surrounded with film, fabric, foam, or any other desired material or combinations thereof. Moreover, the composition can be casted onto such materials, provided such materials substantially maintain their integrity (shape, appearance, texture, etc.) during the casting process. The same applies for brace cushions, liners, linings and protective coverings for the hand, wrist, finger, forearm, knee, leg, etc.

Because of their improved tear resistance and resistance to fatigue, the invention gels exhibit versatility as balloons for medical uses, such as balloon for valvuloplasty of the mitral valve, gastrointestinal balloon dilator, esophageal balloon dilator, dilating balloon catheter use in coronary angiogram and the like.

Other uses include self sealing enclosures for splicing electrical and telephone cables and wires. For example, the invention gels can be pre-formed into a small diameter tubing within an outer elastic tubing, both the internal invention gel tubing and external elastic tubing can be axially expanded and fixed in place by a removable continuous retainer. Upon insertion of a spliced pair or bundle of cables or wires, the retainer can be removed, as the retainer is removed, the invention gel and elastic tubing impinges onto the inserted cables or wires splices, thereby sealing the electrical splices against weather, water, dirt, corrosives and shielding the splice from external abuse. The enclosure is completed without the use of heat or flame as is conventionally performed.

Because of their improved resistance to tearing, the invention gels do not tear as readily as amorphous gels when used as dental floss. The dental floss can be almost any shape so long as it is suitable for dental flossing. A thick shaped piece of the composition can be stretched into a thin shape and used for flossing. A thinner shaped piece would require less stretching, etc. For purposes of dental flossing, while flossing between two closely adjacent teeth, especially between two adjacent teeth with substantial contact points and more especially between two adjacent teeth with substantial amalgam alloy metal contact points showing no gap between the teeth, it is critical that the invention gel resist tearing, shearing, and crazing while being stretched to a high degree in such situations. For example, dental invention gel floss can take the form of a disk where the segments of the circumference of the disk is stretched for flossing between the teeth. Other shaped articles suitable for flossing include threads, strips, yarns, tapes, etc., mentioned above.

In order for invention gels to be useful as a dental floss, it must overcome the difficult barriers of high shearing and high tearing under extreme elongation and tension loads. The difficulties that the invention gels must overcome during flossing can be viewed as follows: during the action of flossing, the invention gel is stretched from no less than about 200% to about 1,100% or higher, the invention gel floss is deformed as it is pulled down with tearing action between the contacting surfaces of the teeth, then, the wedge of invention gel floss is sheared between the inner contacting surfaces of the teeth, and finally, the elongated wedged of invention gel floss is pulled upwards and out between the surfaces of the teeth. The forces encountered in the act of flossing are: tension, shearing, tearing under extreme tension.

The use of invention gels advances the flossing art by providing strong, soft, and more tear resistant gels than amorphous gels. Floss made from the invention gels has many advantages over conventional dental floss such as regular and extra fine waxed and unwaxed nylon floss, spongy nylon fiber floss and waxed and unwaxed expanded and unexpended teflon floss. Such conventional floss are not recommended for use by children, since a slip or sudden snap in forcing the floss between the teeth can cause injury to the gums which often times results in bleeding. For sensitive gums and inflamed gums which has become red and puffy, it is difficult to floss at, near, and below the gumline. The soft invention gel floss with softness substantially matching the softness of the gums are of great advantage for use by children and for flossing teeth surrounded by sensitive and tender gums.

In all cases, the tear strength of invention gels are higher than that of amorphous gels. The rigidities of the invention gels for use as dental floss advantageously should be selected to exhibit a propagating tear force (when propagating a tear as measured at 180° U bend around a 5.0 mm diameter mandrel attached to a spring scale) of about 1 Kg/cm, more advantageously 2 Kg/cm, and still more advantageously of about 3 Kg/cm and higher. For any gel to be considered useful for flossing, the gels should exhibit tear strengths of 2 Kg/cm and higher, advantageously of 4 Kg/cm and higher, more advantageously of 6 Kg/cm and higher, exceptionally more advantageously of 8 Kg/cm and higher. Typically, the tear propagation strength should range from about 5 Kg/cm to about 20 Kg/cm and higher, more typically from about less than 5 Kg/cm to about 25 Kg/cm and higher, especially more typically form about less than 6 Kg/cm to about 30 Kg/cm and higher, and exceptionally more typically from about less than 8 Kg/cm to about 35 Kg/cm and higher.

For any gel to be considered useful for flossing, the gels, critically, should advantageously exhibit a propagating tension tear force (when a cylindrical sample is notched and a tear is initiated at the notched area and propagated past its maximum cylindrical diameter by length-wise stretching of the cylindrical sample) of about 1 Kg/cm, more advantageously 2 Kg/cm, and still more advantageously of about 4 Kg/cm and higher. Although the invention gels of the present invention have improved tear resistance and resistance to fatigue greater than the amorphous gels at corresponding gel rigidities, the high and ultra-high tear resistant gels of my other related parent and c-i-p applications typically will exhibit even higher tear resistance values.

The invention gels of the invention can be use for making air bags. The expansion of the gel air bag is substantially pure volume expansion or dilation as related to K, bulk modulus, y, young's modulus: K=y/3(1−2t), t=3k−2n/6k−2n, where t=poisson's ratio, b=1/k compressibility=−change in V/(V·change in pressure P).

Surface expansion measure of air bag from initial to expanded state is from 630 to 833% depending on thickness of original air bag. The initial air bag thickness can vary from 0.5 cm to 10 cms. (0.5, 1, 2, 3, 4, 5, 6, 7, 8, 9, 10 cm and higher).

While advantageous components and formulation ranges based on the desired properties of the invention gels have been disclosed herein. Persons of skill in the art can extend these ranges using appropriate material according to the principles discussed herein. All such variations and deviations which rely on the teachings through which the present invention has advanced the art are considered to be within the spirit and scope of the present invention.

The invention is further illustrated by means of the following illustrative embodiments, which are given for purpose of illustration only and are not meant to limit the invention to the particular components and amounts disclosed.

EXAMPLE I

Gels of 100 parts of Kraton G1651, Kraton RP-6917 (amorphous S-EB-S), Septon 8006 (amorphous S-EB-S), Kraton RP-6918, Septon S2006 (amorphous S-EP-S) and a high viscosity radial amorphous midblock segment $(SEB)_n$ triblock copolymers and 1,600, 1,200, 1,000, 800, 600, 500, 450, 300, 250 parts by weight of Duraprime 200 white oil (plasticizer having Vis. cSt @ 40° C. of 39.0) are melt blended, test, and tack probe samples molded, the bulk gel rigidities are found to be within the range of 2 to 1,800 gram Bloom and the tensile strength, notched tear strength, and resistance to fatigue are found to decrease with increase amounts of plasticizers, while tackiness of the gels is found to be greater than 7.6 gram Tack.

EXAMPLE II

Gels of 100 parts of Septon crystalizable (SEEPS) copolymers 4033, 4055, and 4077 and 1,600, 1,200, 1,000, 800, 600, 500, 450, 300, 250 parts by weight of Duraprime 200 white oil (plasticizer having Vis. cSt @ 40° C. of 39.0) are melt blended, test and tack probe samples molded, the bulk gel rigidities are found to be within the range of 2 to 1,800 gram Bloom and the gel tackiness are found to increase with increase amounts of plasticizers and the tack greater than 7.6 gram Tack.

EXAMPLE III

Gels of 100 parts of Septon crystalizable (SEEPS) copolymers 4033, 4055, and 4077 in combination with sufficient amounts of a Dow S series poly(ethylene/styrene) random copolymer (250,000 Mw) having a high styrene content sufficient to form gel blends with total styrene content of 37 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE IV

Gels of 100 parts of Septon 4045 (crystalizable S-E/EP-S having a styrene content of 37.6) and 1,600, 1,200, 1,000, 800, 600, 500, 450, 300, 250 parts by weight of Duraprime Klearol white oil (plasticizer having Vis. CSt @ 40° C. of 7–10) are melt blended, test and probe samples molded, the bulk gel rigidities are found to be within the range of 2 to 2,000 gram Bloom and the tackiness is found to be less than about 1 gram Tack.

EXAMPLE V

Gels of 100 parts of Septon crystalizable (SEEPS) copolymers 4033, 4055, and 4077 in combination with sufficient amounts of Septon 2104 (Amorphous SEPS having a high styrene content of 65) and 800, 600, 500, 450, 300, 250 parts by weight of Duraprime 55, 70, Kicarol, Carnation, Blandol, Benol, Semtol 85, 70, and 40 (plasticizers having Vis. CSt @40° C. of less than 20) are melt blended, tests, and tack probe samples molded, the bulk gel rigidities are found to be within the range of 2 gram to 1,800 gram Bloom and tack is found to decrease with decreasing plasticizer content and in all instances substantially lower than the gels of Example I and II.

EXAMPLE VI

Gels of 100 parts of Septon crystalizable (SEEPS) copolymers 4033, 4055, and 4077 in combination with sufficient amounts of a Dow M series poly(ethylene/styrene) random copolymer (350,000 Mw) having a high styrene content sufficient to form gel blends with total styrene content of 37 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE VII

Gels of 100 parts of Septon crystalizable (SEEPS) copolymers 4033, 4055, and 4077 in combination with sufficient amounts of a Dow E series poly(ethylene/styrene) random copolymer (240,000 Mw) having a high styrene content sufficient to form gel blends with total styrene content of 37 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE VIII

Gels of 100 parts of Septon crystalizable (SEEPS) copolymers 4033, 4055, and 4077 in combination with polystyrene homopolymers (having Mw of 3,000; 4,000; 5,000; 6,000; 7,000; 8,000; 9,000; 10,000; 11,000; 12,000; 13,000; 14,000; 15,000; 16,000; 17,000; 18,000; 19,000; 20,000; 30,000; 40,000; 50,000; 60,000; 70,000; 80,000; 90,000) in sufficient amounts to form gel blends with total styrene content of 37, 45, 48, 50, and 55 by weight of copolymers and 800, 600, 500, 450, 300, 250 parts by weight of Duraprime 55,70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 2,000 gram Bloom and tack is found to decrease with decreasing plasticizer content and in all instances substantially lower than the gels of Example I and II.

EXAMPLE IX

Gels of 100 parts of Septon crystalizable (SEEPS) copolymers 4033, 4055, and 4077 in combination with sufficient amounts of a Dow M series poly(ethylene/styrene) random copolymer (350,000 Mw) having a high styrene content sufficient to form gel blends with total styrene contents of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE X

Gels of 100 parts of Septon crystalizable (SEEPS) copolymers 4033, 4055, and 4077 in combination with sufficient amounts of a Dow S series poly(ethylene/styrene) random copolymers (with Mw of 140,000; 250,000 and 340,000) having a high styrene content sufficient to form gel blends with total styrene content of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XI

Gels of 100 parts of Septon crystalizable (SEEPS) copolymers 4033, 4055, and 4077 in combination with sufficient amounts of a Dow E series poly(ethylene/styrene) random copolymers (with Mw of 250,000; 340,000 and 400,000) having a high styrene content sufficient to form gel blends with total styrene content of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XII

Gels of 100 parts of Septon crystalizable (SEPS) copolymers 4033, 4055, and 4077 in combination with sufficient amounts of a Dow M series poly(ethylene/styrene) random copolymer (with Mw of 250,000; 340,000 and 400,000) having a high styrene content sufficient to form gel blends with total styrene content of 40, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XIII

Gels of 100 parts of Dow E series crystalizable poly(ethylene/styrene) random copolymer (with Mw of 250,000; 340,000 and 400,000) having a high styrene content sufficient to form gel blends with total styrene content of 37, 40, 45, 48, 50, 55, and 60 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I, while tack is found to decrease with decreasing plasticizer content and in all instances substantially lower than the gels of Example I and II.

EXAMPLE XIV

Gels of 100 parts of Septon crystalizable (SEEPS) copolymers 4033,4055, and 4077 in combination with polystyrene (of 2,500 Mw, 4,000 Mw, 13,000 Mw, 20,000 Mw, 35,000 Mw, 50,000 Mw, and 90,000 Mw; poly(alpha-methylstyrene) (of 1,300 Mw, 4,000 Mw; poly(4-methylstyrene)(of 72,000 Mw), Endex 155, 160, Kristalex 120, and 140) in sufficient amounts to form gel blends with total styrene content of 37, 45, 48, 50, and 55 by weight of copolymers and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. ° C. of less than 20) are melt blended, tests, and tack probe samples molded, the bulk gel rigidities are found to be within the range of 2 gram to 2,000 gram Bloom and tack is found to decrease with decreasing plasticizer content and in all instances substantially lower than the gels of Example I and II.

EXAMPLE XV

Examples XIV is repeated and gels of 100 parts of (S-EB$_{45}$-EP-S), (S-E-EB$_{25}$-S), (S-EP-E-EP-S), (S-E-EB-S), (S-E-EP-S), (S -E-EP-E-S), (S-E-EP-EB-S), (S-E-EP-E-EP-S). (S-E-EP-E-EB-S), (S-E-EP-E-EP-E-S), (S-E-EP-E-EB-S), (S-E-EP-E-EP-EB-S), and (S-E-EP-E-EP-E-S) block copolymers are each melt blended, tests and probe samples molded, the bulk gel rigidities are found to be within the range of 2 to 1,800 gram Bloom and tack is found to decrease with decreasing plasticizer content and in all instances substantially lower than the gels of Example I and II.

EXAMPLE XVI

Example XIV is repeated and minor amounts of 2, 5, 10 and 15 parts of the following polymers are formulated with each of the triblock copolymers: styrene-butadiene-styrene block copolymers, styrene-isoprene-styrene block copolymers, low viscosity styrene-ethylene-butylene-styrene block copolymers, styrene-ethylene-propylene block copolymers, styrene-ethylene-propylene-styrene block copolymers, styrene-butadiene, styrene-isoprene, polyethyleneoxide, poly (dimethylphenylene oxide), polystyrene, polybutylene, polyethylene, polypropylene, high ethylene content EPDM, amorphous copolymers based on 2,2-bistrifluoromethyl-4, 5-difuoro-1,3-dioxole/tetrafluoroethylene. The bulk gel rigidities of each of the formulations are found to be within the range of 2 gram to 2,000 gram Bloom and tack is found to decrease with decreasing plasticizer content and in all instances substantially lower than the gels of Example I and II.

EXAMPLE XVII

Molten gels of Examples III–XVI are formed into s with paper, foam, plastic, elastomers, fabric, metal, concrete, wood, glass, ceramics, synthetic resin, synthetic fibers, and refractory materials and the resistance to fatigue of the invention gels at corresponding rigidities are found to be greater than that of the -amorphous gels of Example I.

EXAMPLE XVIII

Three cm thick sheets of each of the invention gels of Example XIV and the amorphous gels of Example I are tested by repeatedly displacing the sheets to a depth of 1 cm using a 10 cm diameter smooth (water soaked) wood plunger for 1,000, 5,000, 10,000, 25,000, 50,000, and 100, 000 cycles. The sheets of invention gels are found capable of exhibiting greater fatigue resistance than the sheets of amorphous gels at corresponding rigidities.

EXAMPLE XIX

Gels of 100 parts of Septon crystalizable (SEEPS) copolymers 4033, 4055, and 4077 in combination with sufficient amounts of a Dow poly(ethylene/styrene) random copolymers ES 16 having 37.5% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XX

Gels of 100 parts of Septon crystalizable (SEEPS) copolymers 4033, 4055, and 4077 in combination with sufficient amounts of a Dow poly(ethylene/styrene) random copolymers ES24 having 26.6% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 grain Bloom and the notched tear strength and resistance to fatigue of the gel at corresponding rigidities are found to be greater than that of amorphous gels of Example 1.

EXAMPLE XXI

Gels of 100 parts of Septon crystalizable (SEEPS) copolymers 4033, 4055, and 4077 in combination with sufficient amounts of a Dow poly(ethylene/styrene) random copolymers ES27 having 17.4% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXII

Gels of 100 parts of Septon crystalizable (SEEPS) copolymers 4033, 4055, and 4077 in combination with sufficient amounts of a Dow poly(ethylene/styrene) random copolymers ES28 having 22.9% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXIII

Gels of 100 parts of Septon crystalizable (SEEPS) copolymers 4033, 4055, and 4077 in combination with sufficient amounts of a Dow poly(ethylene/styrene) random copolymers ES30 having 19.6% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXIV

Gels of 100 parts of Septon crystalizable (SEEPS) copolymers 4033, 4055, and 4077 in combination with sufficient amounts of a Dow poly(ethylene/styrene) random copolymers ES44 having 5.0% crystallinity and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities arefound to be within the range of 2 gram to 1,800 gram Bloom and the notched tear strength and resistance to fatigue of the gel at corresponding rigidities are found to be greater than that of amorphous gels of Example I.

EXAMPLE XXV

Gels of 100 parts of Septon crystalizable (SEEPS) copolymers 4033, 4055, and 4077 in combination with sufficient amounts of a Dow poly(ethylene/styrene) random copolymers ES72 and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXVI

Gels of 100 parts of Septon crystalizable (SEEPS) copolymers 4033, 4055, and 4077 in combination with sufficient amounts of a Dow poly(ethylene/styrene) random copolymers ES73 and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXVII

Gels of 100parts of Septon crystalizable (SEEPS) copolymers 4033, 4055, and 4077 in combination with sufficient amounts of a Dow poly(ethylene/styrene) random copolymers ES74 and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXVIII

Gels of 100 parts of Septon crystalizable (SEEPS) copolymers 4033, 4055, and 4077 in combination with sufficient amounts of a Dow poly(ethylene/styrene) random copolymers ES69 and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 grain Bloom and the notched tear strength and resistance to fatigue of the gel at corresponding rigidities are found to be greater than that of amorphous gels of Example I.

EXAMPLE XXIX

Gels of 100 parts of Septon crystalizable (SEEPS) copolymers 4033, 4055, and 4077 in combination with sufficient amounts of a Dow poly(ethylene/styrene) random copolymers ES62 and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) ar melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXX

Gels of 100 parts of Septon (SEPS) copolymers Kraton GRP6918 in combination with each of a Dow poly(ethylene/styrene) random copolymers ES16, ES24, ES27, FS28, ES30, and ES44 and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXXI

Gels of 100 parts of Septon (SEBS) copolymers S8006 and Kraton G1651, G1654 in combination with sufficient amounts of a Dow poly(ethylene/styrene) random copolymers ES16, ES24, ES27, ES28, ES30, and ES44 and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXXII

Gels of 100 parts of Septon (SEEPS) copolymers 4033, 4045, 4055, 4077 in combination each with 25 parts by weight of Super Sta-tac, Betaprene Nevtac, Escorez, Hercotac, Wingtack, Piccotac, polyterpene, Zonarez, Nirez, Piccolyte, Sylvatac, glycerol ester of rosin (Foral), pentaerythritol ester of rosin (Pentalyn), saturated alicyclic hydrocarbon (Arkon P), coumarone indene (Cumar LX), hydrocarbon (Picco 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035) and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

EXAMPLE XXXIII

Gels of 100 parts of Septon (SEEPS) copolymers 4033, 4045, 4055, 4077 in combination each with 25 parts by weight of Super Sta-tac, Betaprene Nevtac, Escorez, Hercotac, Wingtack, Piccotac, polyterpene, Zonarez, Nirez, Piccolyte, Sylvatac, glycerol ester of rosin (Foral), pentaerythritol ester of rosin (Pentalyn), saturated alicyclic hydrocarbon (Arkon P), coumarone indene (Cumar LX), hydrocarbon (Piceo 6000, Regalrez), mixed olefin (Wingtack), alkylated aromatic hydrocarbon (Nevchem), Polyalphamethylstyrene/vinyl toluene copolymer (Piccotex), polystyrene (Kristalex, Piccolastic), special resin (LX-1035) and 800, 600, 500, 450, 300, 250 parts by weight of Duraprime 55, 70, Klearol, Carnation, Blandol, Benol, Semtol 85, 70, and 40 (plasticizers having Vis. CSt @ 40° C. of less than 20) are melt blended, tests, and tack probe samples molded, the bulk gel rigidities are found to be within the range of 2 gram to 1,800 gram Bloom and the notched tear strength and resistance to fatigue of the gel at corresponding rigidities are found to be greater than that of amorphous gels of Example I.

While preferred components and formulation ranges have been disclosed herein persons of skill in the art can extend these ranges using appropriate material according to the principles discussed herein. Furthermore, Crystalizable midblock segment block polymers can be use in blending with other engineering plastics and elastomeric polymers to make alloyed compositions having improved impact and tear resistance properties. All such variations and deviations which rely on the teachings through which the present invention has advanced the art are considered to be within the spirit and scope of the present invention.

I claim:

1. An article comprising a body shaped suit for diving, said article comprising a gelatinous elastomer composition, G, in contact with or without one or more of a selected substrate material, M, said gelatinous elastomer composition comprising:

(i) 100 parts by weight of one or a mixture of two or more of a hydrogenated styrene isoprene/butadiene block copolymner(s) and from (ii) about 300 to about 1,600 parts by weight of a plasticizing oil; and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene)$_n$, poly(styrene-ethylene-propylene-styrene), poly(styrene-ethylene-butylene-styrene), poly(styrene-ethylene-butylene)$_n$, poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said article formed from $G_n$, the combination $G_nG_n$, $G_nM_n$, $G_nM_nM_nG_n$, $G_nG_nM_nM_n$, $G_nM_nG_nM_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with or without one or more $M_n$; wherein when n is a subscript of M, n is the same or different selected from the group consisting of foam, plastic, fabric, metal, ceramics, synthetic resin, synthetic fibers or refractory materials; and wherein when n is a subscript of G, n denotes the same or a different gel rigidity; said article made by injection molding, extruding, spinning, casting, or dipping of said gelatinous elastomer composition.

2. An article comprising a body shaped suit for diving, said article comprising a gelatinous elastomer composition, G, in contact with one or more of a selected substrate material, M, said gelatinous elastomer composition comprising:

(i) 100 parts by weight of one or a mixture of two or more of a hydrogenated styrene isoprene/butadiene block copolymer(s) and (ii) from about 300 to about 1,600 parts by weight of an plasticizing oil; in combination with or without (iii) a selected amount of one or more polymer or copolymer of poly(styrene-butadiene-styrene), poly(styrene-butadiene)$_n$, poly(styrene-isoprene-styrene), poly(styrene-isoprene)$_n$, poly(styrene-ethylene-propylene)$_n$, poly(styrene-ethylene-propylene-styrene), poly(styrene-ethylene-butylene-styrene), poly(styrene-ethylene-butylene)$_n$, poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, branched, star-shaped, or multiarm copolymer, and n is an integer greater than one; wherein said composite formed from the combination $G_nM_n$ of said $G_n$ with $M_n$; wherein when n is a subscript of M, n is the same or different selected from the group consisting of foam, plastic, fabric, metal, ceramics, synthetic resin, synthetic fibers or refractory materials; and wherein when n is a subscript of G, n denotes the same or a different gel rigidity; and wherein when n is a subscript of G, n denotes the same or a different gel rigidity; said article made by injection molding, extruding, spinning, casting, or dipping of said gelatinous elastomer composition.

3. An article comprising a body shaped suit for diving, said article comprising a gelatinous elastomer composition, G, in contact with or without one or more of a selected substrate material, M, said gelatinous elastomer composition comprising:

(i) 100 parts by weight of one or more of a hydrogenated styrene isoprene/butadiene block copolymer(s) selected from a hydrogenated styrene block polymer with hydrogenated elastomer midblocks of poly(2-methyl-1,3-butadiene) and poly(1,3-butadiene), a hydrogenated styrene block polymer with hydrogenated elastomer midblocks of poly(2-methyl-1,3-butadiene and 1,3-butadiene), and a poly(styrene-ethylene-ethylene-propylene-styrene) and (ii) from about 300 to about 1,600 parts by weight of an plasticizing oil; in combination with or without (iii) a selected amount of one or more selected polymer or copolymer selected from the group consisting of poly (styrene-butadiene-styrene), poly(styrene-butadiene), poly(styrene-isoprene-styrene), poly(styrene-isoprene), poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, branched, star-shaped, or multiarm copolymer; and n is an integer greater than one, wherein said gelatinous elastomer compositions characterized by a gel rigidity of from about 20 to about 800 gram Bloom; wherein said article formed from $G_n$, the combination $G_nG_n$, $G_nM_n$, $G_nM_nM_nG_n$, $G_nG_nM_nM_n$, $G_nM_nG_nM_nM_n$, $G_nM_nG_n$, $M_nG_nM_n$, $G_nG_nM_n$, $M_nM_nM_nG_n$, $M_nM_nM_n$ $G_nM_n$, $M_nG_nG_nM_n$, $G_nM_nG_nG_n$, $G_nM_nM_nG_n$, $G_nG_nM_n$ $M_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with or without one or more $M_n$; wherein when n is a subscript of M, n is the same or different selected from the group consisting of foam, plastic, fabric, metal, ceramics, synthetic resin, synthetic fibers or refractory materials; and wherein when n is a subscript of G, n denotes the same or a different gel rigidity; and wherein when n is a subscript of G, n denotes the same or a different gel rigidity; said article made by injection molding, extruding, spinning, casting, or dipping of said gelatinous elastomer composition.

4. An article comprising a body shaped suit for diving, said article comprising a gelatinous elastomer composition, G, in contact with or without one or more of a selected substrate material, M, said gelatinous elastomer composition comprising:

(i) 100 parts by weight of one or more of a hydrogenated styrene isoprene/butadiene block copolymer(s) selected from a hyrogenated styrene block polymer with hydrogenated elastomer midblocks of poly(2-methyl-1,3-butadiene) and poly(1,3-butadiene), a hydrogenated styrene block polymer with hydrogenated elastomer midblocks of poly(2-methyl-1,3-butadiene and 1,3-butadiene), and a poly(styrene-ethylene-ethylene-propylene-styrene); and (ii) from about 300 to about 1,600 parts by weight of an plasticizing oil, in combination with or without (ii) a selected amount of one or more polymers or copolymers of poly(styrene-butadiene-styrene), poly(styrene-butadiene)$_n$, poly(styrene-isoprene-styrene), poly(styrene-isoprene)$_n$, poly(styrene-ethylene-propylene)$_n$, poly(styrene-ethylene-propylene-styrene), poly(styrene-ethylene-butylene-styrene), low viscosity poly(styrene-ethylene-butylene-styrene), poly(styrene-ethylene-butylene)$_n$, polystyrene, polybutylene, poly(ethylene-propylene), poly(ethylene-butylene), polypropylene, or polyethylene, wherein said selected copolymer is a linear, branched, radial, star-shaped, or multiarm copolymer; and n is an integer greater than one; wherein said article formed from $G_n$, the combination $G_nG_n$, $G_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_n$ $G_n$, $G_nM_nM_nG_n$, $G_nG_nM_nM_n$, $G_nG_nM_nG_nM_n$, $G_nM_nG_n$ $M_nM_n$, $M_nG_nM_nG_nM_nG_n$, $G_nG_nM_nM_nG_n$, $G_nG_nM_nG_n$ $M_nG_n$, a sequential addition or a permutation of one or more of said $G_n$ or without one or more $M_n$, wherein when n is a subscript of M, n is the same or different selected from the group consisting of foam, plastic, fabric, metal, ceramics, synthetic resin, synthetic fibers or refractory materials; and wherein when n is a subscript of G, n denotes the same or a different gel rigidity; and wherein when n is a subscript of G, n denotes the same or a different gel rigidity; said article made by injection molding, extruding, spinning, casting, or dipping of said gelatinous elastomer composition.

5. A article of claim 1, 2, 3, or 4, wherein said (iii) polymer is selected from poly(styrene-butadiene-styrene), poly(styrene-ethylene-butylene/ethylene-propylene-styrene), poly(styrene-ethylene-butylene/styrene-ethylene-butylene-styrene), poly(styrene-ethylene-propylene/styrene-ethylene-propylene-styrene), poly(styrene-ethylene-butylene-styrene), poly(styrene-ethylene-propylene), low viscosity poly (styrene-ethylene-butylene-styrene), and poly(styrene-ethylene-butylene/ethylene-propylene-styrene).

6. A article of claim 1 or 4, wherein said (iii) polymer is selected from poly(styrene-ethylene-butylene/ethylene-propylene-styrene), poly(styrene-ethylene-butylene/styrene-ethylene-butylene-styrene), poly(styrene-ethylene-propylene/styrene-ethylene-propylene-styrene), and poly(styrene-ethylene-butylene/ethylene-propylene-styrene).

7. A article of claim 1, 2, 3, or 4, wherein said (iii) polymer is selected from poly(styrene-ethylene-butylene/styrene-ethylene-butylene-styrene), poly (styrene-ethylene-propylene/styrene-ethylene-propylene-styrene), and poly(styrene-ethylene-butylene/ethylene-propylene-styrene).

8. A article of claim 2, 3, or 4 wherein said (i) hydrogenated styrene isoprene/butadiene block copolymers is selected from poly(styrene-ethylene-ethylene-propylene-styrene) and poly(styrene-ethylene-butylene/ethylene-propylene-styrene).

9. An article comprising a body shaped suit for diving, said article comprising a gelatinous elastomer composition, G, in contact with or without one or more of a selected substrate material, M, said gelatinous elastomer composition comprising:

(i) 100 parts by weight of one or a mixture of two or more poly(styrene-ethylene-ethylene-propylene-styrene) block copolymers and (ii) from about 300 to about 1,600 parts by weight of an plasticizing oil, and in combination with or without (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene)$_n$, poly(styrene-ethylene-propylene-styrene), poly(styrene-ethylene-butylene-styrene), low viscosity poly(styrene-ethylene-butylene-styrene), poly(styrene-ethylene-butylene/ethylene-propylene-styrene), poly(styrene-ethylene-butylene/styrene-ethylene-butylene-styrene), poly(styrene-ethylene-propylene/styreneethylene-propylene-styrene), poly(styrene-ethylene-propylene)$_n$, poly(styrene-ethylene-butylene)$_n$, polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; wherein said article formed from $G_n$, the combination $G_nG_n$, $G_nM_n$, $G_nM_nG_n$, $M_nG_nM_n$, $G_nG_nM_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with or without one or more $M_n$; wherein when n is a subscript of M, n is the same or different selected from the group consisting of foam, plastic, fabric, metal, ceramics, synthetic resin, synthetic fibers or refractory materials; and wherein when n is a subscript of G, n denotes the same or a different gel rigidity; and wherein when n is a subscript of G, n denotes the same or a different gel rigidity; said article made by injection molding, extruding, spinning, casting, or dipping of said gelatinous elastomer composition.

10. An article comprising a body shaped suit for diving, said article comprising a gelatinous elastomer composition, G, in contact with or without one or more of a selected substrate material, M, said gelatinous elastomer composition comprising:
  (i) 100 parts by weight of a block copolymer of one or a mixture of two or more poly(styrene-ethylene-ethylene-propylene-styrene block copolymers, and
  (ii) from about 300 to about 1,600 parts by weight of an plasticizing oil; in combination with or without
  (iii) a selected amount of one or more polymers or copolymers of poly(styrene-butadiene-styrene), poly(styrene-butadiene)$_n$, poly(styrene-isoprene-styrene)$_n$, poly(styrene-isoprene)$_n$, poly(styrene-ethylene-propylene), poly(styrene-ethylene-propylene-styrene), poly(styrene-ethylene-butylene-styrene), poly(styrene-ethylene-butylene), poly(styrene-ethylene-propylene)$_n$, poly(styrene-ethylene-butylene)$_n$, low viscosity poly(styrene-ethylene-butylene-styrene), styrene-butadiene-butylene-styrene), poly(styrene-ethylene-butylene/ethylene-propylene-styrene), poly(styrene-ethylene-butylene/styrene-ethylene-butylene-styrene), poly(styrene-ethylene-propylene/styrene-ethylene-propylene-styrene), poly(styrene-ethylene)-polystyrene, polybutylene, poly(ethylene-propylene), poly(ethylene-butylene), polypropylene, or polyethylene, wherein said selected copolymer is a linear, radial, star-shaped, branched or multiarm copolymer, wherein n is greater than one; and wherein said article formed from the $G_n$, the combination $G_nG_n$, $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with or without one or more $M_n$; wherein when n is a subscript of M, n is the same or different selected from the group consisting of foam, plastic, fabric, metal, ceramics, synthetic resin, synthetic fibers or refractory materials; and wherein when n is a subscript of G, n denotes the same or a different gel rigidity; and wherein when n is a subscript of G, n denotes the same or a different gel rigidity; said article made by injection molding, extruding, spinning, casting, or dipping of said gelatinous elastomer composition.

11. An article comprising a body shaped suit for diving, said article comprising a gelatinous elastomer composition, G, in contact with or without one or more of a selected substrate material, M, said gelatinous elastomer composition comprising:
  (I) 100 parts by weight of one or more of a hydrogenated styrene isoprene/butadiene block copolymer(s) selected from a hydrogenated styrene block polymer with hydrogenated elastomer midblocks of poly(2-methyl-1,3-butadiene) and poly(1,3-butadiene), a hydrogenated styrene block polymer with hydrogenated elastomer midblocks of poly(2-methyl-1,3-butadiene and 1,3-butadiene), and a poly(styrene-ethylene-ethylene-propylene-styrene), and
  (ii) from about 300 to about 1,600 parts by weight of an plasticizing oil, in combination with or without
  (iii) a selected amount of one or more polymers or copolymers of poly(styrene-ethylene-propylene)$_n$, poly(styrene-ethylene-propylene-styrene), poly(styrene-ethylene-butylene-styrene), low viscosity poly(styrene-ethylene-butylene-styrene), poly(styrene-ethylene-propylene)$_n$, poly(styrene-ethylene-butylene)$_n$, poly(styrene-ethylene-butylene/styrene-ethylene-butylene-styrene), poly(styrene-ethylene-propylene/styrene-ethylene-propylene-styrene), polystyrene, polypropylene, or wherein said selected copolymer is a linear, radial, star-shaped, branched or multiarm copolymer, wherein n is greater than one; wherein said gelatinous elastomer composition characterized by a gel rigidity of from about 20 to about 800 gram Bloom; wherein said article formed from $G_n$, the combination $G_nG_n$, $G_nM_n$, $G_nM_nG_n$, $M_nG_nM_n$, $M_nG_nG_n$, $M_nM_nM_nG_n$, $M_nM_nM_nG_nM_n$, $M_nG_nG_nM_n$, $G_nM_nG_nG_n$, $G_nM_nM_nG_n$, $G_nG_nM_nM_n$, $G_nG_nM_nG_nM_n$, $G_nM_nG_nM_nM_n$, $M_nG_nM_nG_nM_nG_n$, $G_nG_nM_nM_nG_n$, $G_nG_nM_nG_nM_nG_n$, a sequential addition or a permutation of one or more of said $G_n$ with or without one or more $M_n$; wherein when n is a subscript of M, n is the same or different selected from the group consisting of foam, plastic, fabric, metal, ceramics, synthetic resin, synthetic fibers or refractory materials; and wherein when n is a subscript of G, n denotes the same or a different gel rigidity; and wherein when n is a subscript of G, n denotes the same or a different gel rigidity; said article made by injection molding, extruding, spinning, casting, or dipping of said gelatinous elastomer composition.

12. A composite according to claims 1, 2, 3, or 4, wherein said one or more (i) block copolymers is poly(styrene-ethylene-ethylene-propylene-styrene).

* * * * *